United States Patent [19]

Ko et al.

[11] Patent Number: 5,583,147

[45] Date of Patent: Dec. 10, 1996

[54] AMIDES FOR THE TREATMENT OF ATHEROSCLEROSIS

[75] Inventors: Soo S. Ko, Wilmington; Richard G. Wilde, Newark; Indawati DeLucca, Wilmington; Hui-Yin Li; Hollis S. Kezar, III, both of Newark; George A. Boswell, Wilmington; Anurag S. Srivastava, Newark, all of Del.

[73] Assignee: The Dupont Merck Pharmaceutical Company, Wilmington, Del.

[21] Appl. No.: 216,724

[22] Filed: Mar. 23, 1994

[51] Int. Cl.$^6$ .............. C07D 414/02; C07D 213/02; A61K 31/44
[52] U.S. Cl. .............. 514/336; 514/252; 514/269; 514/299; 514/309; 514/312; 514/337; 514/341; 514/343; 514/352; 514/348; 544/298; 544/405; 546/112; 546/141; 546/153; 546/268.4; 546/261; 546/271.4; 546/272.1; 546/278.4; 546/278.7; 546/281.4; 546/283.7; 546/284.4; 546/296; 546/309; 546/280.1; 546/269.7; 546/270.7; 546/271.1; 546/274.4; 546/276.1; 546/279.1; 546/275.4; 546/281.1; 546/284.1; 546/283.1; 546/274.7; 546/277.4; 546/277.7
[58] Field of Search ................... 546/261, 265, 546/283, 284, 297, 309, 112, 141, 153, 273, 274, 278, 279, 275, 281, 296; 514/332, 335, 336, 349, 352, 269, 252, 299, 309, 312, 337, 341, 343, 348; 544/298, 405

[56] References Cited

U.S. PATENT DOCUMENTS

| 2,461,119 | 2/1949 | Lott et al. | 546/312 |
| 3,039,930 | 6/1962 | Gray | 514/352 |
| 3,165,527 | 1/1965 | Gray | 546/312 |

FOREIGN PATENT DOCUMENTS

| 1695559 | 8/1959 | Germany | 546/312 |
| 0901312 | 7/1963 | United Kingdom | 546/312 |

OTHER PUBLICATIONS

Heitmeier, *J. Med. Chem.*, vol. 7, No. 3, pp. 288–293, 1964.
Aeilmann et al, Chemical Abstracts, vol. 115, Abstract No. 232,153y, 1991, p. 94.
O'Dell et al, *J. of Pharm. Exp. Therp.*, Jan. Apr. 1960, vol. 128, pp. 65–74.
Gray et al, *J. of Amer. Chem. Soc.*, Jul. 5, 1959, vol. 81, No. 13, pp. 4347–4350.
Khalaj et al, *Synthesis*, vol. 12, 1985, pp. 1153–1155.

*Primary Examiner*—Zinna Northington Davis

[57] ABSTRACT

This invention provides amide compounds as inhibitors of acyl-Coenzyme A: cholesterol O-acyltransferase (ACAT), pharmaceutical compositions containing such compounds, processes for the preparation of such compounds, and the use of such compounds as antihypercholesterolemic and/or antiatherosclerotic agents.

33 Claims, No Drawings

5,583,147

AMIDES FOR THE TREATMENT OF ATHEROSCLEROSIS

FIELD OF THE INVENTION

This invention provides amide compounds as inhibitors of acyl-Coenzyme A: cholesterol O-acyltransferase (ACAT), pharmaceutical compositions containing such compounds, processes for the preparation of such compounds, and the use of such compounds as antihypercholesterolemic and/or antiatherosclerotic agents.

BACKGROUND OF THE INVENTION

Hypercholesterolemia is an established risk factor in the development of atherosclerosis. Therapeutic agents which control the level of serum cholesterol have proven to be effective in the treatment of coronary artery disease. While agents exist that can modulate circulating levels of cholesterol-carrying lipoproteins, these agents have little or no effect on the intestinal absorption of cholesterol. Dietary cholesterol can increase the level of serum cholesterol to levels which place an individual at increased risk for the development or exacerbation of atherosclerosis. Since much of the free or unesterified cholesterol that is absorbed by intestinal mucosal cells must first be esterified by ACAT prior to its incorporation and secretion into the bloodstream in large lipoprotein particles called chylomicrons, inhibition of ACAT can reduce the absorption of dietary cholesterol. In addition, the accumulation and storage of cholesteryl esters in the arterial wall is associated with increased activity of ACAT. Inhibition of the enzyme is expected to inhibit the formation or progression of atherosclerotic lesions in mammals.

There are an increasing number of patents in the literature disclosing compounds which are useful as ACAT inhibitors in particular and antiatherosclerotic agents in general. For example, U.S. Pat. No. 4,623,662, issued to DeVries on Nov. 18, 1986, discloses ureas and thioureas as ACAT inhibitors useful for reducing the cholesterol ester content of an arterial wall, inhibiting atherosclerotic lesion development, and/or treatment of mammalian hyperlipidemia. U.S. Pat. No. 4,722,927, issued to Holmes on Feb. 2, 1988, discloses disubstituted pyrimidineamides of oleic and linoleic acids as ACAT inhibitors useful for inhibiting intestinal absorption of cholesterol. U.S. Pat. No. 4,824,843, issued to Hoefle et al. on Apr. 25, 1989, and the related U.S. Pat. No. 4,882,357, issued to Creger et al. on Nov. 21, 1989, disclose a series of substituted N-phenyl-2,2-dimethyl-5-aryloxypentanamides, which prevent the intestinal absorption of cholesterol in mammals by inhibiting ACAT. European Patent Application 325,397, filed by Ito on Jul. 26, 1989, discloses a series of compounds consisting of two N-cycloalkyl-N'-arylurea units linked at nitrogen by a dialkylphenyl unit, which are inhibitors of the ACAT enzyme. U.S. Pat. No. 4,868,210, issued to Trivedi on Sep. 19, 1989, and the related European Patent Applications 335,374 filed by Trivedi on Mar. 30, 1988, and 386,487, filed by Trivedi on Feb. 9, 1989, disclose certain N-2,6-dialkyl- or N-2,6-dialkoxyphenyl-N'arylalkyl ureas as potent inhibitors of ACAT. European Patent Application 354,994, filed by Meguro and Ikeda on Feb. 21, 1990, discloses certain N-aryl-N'-quinolin-4-yl ureas as ACAT inhibitors. European Patent Application 370,740, filed by Jackson et al. on Nov. 21, 1988, discloses ACAT inhibitors similar in composition to those of DeVries (supra).

The following references also disclose compounds which are inhibitors of ACAT useful as antihypercholesterolemic and/or antiatherosclerotic agents: U.S. Pat. No. 4,900,744; European Patent Application EP-A-372,445; International Application WO 91/09021; International Application WO 91/10662; International Application WO 91/13876; German Laid Open Application No. DE 3504679; German Laid Open Application No. DE 3504680; European Patent Application EP 418,071 A2, filed by McCarthy et al.; and International Application WO 92/09561, filed by Itih, et al. The compounds in these references are disclosed to be inhibitors of ACAT useful for the treatment of conditions such as atherosclerosis, hyperlipidemia, cholesterol ester shortage disease and atheroma in vein grafts.

Other patents of related structure are DE 3534765 A1, issued to Pieper et al. on Apr. 2, 1987, DE 3701517 A1 issued to Nickl et al on Aug. 4, 1988, U.S. Pat. No. 3,665,031, issued to Peterli et al. on May 23, 1972, U.S. Pat. No. 4,859,707, issued to Loftsson et al. on Aug. 22, 1989, International Patent Application WO 92/07825, filed by Sato et al., and International Patent Application WO 92/09572, filed by Sato et al.

There are no known literature references disclosing the substituted mandeloamides ($\alpha$-alkoxyphenylacetamides), substituted thiomandeloamides sulfides ($\alpha$-thioalkoxyphenylacetamides), $\alpha$-alkoxyacetamides, $\alpha$-thioalkoxyacetamides, $\alpha,\alpha$-difluoroacetamides, and $\alpha$-ketoacetamides of this invention, their use as ACAT inhibitors, or their use to lower cholesterol or in the treatment of atherosclerosis. The invention of these compounds represents a potentially significant development in the area of treatment of atherosclerosis. The novel $\alpha$-alkoxy-, $\alpha$-thioalkoxy-, $\alpha,\alpha$-difluoro- and $\alpha$-keto-acetamide compounds of the improved invention have improved potency and/or bioavailability.

SUMMARY OF THE INVENTION

This invention provides novel compounds of Formula I (described below) which are useful as antihypercholesterolemic and/or antiatherosclerotic agents. The compounds of the present invention inhibit the enzyme ACAT. The present invention also includes pharmaceutical compositions containing such compounds of Formula I, and methods of using such compounds as antihypercholesterolemic and/or antiatherosclerotic agents for the lowering of cholesterol levels and/or the treatment of atherosclerosis.

Also included in the present invention are pharmaceutical kits comprising one or more containers containing pharmaceutical dosage units comprising a compound of Formula I, for use in the treatment of atherosclerosis and/or for use in lowering cholesterol levels.

DETAILED DESCRIPTION OF THE INVENTION

This invention provides novel compounds of Formula I (described below) which are useful as antihypercholesterolemic and/or antiatherosclerotic agents. The compounds of the present invention inhibit the enzyme ACAT. The present invention also includes pharmaceutical compositions containing such compounds of Formula I, and methods of using such compounds as antihypercholesterolemic and/or antiatherosclerotic agents for the lowering of cholesterol levels and/or the treatment of atherosclerosis.

Also included in the present invention are pharmaceutical kits comprising one or more containers containing pharmaceutical dosage units comprising a compound of Formula I, for use in the treatment of atherosclerosis and/or for use in lowering cholesterol levels.

The present invention provides novel compounds of Formula I, processes for the preparation of such compounds, pharmaceutical compositions containing such compounds, and methods of using such compounds as therapeutic antihypercholesterolemic and/or antiatherosclerotic agents.

[1] This invention provides compounds of Formula I:

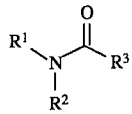

and stereoisomers and pharmaceutically acceptable salts thereof, wherein:

$R^1$ is selected from:
  phenyl substituted with 0–4 $R^{30}$,
  naphthyl substituted with 0–4 $R^{30}$;

$R^{30}$ is selected independently from: $C_1$–$C_4$ straight chain alkyl, $C_3$–$C_6$ branched alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

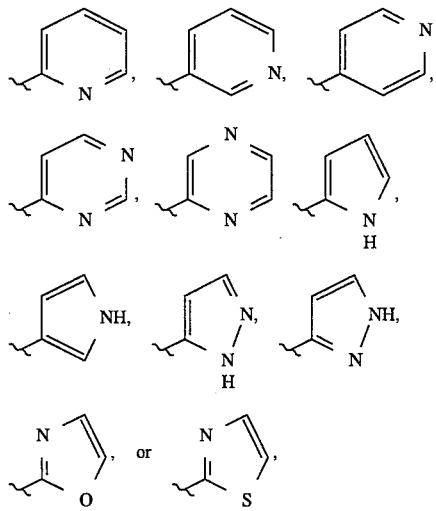

each such heterocyclic group may optionally be fused to a benzene ring, and
each such heterocyclic group and fused benzene ring may be substituted with 0–3 $R^{30}$ or phenyl, said phenyl being substituted with 0–3 $R^{30}$;

$R^1$ can also be selected from the following heterocyclic groups:

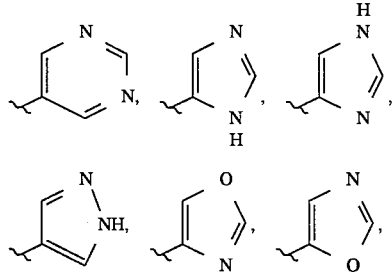

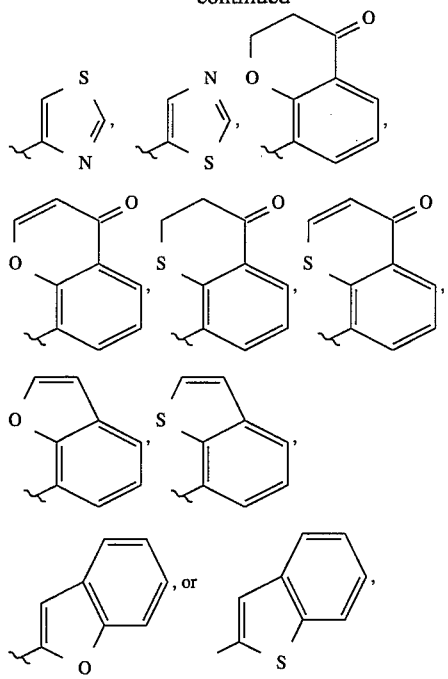

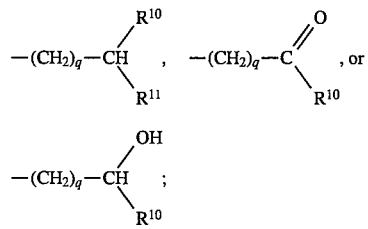

each such heterocyclic group may be substituted with 0–3 $R^{30}$ or phenyl, said phenyl being substituted with 0–3 $R^{30}$;

$R^2$ is H or $C(=O)R^{3a}$;

$R^3$ and $R^{3a}$ are independently selected from the following groups: $-CH_2-X-R^4$, $-C(R^5)(R^6)-X-R^7$, $-CF_2-R^8$, $-C(=O)R^8$, or $-C(=NR^9)R^8$;

$R^4$ is selected from:
  $C_{4-20}$ alkyl substituted with 0–6 $R^{12}$,
  $C_{5-20}$ alkenyl substituted with 0–6 $R^{12}$,
  $C_{5-20}$ alkynyl substituted with 0–6 $R^{12}$,
  $C_{4-12}$ cycloalkyl substituted with 0–6 $R^{12}$,
  $C_{5-16}$ cycloalkylalkyl substituted with 0–6 $R^{12}$,
  $C_{4-12}$ cycloalkenyl substituted with 0–6 $R^{12}$,
  $C_{6-16}$ cycloalkenylalkyl substituted with 0–6 $R^{12}$,
  $C_{6-16}$ bicycloalkylalkyl substituted with 0–6 $R^{12}$,
  $C_{8-16}$ bicycloalkenylalkyl substituted with 0–6 $R^{12}$,
  adamantyl substituted with 0–3 $R^{12}$, or $$-(CH_2)_q-\underset{R^{11}}{\overset{R^{10}}{CH}}\ ,\quad -(CH_2)_q-\underset{R^{10}}{C}\overset{O}{\diagup}\ ,\text{ or}$$

$$-(CH_2)_q-\underset{R^{10}}{\overset{OH}{CH}}\ ;$$

$R^5$ is selected from:
  aryl substituted with 0–5 $R^{13}$,
  $R^{17}$ substituted with 0–5 $R^{13}$;

$R^6$ is selected from:
  H,
  aryl substituted with 0–5 $R^{13}$,
  $R^{17}$ substituted with 0–5 $R^{13}$;

$R^7$ is selected from:
  H,
  $C_{1-20}$ alkyl substituted with 0–6 $R^{12}$,
  $C_{2-20}$ alkenyl substituted with 0–6 $R^{12}$, $C_{2-20}$ alkynyl substituted with 0–6 $R^{12}$,
$C_{3-12}$ cycloalkyl substituted with 0–6 $R^{12}$,
$C_{5-16}$ cycloalkylalkyl substituted with 0–6 $R^{12}$,
$C_{3-12}$ cycloalkenyl substituted with 0–6 $R^{12}$,
$C_{5-16}$ cycloalkenylalkyl substituted with 0–6 $R^{12}$,
$C_{6-16}$ bicycloalkyl substituted with 0–6 $R^{12}$,
$C_{6-16}$ bicycloalkenyl substituted with 0–6 $R^{12}$,
$C_{6-16}$ bicycloalkylalkyl substituted with 0–6 $R^{12}$,
$C_{8-16}$ bicycloalkenylalkyl substituted with 0–6 $R^{12}$,
aryl substituted with 0–5 $R^{13}$,
$R^{17}$ substituted with 0–5 $R^{13}$;

$R^8$ is selected from:
$C_{1-30}$ alkyl substituted with 0–6 $R^{20}$,
$C_{2-30}$ alkenyl substituted with 0–6 $R^{20}$,
$C_{2-30}$ alkynyl substituted with 0–6 $R^{20}$,
$C_{3-12}$ cycloalkyl substituted with 0–6 $R^{20}$,
$C_{3-12}$ cycloalkenyl substituted with 0–6 $R^{20}$,
$C_{6-12}$ bicycloalkyl substituted with 0–6 $R^{20}$,
$C_{6-12}$ bicycloalkenyl substituted with 0–6 $R^{12}$,
$C_{8-15}$ bicycloalkenylalkyl substituted with 0–6 $R^{12}$,
aryl substituted with 0–5 $R^{13}$,
$R^{17}$ substituted with 0–5 $R^{13}$;

$R^9$ is selected from:
$C_{1-12}$ alkyl substituted with 0–6 $R^{20}$,
$C_{2-12}$ alkenyl substituted with 0–6 $R^{20}$,
$C_{2-12}$ alkynyl substituted with 0–6 $R^{20}$,
$C_{3-12}$ cycloalkyl substituted with 0–6 $R^{20}$,
$C_{3-12}$ cycloalkenyl substituted with 0–6 $R^{20}$,
aryl substituted with 0–5 $R^{13}$,
benzyl substituted with 0–5 $R^{13}$,
$R^{17}$ substituted with 0–5 $R^{13}$, or
$OR^{16}$;

$R^{10}$ and $R^{11}$ are independently selected from:
$C_{1-10}$ alkyl substituted with 0–6 $R^{12}$,
$C_{4-12}$ cycloalkyl substituted with 0–6 $R^{12}$,
adamantyl,
aryl substituted with 0–5 $R^{13}$,
benzyl substituted with 0–5 $R^{13}$,
$R^{17}$ substituted with 0–5 $R^{13}$;

$R^{12}$ is selected from:
$R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, Br, I, $CF_3$, $OR^{14}$, $OCOR^{14}$, $OCO_2R^{14}$, $OCONR^{14}R^{15}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $CONR^{14}R^{15}$, CN, or tetrazole;

$R^{14}$ is selected from H, $C_{1-6}$ alkyl, $C_{2-6}$ alkenyl, $C_{2-6}$ alkynyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{16}$ is selected from:
$C_{1-12}$ alkyl substituted with 0–6 $R^{12}$,
$C_{2-12}$ alkenyl substituted with 0–6 $R^{12}$,
$C_{2-12}$ alkynyl substituted with 0–6 $R^{12}$,
$C_{3-12}$ cycloalkyl substituted with 0–6 $R^{12}$,
$C_{3-12}$ cycloalkenyl substituted with 0–6 $R^{12}$,
aryl substituted with 0–5 $R^{19}$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

$R^{20}$ is selected from $R^{15}$, F, Cl, Br, I, $OR^{14}$, $OCOR^{14}$, $OCO_2R^{14}$, $OCONR^{14}R^{15}$, $NO_2$, $NR^{14}R^{15}$, $S(O)_nR^{14}$, $COR^{14}$, $CO_2R^{14}$, $CONR^{14}R^{15}$, CN, tetrazole, furyl, or thienyl;

X is O or $S(O)_n$;

n is 0, 1 or 2;

q is 0–4;

with the following provisos:
(1) when $R^3$ is $-CH_2XR^4$ and $R^4$ is $-(CH_2)_qCH(R^{10})R^{11}$, then $R^1$ cannot be phenyl or substituted phenyl; and
(2) when $R^3$ is $-CH_2XR^4$, then $R^4$ cannot be straight chain alkyl.

[2] Preferred compounds of this invention are compounds of Formula I:

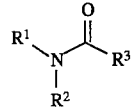

and stereoisomers and pharmaceutically acceptable salts thereof, wherein:

$R^1$ is selected from:
phenyl substituted with 0–3 $R^{30}$,
naphthyl substituted with 0–3 $R^{30}$;

$R^{30}$ is selected independently from: $C_1$–$C_4$ straight chain alkyl, $C_3$–$C_6$ branched alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

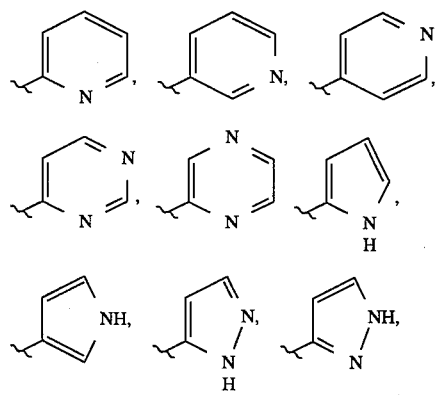

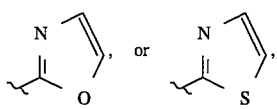

each such heterocyclic group may optionally be fused to a benzene ring, and each such heterocyclic group and fused benzene ring may be substituted with 0–3 $R^{30}$ or phenyl, said phenyl being substituted with 0–3 $R^{30}$;

$R^1$ can also be selected from the following heterocyclic groups:

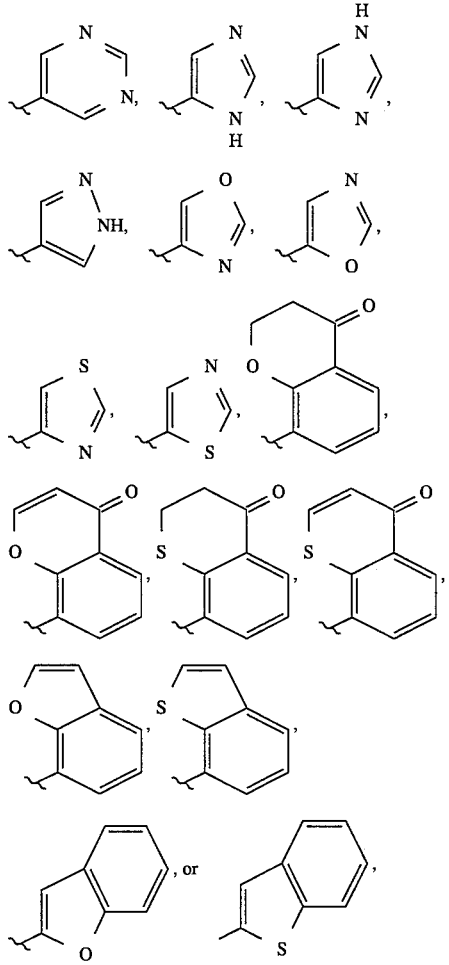

each such heterocyclic group may be substituted with 0–3 $R^{30}$ or phenyl, said phenyl being substituted with 0–3 $R^{30}$;

$R^2$ is H or $C(=O)R^{3a}$;

$R^3$ and $R^{3a}$ are independently selected from the following groups: $-CH_2-X-R^4$, $-C(R^5)(R^6)-X-R^7$, $-CF_2-R^8$, $-C(=O)R^8$, or $-C(=NR^9)R^8$;

$R^4$ is selected from:
$C_{4-20}$ alkyl substituted with 0–6 $R^{12}$,
$C_{5-20}$ alkenyl substituted with 0–6 $R^{12}$,
$C_{5-20}$ alkynyl substituted with 0–6 $R^{12}$,
$C_{4-12}$ cycloalkyl substituted with 0–6 $R^{12}$,
$C_{5-16}$ cycloalkylalkyl substituted with 0–6 $R^{12}$,
$C_{4-12}$ cycloalkenyl substituted with 0–6 $R^{12}$,
$C_{6-16}$ cycloalkenylalkyl substituted with 0–6 $R^{12}$,

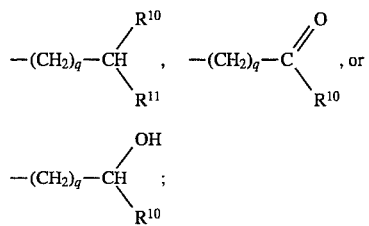

$R^5$ is selected from:
aryl substituted with 0–5 $R^{13}$,
$R^{17}$ substituted with 0–5 $R^{13}$;

$R^6$ is H;

$R^7$ is selected from:
H,
$C_{1-10}$ alkyl substituted with 0–6 $R^{12}$,
$C_{2-20}$ alkenyl substituted with 0–6 $R^{12}$,
$C_{2-20}$ alkynyl substituted with 0–6 $R^{12}$,
$C_{5-12}$ cycloalkylalkyl substituted with 0–6 $R^{12}$,
$C_{5-12}$ cycloalkenylalkyl substituted with 0–6 $R^{12}$,
aryl substituted with 0–5 $R^{13}$,
$R^{17}$ substituted with 0–5 $R^{13}$;

$R^8$ is selected from:
$C_{1-12}$ alkyl substituted with 0–6 $R^{20}$,
$C_{2-12}$ alkenyl substituted with 0–6 $R^{20}$,
$C_{3-12}$ cycloalkyl substituted with 0–6 $R^{20}$,
$C_{3-12}$ cycloalkenyl substituted with 0–6 $R^{20}$,
aryl substituted with 0–5 $R^{13}$,
$R^{17}$ substituted with 0–5 $R^{13}$;

$R^9$ is selected from:
$C_{5-12}$ alkyl substituted with 0–6 $R^{20}$,
$C_{5-12}$ alkenyl substituted with 0–6 $R^{20}$,
$C_{5-12}$ alkynyl substituted with 0–6 $R^{20}$,
$C_{3-12}$ cycloalkyl substituted with 0–6 $R^{20}$,
$C_{3-12}$ cycloalkenyl substituted with 0–6 $R^{20}$,
aryl substituted with 0–5 $R^{13}$,
benzyl substituted with 0–5 $R^{13}$,
$R^{17}$ substituted with 0–5 $R^{13}$, or
$OR^{16}$;

$R^{10}$ and $R^{11}$ are independently selected from:
$C_{1-10}$ alkyl substituted with 0–6 $R^{12}$,
$C_{4-12}$ cycloalkyl substituted with 0–6 $R^{12}$,
aryl substituted with 0–5 $R^{13}$,
benzyl substituted with 0–5 $R^{13}$,
$R^{17}$ substituted with 0–5 $R^{13}$;

$R^{12}$ is selected from:
$R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, Br, I, $CF_3$, $OR^{14}$, $OC(=O)R^{14}$, $OCO_2R^{14}$, $OC(=O)NR^{14}R^{15}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $C(=O)NR^{14}R^{15}$, CN, or tetrazole;

$R^{14}$ is selected from H, $C_{1-6}$ alkyl, $C_{2-6}$ alkenyl, $C_{2-6}$ alkynyl, or $R^{18}$;

$R^{15}$ is selected from H, $C_{1-6}$ alkyl, $C_{2-6}$ alkenyl, $C_{2-6}$ alkynyl, or $R^{18}$;

R$^{14a}$ is selected from H, C$_{1-6}$ alkyl, C$_{2-6}$ alkenyl, C$_{2-6}$ alkynyl, or aryl, said aryl being substituted with 0–3 groups selected independently from halogen, C$_1$–C$_4$ alkyl, C$_1$–C$_3$ haloalkyl, CN, C$_1$–C$_4$ alkoxy, or NO$_2$;

R$^{15a}$ is selected from H, C$_{1-6}$ alkyl, C$_{2-6}$ alkenyl, C$_{2-6}$ alkynyl, or aryl, said aryl being substituted with 0–3 groups selected independently from halogen, C$_1$–C$_4$ alkyl, C$_1$–C$_3$ haloalkyl, CN, C$_1$–C$_4$ alkoxy, or NO$_2$;

R$^{16}$ is selected from:
C$_{1-12}$ alkyl substituted with 0–6 R$^{12}$,
C$_{2-12}$ alkenyl substituted with 0–6 R$^{12}$,
C$_{2-12}$ alkynyl substituted with 0–6 R$^{12}$,
C$_{3-12}$ cycloalkyl substituted with 0–6 R$^{12}$,
C$_{3-12}$ cycloalkenyl substituted with 0–6 R$^{12}$,
aryl substituted with 0–5 R$^{19}$;

R$^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

R$^{18}$ is aryl substituted with 0–5 R$^{19}$;

R$^{19}$ is selected from C$_{1-6}$ alkyl, C$_{2-5}$ alkenyl, C$_{2-5}$ alkynyl, F, Cl, Br, I, CF$_3$, OR$^{14a}$, NO$_2$, NR$^{14a}$R$^{15a}$, S(O)$_n$R$^{14a}$, C(=O)R$^{14a}$, CO$_2$R$^{14a}$, C(=O)NR$^{14a}$R$^{15a}$, C$_1$–C$_3$ haloalkyl, or CN;

R$^{20}$ is selected from R$^{15}$, F, Cl, Br, I, OR$^{14}$, OC(=O)R$^{14}$, OCO$_2$R$^{14}$, OC(=O)NR$^{14}$R$^{15}$, NO$_2$, NR$^{14}$R$^{15}$, S(O)$_n$R$^{14}$, C(=O)R$^{14}$, CO$_2$R$^{14}$, C(=O)NR$^{14}$R$^{15}$, CN, tetrazole furyl, or thienyl;

X is O or S(O)$_n$;

n is 0, 1 or 2;

q is 0–4;

with the following provisos:
(1) when R$^3$ is —CH$_2$XR$^4$ and R$^4$ is —(CH$_2$)$_q$CH(R$^{10}$)R$^{11}$, then R$^1$ cannot be phenyl or substituted phenyl; and
(2) when R$^3$ is —CH$_2$XR$^4$, then R$^4$ cannot be straight chain alkyl.

[3] More preferred compounds of this invention are compounds of Formula I:

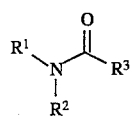

(I)

and stereoisomers and pharmaceutically acceptable salts thereof, wherein:

R$^1$ is selected from:
phenyl substituted with 0–3 R$^{30}$,
naphthyl substituted with 0–3 R$^{30}$;

R$^{30}$ is selected independently from: C$_1$–C$_4$ straight chain alkyl, C$_3$–C$_6$ branched alkyl, C$_1$–C$_4$ alkoxy, C$_1$–C$_4$ alkylthio, C$_2$–C$_8$ dialkylamino, halogen, or nitro;

R$^1$ can also be selected from the following heterocyclic groups:

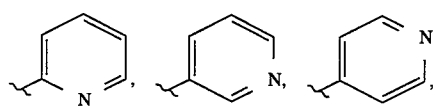

each such heterocyclic group may optionally be fused to a benzene ring, and each such heterocyclic group and each such heterocyclic group fused to a benzene ring may be substituted with 0–2 R$^{30}$ or phenyl, said phenyl being substituted with 0–2 R$^{30}$;

R$^1$ can also be selected from the following heterocyclic groups:

each such heterocyclic group may be substituted with 0–2 R$^{30}$ or phenyl, said phenyl being substituted with 0–2 R$^{30}$;

R$^2$ is H or C(=O)R$^{3a}$;

R$^3$ and R$^{3a}$ are independently selected from the following groups: —CH$_2$—X—R$^4$, —CH(R$^5$)—X—R$^7$, —CF$_2$—R$^8$, —C(=O)R$^8$, or —C(=NR$^9$)R$^8$;

R$^4$ is selected from:
C$_{4-20}$ alkyl substituted with 0–4 R$^{12}$,
C$_{5-20}$ alkenyl substituted with 0–4 R$^{12}$,
—(CH$_2$)$_q$—CH(R$^{10}$)R$^{11}$;

R$^5$ is selected from:

aryl substituted with 0–3 $R^{13}$,
$R^{17}$ substituted with 0–3 $R^{13}$;

$R^7$ is selected from:
H,
$C_{1-10}$ alkyl substituted with 0–4 $R^{12}$,
$C_{2-20}$ alkenyl substituted with 0–4 $R^{12}$,
$C_{5-12}$ cycloalkylalkyl substituted with 0–4 $R^{12}$,
aryl substituted with 0–3 $R^{13}$,
$R^{17}$ substituted with 0–3 $R^{13}$;

$R^8$ is selected from:
$C_{1-12}$ alkyl substituted with 0–4 $R^{20}$,
$C_{2-12}$ alkenyl substituted with 0–4 $R^{20}$,
$C_{3-12}$ cycloalkyl substituted with 0–4 $R^{20}$,
$C_{3-12}$ cycloalkenyl substituted with 0–4 $R^{20}$,
aryl substituted with 0–3 $R^{13}$,
$R^{17}$ substituted with 0–3 $R^{13}$;

$R^9$ is selected from:
$C_{5-10}$ alkyl substituted with 0–6 $R^{20}$,
$C_{5-10}$ cycloalkyl substituted with 0–6 $R^{20}$,
$C_{5-10}$ cycloalkenyl substituted with 0–6 $R^{20}$,
aryl substituted with 0–5 $R^{13}$,
benzyl substituted with 0–5 $R^{13}$,
$R^{17}$ substituted with 0–5 $R^{13}$, or
$OR^{16}$;

$R^{10}$ and $R^{11}$ are independently selected from:
$C_{1-10}$ alkyl substituted with 0–4 $R^{12}$,
$C_{4-12}$ cycloalkyl substituted with 0–4 $R^{12}$,
aryl substituted with 0–3 $R^{13}$,
benzyl substituted with 0–3 $R^{13}$,
$R^{17}$ substituted with 0–3 $R^{13}$;

$R^{12}$ is selected from:
$R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $NO_2$, $N(R^{14})R^{15}$, $S(O)_nR^{14}$, $C(=O)R^{14}$, $CO_2R^{14}$, $C(=O)N(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–4 $R^{12}$,
F, Cl, Br, I, $CF_3$, $OR^{14}$, $OC(=O)R^{14}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$,
$C(=O)R^{14}$, $CO_2R^{14}$, $C(=O)NR^{14}R^{15}$, CN, or tetrazole;

$R^{14}$ is selected from H, $C_{1-6}$ alkyl, or $R^{18}$;

$R^{15}$ is selected from H, $C_{1-6}$ alkyl, $C_{2-6}$ alkenyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{16}$ is selected from:
$C_{1-6}$ alkyl substituted with 0–4 $R^{12}$,
$C_{2-6}$ alkenyl substituted with 0–4 $R^{12}$,
aryl substituted with 0–3 $R^{19}$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

$R^{20}$ is selected from $R^{15}$, F, Cl, Br, I, $OR^{14}$, $OC(=O)R^{14}$, $OCO_2R^{14}$, $OC(=O)NR^{14}R^{15}$, $NO_2$, $NR^{14}R^{15}$, $S(O)_nR^{14}$, $C(=O)R^{14}$, $CO_2R^{14}$, $C(=O)NR^{14}R^{15}$, CN, tetrazole furyl, or thienyl;

X is O or $S(O)_n$;

n is 0, 1 or 2;

q is 0–4;

with the following provisos:
(1) when $R^3$ is —$CH_2XR^4$ and $R^4$ is —$(CH_2)_qCH(R^{10})R^{11}$, then $R^1$ cannot be phenyl or substituted phenyl; and (2) when $R^3$ is —$CH_2XR^4$, then $R^4$ cannot be straight chain alkyl.

[4] Preferred compounds of a first embodiment of this invention are those compounds of Formula I:

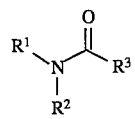

and stereoisomers and pharmaceutically acceptable salts thereof, wherein:

$R^1$ is selected from:
phenyl substituted with 0–3 $R^{30}$,
naphthyl substituted with 0–3 $R^{30}$;

$R^{30}$ is selected independently from: $C_1$–$C_4$ straight chain alkyl, $C_3$–$C_6$ branched alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

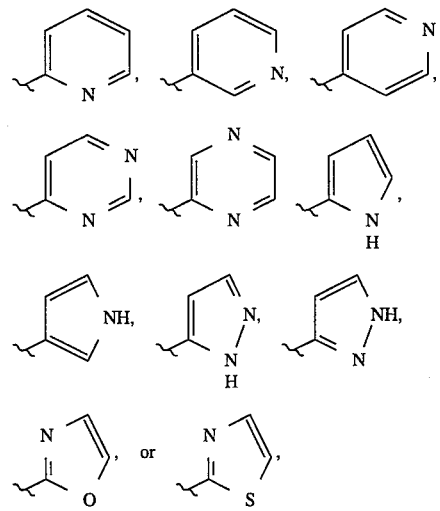

each such heterocyclic group may optionally be fused to a benzene ring, and
each such heterocyclic group and fused benzene ring may be substituted with 0–3 $R^{30}$ or phenyl, said phenyl being substituted with 0–3 $R^{30}$;

$R^1$ can also be selected from the following heterocyclic groups:

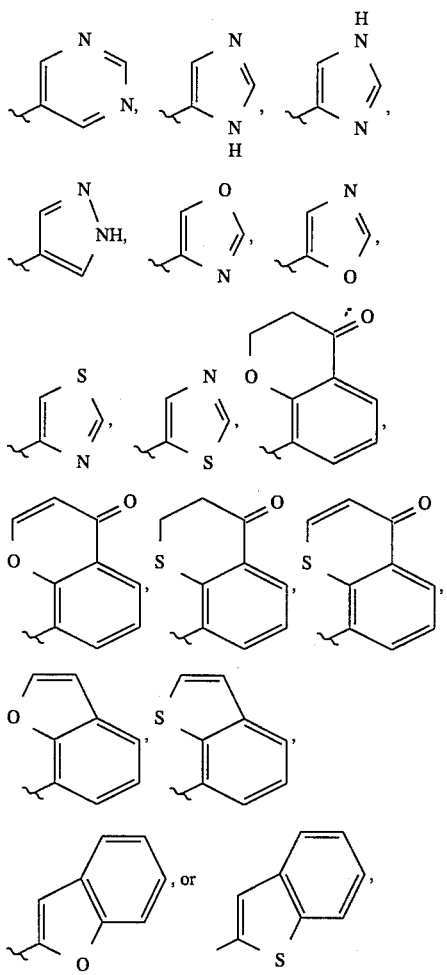

each such heterocyclic group may be substituted with 0–3 $R^{30}$ or phenyl, said phenyl being substituted with 0–3 $R^{30}$;

$R^2$ is H;

$R^3$ is —$CH_2$—X—$R^4$;

$R^4$ is selected from:
$C_{4-20}$ alkyl substituted with 0–6 $R^{12}$,
$C_{5-20}$ alkenyl substituted with 0–6 $R^{12}$,
$C_{5-20}$ alkynyl substituted with 0–6 $R^{12}$,
$C_{4-12}$ cycloalkyl substituted with 0–6 $R^{12}$,
$C_{5-16}$ cycloalkylalkyl substituted with 0–6 $R^{12}$,
$C_{4-12}$ cycloalkenyl substituted with 0–6 $R^{12}$,
$C_{6-16}$ cycloalkenylalkyl substituted with 0–6 $R^{12}$,
$C_{6-16}$ bicycloalkylalkyl substituted with 0–6 $R^{12}$,
$C_{8-16}$ bicycloalkenylalkyl substituted with 0–6 $R^{12}$,
adamantyl substituted with 0–3 $R^{12}$, or

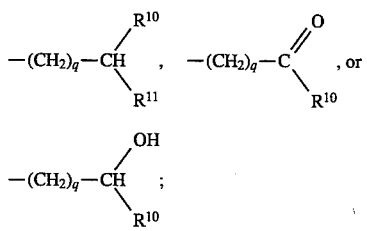

$R^{10}$ and $R^{11}$ are independently selected from:
$C_{1-10}$ alkyl substituted with 0–6 $R^{12}$,
$C_{4-12}$ cycloalkyl substituted with 0–6 $R^{12}$,
adamantyl,
aryl substituted with 0–5 $R^{13}$,
benzyl substituted with 0–5 $R^{13}$,
$R^{17}$ substituted with 0–5 $R^{13}$;

$R^{12}$ is selected from:
$R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, Br, I, $CF_3$, $OR^{14}$, $OCOR^{14}$, $OCO_2R^{14}$, $OCONR^{14}$, $R^{15}$, $NO_2$, $NR^{14}R^{15}$, $NR^{14}SO_2R^{15}$, $NR^{14}SO_2CF_3$,
$SR^{14}$, $S(=O)R^{14}$, $S(=O)_2R^{14}$, $C(=O)R^{14}$, $CO_2R^{14}$, $CONR^{14}R^{15}$, CN, or tetrazole;

$R^{14}$ is selected from H, $C_{1-6}$ alkyl, $C_{2-6}$ alkenyl, $C_{2-6}$ alkynyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

X is O or $S(O)_n$;

n is 0, 1 or 2;

q is 0–4;

with the following provisos:
(1) when $R^4$ is —$(CH_2)_qCH(R^{10})R^{11}$, then $R^1$ cannot be phenyl or substituted phenyl; and
(2) $R^4$ cannot be straight chain alkyl.

[5] More preferred compounds of this first embodiment of this invention are compounds of Formula I:

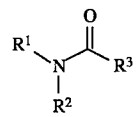

(I)

and stereoisomers and pharmaceutically acceptable salts thereof, wherein:

$R^1$ is selected from:
phenyl substituted with 0–3 $R^{30}$,
naphthyl substituted with 0–3 $R^{30}$;

$R^{30}$ is selected independently from: $C_1$–$C_4$ straight chain alkyl, $C_3$–$C_6$ branched alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

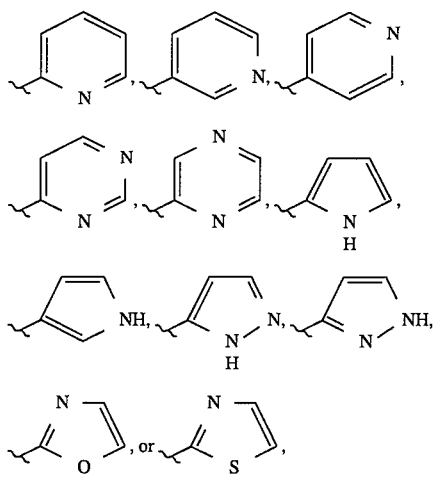

each such heterocyclic group may optionally be fused to a benzene ring, and
each such heterocyclic group and fused benzene ring may be substituted with 0–3 $R^{30}$ or phenyl, said phenyl being substituted with 0–3 $R^{30}$;

$R^1$ can also be selected from the following heterocyclic groups:

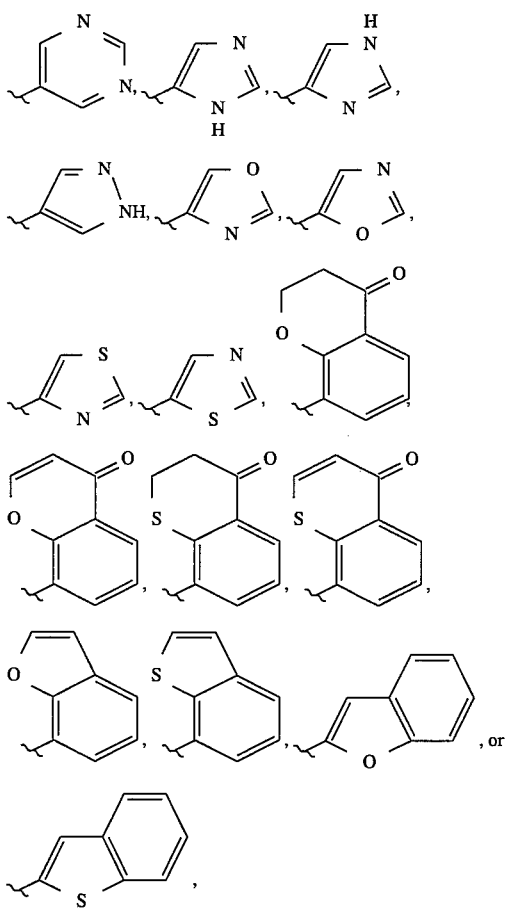

each such heterocyclic group may be substituted with 0–3 $R^{30}$ or phenyl, said phenyl being substituted with 0–3 $R^{30}$;

$R^2$ is H;

$R^3$ is —$CH_2$—X—$R^4$;

$R^4$ is selected from:
- $C_{4-20}$ alkyl substituted with 0–6 $R^{12}$,
- $C_{5-20}$ alkenyl substituted with 0–6 $R^{12}$,
- $C_{5-20}$ alkynyl substituted with 0–6 $R^{12}$,
- $C_{4-12}$ cycloalkyl substituted with 0–6 $R^{12}$,
- $C_{5-16}$ cycloalkylalkyl substituted with 0–6 $R^{12}$,
- $C_{4-12}$ cycloalkenyl substituted with 0–6 $R^{12}$,
- $C_{6-16}$ cycloalkenylalkyl substituted with 0–6 $R^{12}$,

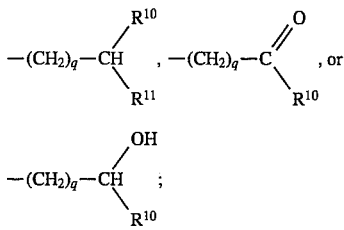

$R^{10}$ and $R^{11}$ are independently selected from:
- $C_{1-10}$ alkyl substituted with 0–6 $R^{12}$,
- $C_{4-12}$ cycloalkyl substituted with 0–6 $R^{12}$,
- aryl substituted wish 0–5 $R^{13}$,
- benzyl substituted with 0–5 $R^{13}$,
- $R^{17}$ substituted with 0–5 $R^{13}$;

$R^{12}$ is selected from:
$R^{17}$, $OR^{17}$, $SR^{17}$, $NHR^{17}$, $R^{18}$, $OR^{18}$ $SR^{18}$ $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, Br, I, $CF_3$, $OR^{14}$, $OC(=O)R^{14}$, $OCO_2R^{14}$, $OC(=O)NR^{14}R^{15}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $C(=O)NR^{14}R^{15}$, CN, or tetrazole;

$R^{14}$ is selected from H, $C_{1-6}$ alkyl, $C_{2-6}$ alkenyl, $C_{2-6}$ alkynyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

X is O or $S(O)_n$;

n is 0, 1 or 2;
q is 0–4;
with the following provisos:
(1) when $R^3$ is —$CH_2XR^4$ and $R^4$ is —$(CH_2)_qCH(R^{10})R^{11}$, then $R^1$ cannot be phenyl or substituted phenyl; and
(2) when $R^3$ is —$CH_2XR^4$, then $R^4$ cannot be straight chain alkyl.

[6] Still more preferred compounds of this first embodiment of this invention are compounds of Formula I:

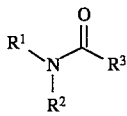
(I)

and stereoisomers and pharmaceutically acceptable salts thereof, wherein:

$R^1$ is selected from:
  phenyl substituted with 0–3 $R^{30}$,
  naphthyl substituted with 0–3 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

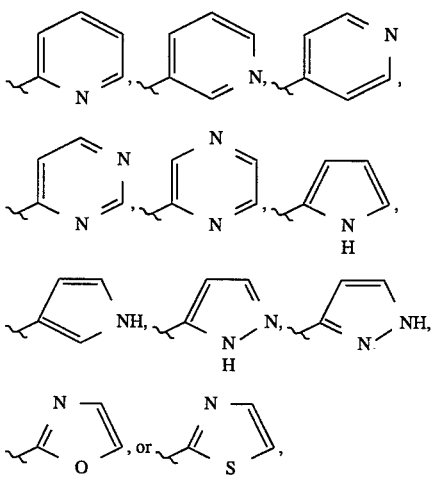

each such heterocyclic group may optionally be fused to a benzene ring, and
each such heterocyclic group and each such heterocyclic group fused to a benzene ring may be substituted with 0–2 $R^{30}$ or phenyl, said phenyl being substituted with 0–2 $R^{30}$;

$R^1$ can also be selected from the following heterocyclic groups:

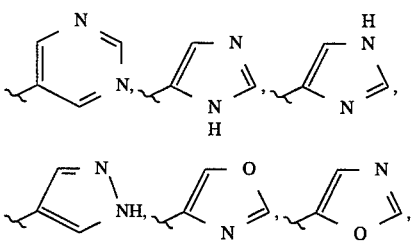

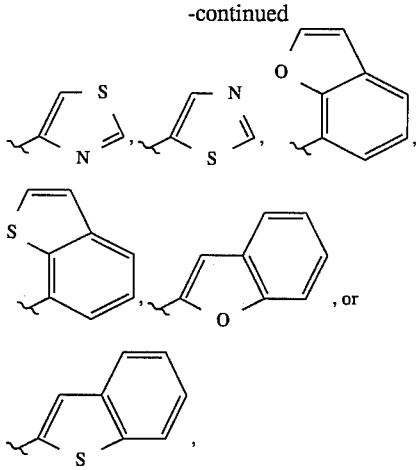

each such heterocyclic group may be substituted with 0–2 $R^{30}$ or phenyl, said phenyl being substituted with 0–2 $R^{30}$;

$R^2$ is H;

$R^3$ is —$CH_2$—$X$—$R^4$;

$R^4$ is selected from:
  $C_{4-20}$ alkyl substituted with 0–4 $R^{12}$,
  $C_{5-20}$ alkenyl substituted with 0–4 $R^{12}$,
  —$(CH_2)_q$—$CH(R^{10})R^{11}$;

$R^{10}$ and $R^{11}$ are independently selected from:
  $C_{1-10}$ alkyl substituted with 0–4 $R^{12}$,
  $C_{4-12}$ cycloalkyl substituted with 0–4 $R^{12}$,
  aryl substituted with 0–3 $R^{13}$,
  benzyl substituted with 0–3 $R^{13}$,
  $R^{17}$ substituted with 0–3 $R^{13}$;

$R^{12}$ is selected from:
  $R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $NO_2$, $N(R^{14})R^{15}$, $S(O)_nR^{14}$, $C(=O)R^{14}$, $CO_2R^{14}$, $C(=O)N(R^{14})R^{15}$, CN, or tetrazole;

$R^{13}$ is selected from:
  $R^{18}$, $OR^{18}$, $SR^{18}$, $NHR^{18}$,
  $C_{1-8}$ alkyl substituted with 0–4 $R^{12}$,
  F, Cl, Br, I, $CF_3$, $OR^{14}$, $OC(=O)R^{14}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $C(=O)NR^{14}R^{15}$, CN, or tetrazole;

$R^{14}$ is selected from H, $C_{1-6}$ alkyl, or $R^{18}$;

$R^{15}$ is selected from H, $C_{1-6}$ alkyl, $C_{2-6}$ alkenyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

X is O or $S(O)_n$;
n is 0, 1 or 2;
q is 0–4;
with the following provisos:
(1) when $R^4$ is $-(CH_2)_qCH(R^{10})R^{11}$, then $R^1$ cannot be phenyl or substituted phenyl; and
(2) $R^4$ cannot be straight chain alkyl.

[7] Preferred compounds of this invention are compounds of a second embodiment of the invention of Formula I:

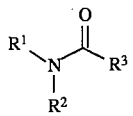

(I)

and stereoisomers and pharmaceutically acceptable salts thereof, wherein:

$R^1$ is selected from:
  phenyl substituted with 0–3 $R^{30}$,
  naphthyl substituted with 0–3 $R^{30}$;

$R^{30}$ is selected independently from: $C_1$–$C_4$ straight chain alkyl, $C_3$–$C_6$ branched alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

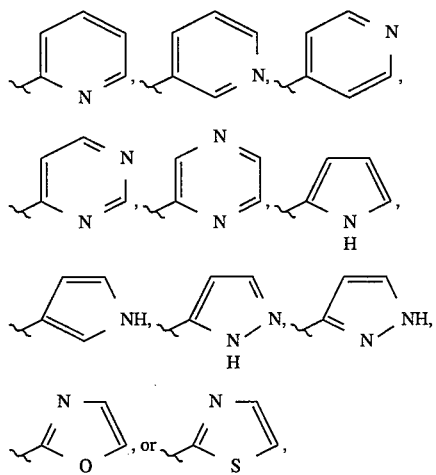

each such heterocyclic group may optionally be fused to a benzene ring, and
each such heterocyclic group and fused benzene ring may be substituted with 0–3 $R^{30}$ or phenyl, said phenyl being substituted with 0–3 $R^{30}$;

$R^1$ can also be selected from the following heterocyclic groups:

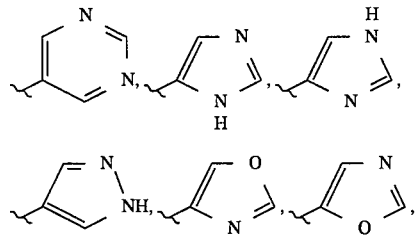

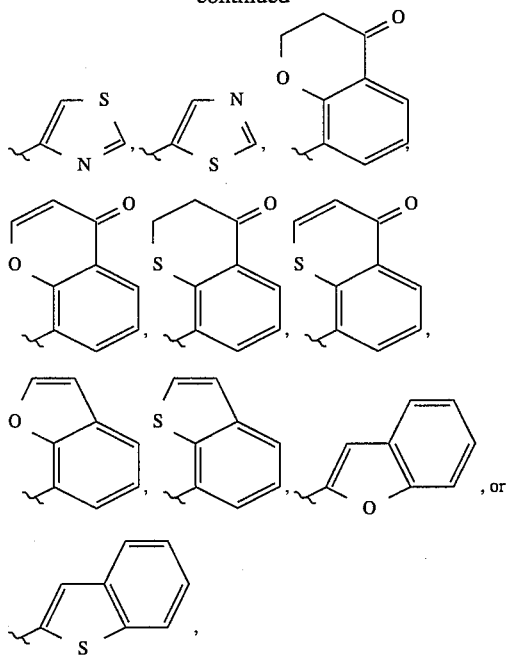

each such heterocyclic group may be substituted with 0–3 $R^{30}$ or phenyl, said phenyl being substituted with 0–3 $R^{30}$;

$R^2$ is H;
$R^3$ is $-C(R^5)(R^6)-X-R^7$;
$R^5$ is selected from:
  aryl substituted with 0–5 $R^{13}$,
  $R^{17}$ substituted with 0–5 $R^{13}$;

$R^6$ is selected from:
  H,
  aryl substituted with 0–5 $R^{13}$,
  $R^{17}$ substituted with 0–5 $R^{13}$;

$R^7$ is selected from:
  H,
  $C_{1-20}$ alkyl substituted with 0–6 $R^{12}$,
  $C_{2-20}$ alkenyl substituted with 0–6 $R^{12}$,
  $C_{2-20}$ alkynyl substituted with 0–6 $R^{12}$,
  $C_{3-12}$ cycloalkyl substituted with 0–6 $R^{12}$,
  $C_{5-16}$ cycloalkylalkyl substituted with 0–6 $R^{12}$,
  $C_{3-12}$ cycloalkenyl substituted with 0–6 $R^{12}$,
  $C_{5-16}$ cycloalkenylalkyl substituted with 0–6 $R^{12}$,
  $C_{6-16}$ bicycloalkyl substituted with 0–6 $R^{12}$,
  $C_{6-16}$ bicycloalkenyl substituted with 0–6 $R^{12}$,
  $C_{6-16}$ bicycloalkylalkyl substituted with 0–6 $R^{12}$,
  $C_{8-16}$ bicycloalkenylalkyl substituted with 0–6 $R^{12}$,
  aryl substituted with 0–5 $R^{13}$,
  $R^{17}$ substituted with 0–5 $R^{13}$;

$R^{12}$ is selected from:
  $R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:
  $R^{18}$, $OR^{18}$, $SR^{18}$, $NHR^{18}$,
  $C_{1-8}$ alkyl substituted with 0–6 $R^{12}$,
  $C_{2-8}$ alkenyl substituted with 0–6 $R^{12}$,
  $C_{2-8}$ alkynyl substituted with 0–6 $R^{12}$,
  F, Cl, Br, I, $CF_3$, $OR^{14}$, $OCOR^{14}$, $OCO_2R^{14}$, $OCONR^{14}R^{15}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $CONR^{14}R^{15}$, CN, or tetrazole;

$R^{14}$ is selected from H, $C_{1-6}$ alkyl, $C_{2-6}$ alkenyl, $C_{2-6}$ alkynyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

X is O or $S(O)_n$;

n is 0, 1 or 2.

[8] More preferred compounds of this second embodiment of this invention are compounds of Formula I:

$$R^1\text{-N}(R^2)\text{-C}(=O)\text{-}R^3 \quad (I)$$

and stereoisomers and pharmaceutically acceptable salts thereof, wherein:

$R^1$ is selected from:
  phenyl substituted with 0–3 $R^{30}$,
  naphthyl substituted with 0–3 $R^{30}$;

$R^{30}$ is selected independently from: $C_1$–$C_4$ straight chain alkyl, $C_3$–$C_6$ branched alkyl, $C_3$–$C_8$ cycloalkyl, $C_4$–$C_9$ cycloalkylalkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

[heterocyclic structures shown]

each such heterocyclic group may optionally be fused to a benzene ring, and each such heterocyclic group and fused benzene ring may be substituted with 0–3 $R^{30}$ or phenyl, said phenyl being substituted with 0–3 $R^{30}$;

$R^1$ can also be selected from the following heterocyclic groups:

[heterocyclic structures shown]

each such heterocyclic group may be substituted with 0–3 $R^{30}$ or phenyl, said phenyl being substituted with 0–3 $R^{30}$;

$R^2$ is H;

$R^3$ is $-C(R^5)(R^6)-X-R^7$;

$R^5$ is selected from:
  aryl substituted with 0–5 $R^{13}$,
  $R^{17}$ substituted with 0–5 $R^{13}$;

$R^6$ is H, $R^7$ is selected from:
  H,
  $C_{1-10}$ alkyl substituted with 0–6 $R^{12}$,
  $C_{2-20}$ alkenyl substituted with 0–6 $R^{12}$,
  $C_{2-20}$ alkynyl substituted with 0–6 $R^{12}$,
  $C_{5-12}$ cycloalkylalkyl substituted with 0–6 $R^{12}$,
  $C_{5-12}$ cycloalkenylalkyl substituted with 0–6 $R^{12}$,
  aryl substituted with 0–5 $R^{13}$,
  $R^{17}$ substituted with 0–5 $R^{13}$;

$R^{12}$ is selected from:
  $R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:

$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, Br, I, $CF_3$, $OR^{14}$, $OC(=O)R^{14}$, $OCO_2R^{14}$, $OC(=O)NR^{14}R^{15}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $C(=O)NR^{14}R^{15}$, CN, or tetrazole;

$R^{14}$ is selected from H, $C_{1-6}$ alkyl, $C_{2-6}$ alkenyl, $C_{2-6}$ alkynyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

X is O or $S(O)_n$;

n is 0, 1 or 2.

[9] Still more preferred compounds of this second embodiment of this invention are compounds of Formula I:

(I)

and stereoisomers and pharmaceutically acceptable salts thereof, wherein:

$R^1$ is selected from:
phenyl substituted with 0–3 $R^{30}$,
naphthyl substituted with 0–3 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

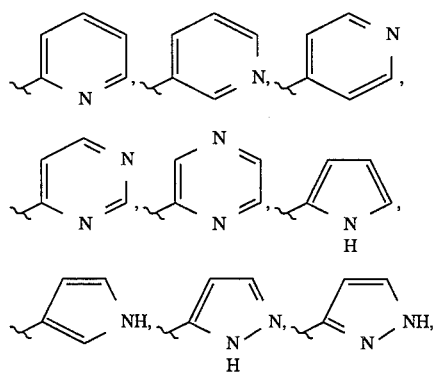

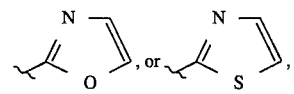

each such heterocyclic group may optionally be fused to a benzene ring, and
each such heterocyclic group and each such heterocyclic group fused to a benzene ring may be substituted with 0–2 $R^{30}$ or phenyl, said phenyl being substituted with 0–2 $R^{30}$;

$R^1$ can also be selected from the following heterocyclic groups:

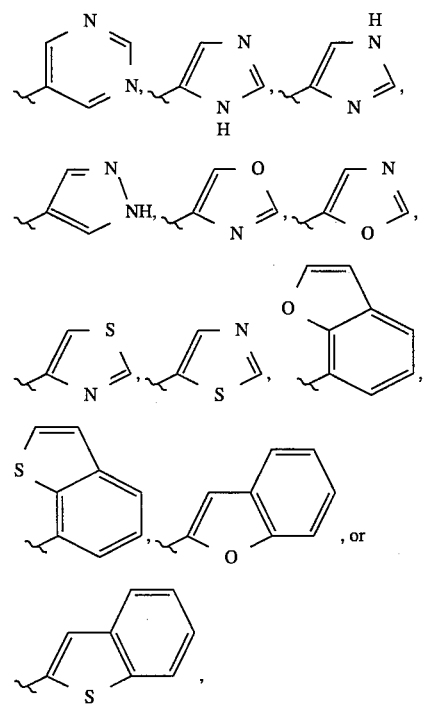

each such heterocyclic group may be substituted with 0–2 $R^{30}$ or phenyl, said phenyl being substituted with 0–2 $R^{30}$;

$R^2$ is H;

$R^3$ —CH($R^5$)—X—$R^7$;

$R^5$ is selected from:
aryl substituted with 0–3 $R^{13}$,
$R^{17}$ substituted with 0–3 $R^{13}$;

$R^7$ is selected from:
H,
$C_{1-10}$ alkyl substituted with 0–4 $R^{12}$,
$C_{2-20}$ alkenyl substituted with 0–4 $R^{12}$,
$C_{5-12}$ cycloalkylalkyl substituted with 0–4 $R^{12}$,
aryl substituted with 0–3 $R^{13}$,
$R^{17}$ substituted with 0–3 $R^{13}$;

$R^{12}$ is selected from:
$R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $NO_2$, $N(R^{14})R^{15}$, $S(O)_nR^{14}$, $C(=O)R^{14}$, $CO_2R^{14}$, $C(=O)N(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–4 $R^{12}$,
F, Cl, Br, I, $CF_3$, $OR^{14}$, $OC(=O)R^{14}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$,
$C(=O)R^{14}$, $CO_2R^{14}$, $C(=O)NR^{14}R^{15}$, CN, or tetrazole;

$R^{14}$ is selected from H, $C_{1-6}$ alkyl, or $R^{18}$;

$R^{15}$ is selected from H, $C_{1-6}$ alkyl, $C_{2-6}$ alkenyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, or pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

X is O or $S(O)_n$;

n is 0, 1 or 2.

[10] Preferred compounds of this invention are compounds of a third embodiment of this invention of Formula I:

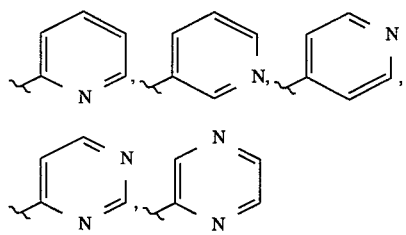

(I)

and stereoisomers and pharmaceutically acceptable salts thereof, wherein:

$R^1$ is selected from:
phenyl substituted with 0–3 $R^{30}$,
naphthyl substituted with 0–3 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

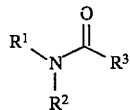

each such heterocyclic group may optionally be fused to a benzene ring, and
each such heterocyclic group and fused benzene ring may be substituted with 0–3 $R^{30}$ or phenyl, said phenyl being substituted with 0–3 $R^{30}$;

$R^1$ can also be the following heterocyclic group:

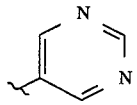

said heterocyclic group may be substituted with 0–3 $R^{30}$ or phenyl, said phenyl being substituted with 0–3 $R^{30}$;

$R^2$ is H or $C(=O)R^{3a}$;

$R^3$ and $R^{3a}$ are independently selected from the following groups: $—CF_2—R^8$, $—C(=O)R^8$, or $—C(=NR^9)R^8$;

$R^8$ is selected from:
$C_{6-12}$ alkyl substituted with 0–3 $R^{20}$,
$C_{6-12}$ alkenyl substituted with 0–3 $R^{20}$,
$C_{6-12}$ alkynyl substituted with 0–3 $R^{20}$,
$C_{3-12}$ cycloalkyl substituted with 0–3 $R^{20}$,
$C_{3-12}$ cycloalkenyl substituted with 0–3 $R^{20}$,
aryl substituted with 0–3 $R^{13}$;

$R^9$ is selected from:
$C_{5-10}$ alkyl substituted with 0–6 $R^{20}$,
$C_{5-10}$ cycloalkyl substituted with 0–6 $R^{20}$,
$C_{5-10}$ cycloalkenyl substituted with 0–6 $R^{20}$,
aryl substituted with 0–5 $R^{13}$,
benzyl substituted with 0–5 $R^{13}$,
$R^{17}$ substituted with 0–5 $R^{13}$, or
$OR_{16}$;

$R^{12}$ is selected from:
$R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, or tetrazole;

$R^{13}$ is selected from:
$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, Br, I, $CF_3$, $OR^{14}$, $OCOR^{14}$, $OCO_2R^{14}$, $OCONR^{14}R^{15}$, $NO_2$, $NR^{14}R^{15}$, $NR^{14}SO_2R^{15}$, $NR^{14}SO_2CF_3$, $SR^{14}$, $S(=O)R^{14}$, $S(=O)_2R^{14}$, $C(=O)R^{14}$, $CO_2R^{14}$, $CONR^{14}R^{15}$, CN, or tetrazole;

$R^{14}$ is selected from H, $C_{1-6}$ alkyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{16}$ is selected from:
$C_{1-6}$ alkyl substituted with 0–3 $R^{12}$,
$C_{2-6}$ alkenyl substituted with 0–3 $R^{12}$,
aryl substituted with 0–3 $R^{19}$;

$R^{18}$ is aryl substituted with 0–3 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

$R^{20}$ is selected from $R^{18}$, F, Cl, Br, I $OR^{14}$, $OCOR^{14}$, $OCO_2R^{14}$, $OCONR^{14}R^{15}$, $NO_2$, $S(O)_nR^{14}$, $COR^{14}$, $CO_2R^{14}$, $CONR^{14}R^{15}$, CN, furyl, or thienyl;

n is 0, 1 or 2.

[11] More preferred compounds of the third embodiment of this invention are compounds of Formula I:

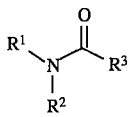

(I)

and stereoisomers and pharmaceutically acceptable salts thereof, wherein:

$R^1$ is selected from:
  phenyl substituted with 0–3 $R^{30}$,
  naphthyl substituted with 0–3 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, or nitro;

$R^1$ can also be selected from the following heterocyclic groups:

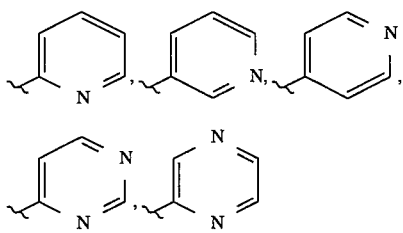

each such heterocyclic group may optionally be fused to a benzene ring, and
each such heterocyclic group and fused benzene ring may be substituted with 0–3 $R^{30}$ or phenyl, said phenyl being substituted with 0–3 $R^{30}$;

$R^1$ can also be the following heterocyclic group:

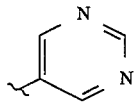

said heterocyclic group may be substituted with 0–3 $R^{30}$ or phenyl, said phenyl being substituted with 0–3 $R^{30}$;

$R^2$ is H or $C(=O)R^{3a}$;

$R^3$ and $R^{3a}$ are independently selected from the following groups: —$CF_2$—$R^8$, —$C(=O)R^8$, or —$C(=NR^9)R^8$;

$R^8$ is selected from:
  $C_{6-10}$ alkyl substituted with 0–3 $R^{20}$,
  $C_{5-8}$ cycloalkyl substituted with 0–3 $R^{20}$,
  aryl substituted with 0–3 $R^{13}$;

$R^9$ is selected from:
  $C_{5-10}$ alkyl substituted with 0–6 $R^{20}$,
  $C_{5-10}$ cycloalkyl substituted with 0–6 $R^{20}$,
  $C_{5-10}$ cycloalkenyl substituted with 0–6 $R^{20}$,
  aryl substituted with 0–5 $R^{13}$,
  benzyl substituted with 0–5 $R^{13}$,
  $R^{17}$ substituted with 0–5 $R^{13}$ or
  $OR^{16}$;

$R^{12}$ is selected from:
  $R^{18}$, $OR^{18}$, $SR^{18}$, $NHR^{18}$, F, Cl, Br, I, $OR^{14}$,
  $OC(=O)R^{14}$, $OCO_2R^{14}$, $OC(=O)N(R^{14})R^{15}$, $NO_2$,
  $N(R^{14})R^{15}$, $S(O)_nR^{14}$, $C(=O)R^{14}$, $CO_2R^{14}$,
  $CON(R^{14})R^{15}$, CN, or tetrazole;

$R^{13}$ is selected from:
  $R^{18}$, $OR^{18}$, $SR^{18}$, $NHR^{18}$,
  $C_{1-8}$ alkyl substituted with 0–6 $R^{12}$,
  $C_{2-8}$ alkenyl substituted with 0–6 $R^{12}$,
  $C_{2-8}$ alkynyl substituted with 0–6 $R^{12}$,
  F, Cl, Br, I, $CF_3$, $OR^{14}$, $OCOR^{14}$, $OCO_2R^{14}$,
  $OCONR^{14}R^{15}$, $NO_2$, $NR^{14}R^{15}$, $NR^{14}SO_2R^{15}$,
  $NR^{14}SO_2CF_3$,
  $SR^{14}$, $S(=O)R^{14}$, $S(=O)_2R^{14}$, $C(=O)R^{14}$, $CO_2R^{14}$,
  $CONR^{14}R^{15}$, CN, or tetrazole;

$R^{14}$ is selected from H, $C_{1-6}$ alkyl, or $R^{18}$;

$R^{15}$ is selected from H, $C_{1-6}$ alkyl, $C_{2-6}$ alkenyl, $C_{2-6}$ alkynyl, or $R^{18}$;

$R^{14a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{15a}$ is selected from H, $C_{1-6}$ alkyl, $C_{2-6}$ alkenyl, $C_{2-6}$ alkynyl, or aryl, said aryl being substituted with 0–3 groups selected independently from halogen, $C_1$–$C_4$ alkyl, $C_1$–$C_3$ haloalkyl, CN, $C_1$–$C_4$ alkoxy, or $NO_2$;

$R^{16}$ is selected from:
  $C_{1-6}$ alkyl substituted with 0–3 $R^{12}$,
  $C_{2-6}$ alkenyl substituted with 0–3 $R^{12}$,
  aryl substituted with 0–3 $R^{19}$;

$R^{18}$ is aryl substituted with 0–3 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, or CN;

$R^{20}$ is selected from $R^{18}$, F, Cl, Br, I, $OR^{14}$, $OCOR^{14}$, $OCO_2R^{14}$, $OCONR^{14}R^{15}$, $NO_2$, $S(O)_nR^{14}$, $COR^{14}$, $CO_2R^{14}$, $CONR^{14}R^{15}$, CN, furyl, or thienyl;

n is 0, 1 or 2.

Specifically preferred compounds of this invention are compounds of Formula I, and stereoisomers and pharmaceutically acceptable salts thereof, selected from the following compounds:

N-[2,4-bis(methylthio)-6-methyl-3-pyridyl]-D-(−)-α-O-hexyl-mandeloamide;
N-[2,4-bis(methylthio)-6-methyl-3-pyridyl]-L-(+)-α-O-hexyl-mandeloamide;
N-[2,4-bis(methylthio)-6-methyl-3-pyridyl]-L-(+)-α-O-benzyl-mandeloamide;
N-[2,4-bis(methylthio)-6-methyl-3-pyridyl]-D-(−)-α-hexylthio-phenylacetamide;
N-[2,4-bis(methylthio)-6-methyl-3-pyridyl]-L-(+)-α-hexylthio-phenylacetamide;
N-(2,6-diisopropyl-phenyl)-D-(−)-α-hexylthio-phenylacetamide;
N-[2,4-bis(methylthio)-6-methyl-3-pyridyl]-D-(−)-α-benzylthio-phenylacetamide;
N-[2,4-bis(methylthio)-6-methyl-3-pyridyl]-L-(+)-α-benzylthio-phenylacetamide;
N-(2,6-diisopropyl-phenyl)-D-(−)-α-benzylthio-phenylacetamide;
N-[2,4-bis(methylthio)-6-methyl-3-pyridyl]-D-(−)-α-ethylthio-phenylacetamide;
N-[2,4-bis(methylthio)-6-methyl-3-pyridyl]-L-(+)-α-ethylthio-phenylacetamide;
N-[2,4-bis(methylthio)-6-methyl-3-pyridyl]-L-(+)-α-phenylthio-phenylacetamide;
N-(2,6-diisopropyl-phenyl)-D-(−)-α-benzylthio-phenylacetamide;
N-[2,4-bis(methylthio)-6-methyl-3-pyridyl]-α-hexylthio-4-chloro-phenylacetamide;

N-[2,4-bis(methylthio)-6-methyl-3-pyridyl]-α-benzylthio-4-chloro-phenylacetamide;
N-[2,4-bis(methylthio)-6-methyl-3-pyridyl]-α-(4-methoxybenzylthio)-4-chloro-phenylacetamide;
N-[2,4-bis(methylthio)-6-methyl-3-pyridyl]-α-(4-fluorobenzylthio)-4-chloro-phenylacetamide;
N-[2,4-bis(methylthio)-6-methyl-3-pyridyl]-α-(4-chlorobenzylthio)-4-chloro-phenylacetamide;
N-[2,4-bis(methylthio)-6-methyl-3-pyridyl]-α-phenylthio-4-chloro-phenylacetamide,
N-[2,4-bis(methylthio)-6-methyl-3-pyridyl]-α-(4-methoxyphenylthio)-4-chloro-phenylacetamide,
N-[2,4-bis(methylthio)-6-methyl-3-pyridyl]-α-(4-fluorophenylthio)-4-chloro-phenylacetamide,
N-[2,4-bis(methylthio)-6-methyl-3-pyridyl]-α-hexylthio-4-methoxy-phenylacetamide,
N-[2,4-bis(methylthio)-6-methyl-3-pyridyl]-α-benzylthio-4-methoxy-phenylacetamide,
N-[2,4-bis(methylthio)-6-methyl-3-pyridyl]-α-(4-chlorobenzylthio)-4-methoxy-phenylacetamide,
N-[2,4-bis(methylthio)-6-methyl-3-pyridyl]-α-(4-fluorobenzylthio)-4-methoxy-phenylacetamide,
N-[2,4-bis(methylthio)-6-methyl-3-pyridyl]-α-(4-methoxybenzylthio)-4-methoxy-phenylacetamide,
N-[2,4-bis(methylthio)-6-methyl-3-pyridyl]-α-phenylthio-4-methoxy-phenylacetamide,
N-[2,4-bis(methylthio)-6-methyl-3-pyridyl]-α-(4-fluorophenylthio)-4-methoxy-phenylacetamide,
N-[2,4-bis(methylthio)-6-methyl-3-pyridyl]-α-(4-methoxyphenylthio)-4-methoxy-phenylacetamide,
N-[2,4-bis(methylthio)-6-methyl-3-pyridyl]-α-O-methyl-4-methoxymandeloamide,
N-(2,6-diisopropyl-phenyl)-α-O-methyl-4-methoxymandeloamide,
N-[2,4-bis(methylthio)-6-methyl-3-pyridyl]-α-hexylthio-4-fluoro-phenylacetamide,
N-[2,4-bis(methylthio)-6-methyl-3-pyridyl]-α-benzylthio-4-fluoro-phenylacetamide
N-[2,4-bis(methylthio)-6-methyl-3-pyridyl]-α-(4-fluorobenzylthio)-4-fluoro-phenylacetamide,
N-[2,4-bis(methylthio)-6-methyl-3-pyridyl]-α-(4-methoxybenzylthio)-4-fluoro-phenylacetamide,
N-[2,4-bis(methylthio)-6-methyl-3-pyridyl]-α-phenylthio-4-fluoro-phenylacetamide,
N-[2,4-bis(methylthio)-6-methyl-3-pyridyl]-α-(4-fluorophenylthio)-4-fluoro-phenylacetamide,
N-[2,4-bis(methylthio)-6-methyl-3-pyridyl]-α-(4-methoxyphenylthio)-4-fluoro-phenylacetamide,
N-[2,4-bis(methylthio)-6-methyl-3-pyridyl]-α-hexylthio-3,4-dichloro-phenylacetamide,
N-[2,4-bis(methylthio)-6-methyl-3-pyridyl]-α-benzylthio-3,4-dichloro-phenylacetamide,
N-[2,4-bis(methylthio)-6-methyl-3-pyridyl]-α-(4-fluorobenzylthio)-3,4-dichloro-phenylacetamide,
N-[2,4-bis(methylthio)-6-methyl-3-pyridyl]-α-(4-methoxybenzylthio)-3,4-dichloro-phenylacetamide,
N-[2,4-bis(methylthio)-6-methyl-3-pyridyl]-α-hexylthio-2,4-difluoro-phenylacetamide,
N-[2,4-bis(methylthio)-6-methyl-3-pyridyl]-α-(4-methoxybenzylthio)-2,4-difluoro-phenylacetamide,
N-[2,4-bis(methylthio)-6-methyl-3-pyridyl]-α-hexylthio-3,4-dimethoxy-phenylacetamide,
N-[2,4-bis(methylthio)-6-methyl-3-pyridyl]-α-benzylthio-3,4-dimethoxy-phenylacetamide,
N-[2,4-bis(methylthio)-6-methyl-3-pyridyl]-α-(4-fluorobenzylthio)-3,4-dimethoxy-phenylacetamide,
N-[2,4-bis(methylthio)-6-methyl-3-pyridyl]-α-hexylthio-4-butoxy-phenylacetamide,
N-[2,4-bis(methylthio)-6-methyl-3-pyridyl]-α-benzylthio-4-butoxy-phenylacetamide,
N-[2,4-bis(methylthio)-6-methyl-3-pyridyl]-α-benzylthio-4-butoxy-phenylacetamide,
N-[2,4-bis(methylthio)-6-methyl-3-pyridyl]-α-hexylthio-4-phenoxy-phenylacetamide,
N-[2,4-bis(methylthio)-6-methyl-3-pyridyl]-α-benzylthio-4-phenoxy-phenylacetamide,
N-[2,4-bis(methylthio)-6-methyl-3-pyridyl]-α-(4-chlorobenzylthio)-4-phenoxy-phenylacetamide,
N-[2,4-bis(methylthio)-6-methyl-3-pyridyl]-α-hexylthio-3-phenoxy-phenylacetamide,
N-[2,4-bis(methylthio)-6-methyl-3-pyridyl]-α-hexylthio-3-(4'-bromophenoxy)-phenylacetamide,
N-[2,4-bis(methylthio)-6-methyl-3-pyridyl]-α-benzylthio-3-phenoxy-phenylacetamide,
N-[2,4-bis(methylthio)-6-methyl-3-pyridyl]-α-benzylthio-3-(4'-bromophenoxy)-phenylacetamide,
N-[2,4-bis(methylthio)-6-methyl-3-pyridyl]-α-(4-chlorobenzylthio)-3-phenoxy-phenylacetamide,
N-[2,4-bis(methylthio)-6-methyl-3-pyridyl]-α-(4-chlorobenzylthio)-3-(4'-bromophenoxy)-phenylacetamide,
N-[2,4-bis(methylthio)-6-methyl-3-pyridyl]-α-hexylthio-2-phenoxy-phenylacetamide,
N-[2,4-bis(methylthio)-6-methyl-3-pyridyl]-α-hexylthio-4-trifluoromethyl-phenylacetamide,
N-[2,4-bis(methylthio)-6-methyl-3-pyridyl]-α-benzylthio-4-trifluoromethyl-phenylacetamide,
N-[2,4-bis(methylthio)-6-methyl-3-pyridyl]-α-(4-fluorobenzylthio)-4-trifluoromethyl-phenylacetamide,
N-[2,4-bis(methylthio)-6-methyl-3-pyridyl]-α-(4-methoxybenzylthio)-4-trifluoromethyl-phenylacetamide,
N-[2,4-bis(methylthio)-6-methyl-3-pyridyl]-α-(4-fluorophenylthio)-4-trifluoromethyl-phenylacetamide,
N-[2,4-bis(methylthio)-6-methyl-3-pyridyl]-α-(4-methoxyphenylthio)-4-trifluoromethyl-phenylacetamide,
N-[2,4-bis(methylthio)-6-methyl-3-pyridyl]-α-hexylthio-4-isopropylphenylacetamide;
N-[2,4-bis(methylthio)-6-methyl-3-pyridyl]-α-benzylthio-4-isopropylphenylacetamide,
N-[2,4-bis(methylthio)-6-methyl-3-pyridyl]-α-(4-chlorobenzylthio)-4-isopropylphenylacetamide,
N-[2,4-bis(methylthio)-6-methyl-3-pyridyl]-α-(4-butoxybenzylthio)-4-isopropylphenylacetamide,
N-[2,4-bis(methylthio)-6-methyl-3-pyridyl]-α-hexylthio-4-tert-butylphenylacetamide,
N-[2,4-bis(methylthio)-6-methyl-3-pyridyl]-α-benzylthio-4-tert-butylphenylacetamide,
N-[2,4-bis(methylthio)-6-methyl-3-pyridyl]-α-(4-chlorobenzylthio)-4-tert-butylphenylacetamide,
N-[2,4-bis(methylthio)-6-methyl-3-pyridyl]-α-(4-tert-butylbenzylthio)-4-tert-butylphenylacetamide,
N-[2,4-bis(methylthio)-6-methyl-3-pyridyl]-α-hexylthio-4-biphenylacetamide,
N-[2,4-bis(methylthio)-6-methyl-3-pyridyl]-α-benzylthio-4-biphenylacetamide,
N-[2,4-bis(methylthio)-6-methyl-3-pyridyl]-α-(4-fluorobenzylthio)-4-biphenylacetamide,
N-[2,4-bis(methylthio)-6-methyl-3-pyridyl]-α-(4-methoxybenzylthio)-4-biphenylacetamide,
N-[2,4-bis(methylthio)-6-methyl-3-pyridyl]-α-(4-butoxybenzylthio)-4-biphenylacetamide,
N-[2,4-bis(methylthio)-6-methyl-3-pyridyl]-α-(3-pyridylmethylthio)-4-biphenylacetamide,
N-[2,4-bis(methylthio)-6-methyl-3-pyridyl]-α-hexylthio-4-nitro-phenylacetamide,
N-[2,4-bis(methylthio)-6-methyl-3-pyridyl]-α-hexylthio-3,4-methylenedioxyphenylacetamide, N-[2,4-bis(methylthio)-6-methyl-3-pyridyl]-α-(4-chlorobenzylthio)-3,4-methylenedioxyphenylacetamide, N-[2,4-bis(methylthio)-6-methyl-3-pyridyl]-α-hexylthio-2-thienylacetamide, N-[2,4-bis(methylthio)-6-methyl-3-pyridyl]-α-hexylthio-4-butyl-phenylacetamide, N-[2,4-bis(methylthio)-6-methyl-3-pyridyl]-α-(4-chlorobenzylthio)-4-butyl-phenylacetamide, N-[2,4-bis(methylthio)-6-methyl-3-pyridyl]-α-(4-butyl-benzylthio)-4-butyl-phenylacetamide, N-[2,4-bis(methylthio)-6-methylpyridin-3-yl]-2-(2-butyldecylthio)-acetamide;

N-[2,4-bis(methylthio)-6-methylpyridin-3-yl]-1-(2-phenylheptylthio)acetamide;

N-[2,4-bis(methylthio)-6-methylpyridin-3-yl]-2-[(6,6-dimethylbicyclo[3.1.1]hepten-2-yl)methyl]thioacetamide, N-[2,4-bis(methylthio)-6-methylpyridin-3-yl]-2-(E- and Z-2-pentyloct-2-enyl)thioacetamide;

N-[2,4-bis(methylthio)-6-methyl-3-pyridyl]-α-oxobenzeneacetamide;

N-[6-methyl-2,4-bis(methylthio)-3-pyridinyl]-2-oxodecanamide;

N-[6-methyl-2,4-bis(methylthio)-3-pyridinyl]-2-oxoundecanamide;

N-[6-methyl-2,4-bis(methylthio)-3-pyridinyl]-2-oxododecanamide;

N-[6-methyl-2,4-bis(methylthio)-3-pyridinyl]-2-oxotridecanamide;

N-[6-methyl-2,4-bis(methylthio)-3-pyridinyl]-2-oxotetradecanamide;

N-[6-methyl-2,4-bis(methylthio)-3-pyridinyl]-2-oxocyclohexaneacetamide;

4-methyl-N-[6-methyl-2,4-bis(methylthio)-3-pyridinyl]-alpha-oxocyclohexane-acetamide;

4-ethyl-N-[6-methyl-2,4-bis(methylthio)-3-pyridinyl]-alpha-oxocyclohexane-acetamide;

4-n-propyl-N-[6-methyl-2,4-bis(methylthio)-3-pyridinyl]-alpha-oxocyclohexane-acetamide;

4-n-butyl-N-[6-methyl-2,4-bis(methylthio)-3-pyridinyl]-alpha-oxocyclohexane-acetamide;

4-chloro-N-[6-methyl-2,4-bis(methylthio)-3-pyridinyl]-alpha-oxobenzene-acetamide;

4-fluoro-N-[6-methyl-2,4-bis(methylthio)-3-pyridinyl]-alpha-oxobenzene-acetamide;

4-bromo-N-[6-methyl-2,4-bis(methylthio)-3-pyridinyl]-alpha-oxobenzene-acetamide;

4-nitro-N-[6-methyl-2,4-bis(methylthio)-3-pyridinyl]-alpha-oxobenzene-acetamide;

4-methoxy-N-[6-methyl-2,4-bis(methylthio)-3-pyridinyl]-alpha-oxobenzene-acetamide;

4-phenoxy-N-[6-methyl-2,4-bis(methylthio)-3-pyridinyl]-alpha-oxobenzene-acetamide;

4-trifluoromethyl-N-[6-methyl-2,4-bis(methylthio)-3-pyridinyl]-alpha-oxobenzene-acetamide;

N-[6-methyl-2,4-bis(methylthio)-3-pyridinyl]-alpha-oxo[1,1'-biphenyl]-4-acetamide;

α,α-difluoro-N-[6-methyl-2,4-bis(methylthio)-3-pyridinyl][1,1'-biphenyl]-4-acetamide;

N-[difluoro[4-(trifluoromethyl)phenyl]acetyl]-α,α-difluoro-N-[6-methyl-2,4-bis(methylthio)-3-pyridinyl]-4-(trifluoromethyl)benzeneacetamide;

α,α-difluoro-N-[6-methyl-2,4-bis(methylthio)-3-pyridinyl]-4-(trifluoromethyl)benzeneacetamide;

α,α-difluoro-N-[6-methyl-2,4-bis(methylthio)-3-pyridinyl]-4-chlorobenzeneacetamide;

α,α-difluoro-N-[6-methyl-2,4-bis(methylthio)-3-pyridinyl]-4-methoxylbenzeneacetamide;

α,α-difluoro-N-[6-methyl-2,4-bis(methylthio)-3-pyridinyl]-4-butoxylbenzeneacetamide;

α,α-difluoro-N-[6-methyl-2,4-bis(methylthio)-3-pyridinyl]-4-bromobenzeneacetamide;

α,α-difluoro-N-[6-methyl-2,4-bis(methylthio)-3-pyridinyl]-4-cyclohexylbenzeneacetamide;

α,α-difluoro-N-[6-methyl-2,4-bis(methylthio)-3-pyridinyl]-4-butylbenzeneacetamide;

α,α-difluoro-N-[6-methyl-2,4-bis(methylthio)-3-pyridinyl]-cyclohexanacetamide;

α,α-difluoro-N-[6-methyl-2,4-bis(methylthio)-3-pyridinyl]-4-methylcyclohexanacetamide;

α,α-difluoro-N-[6-methyl-2,4-bis(methylthio)-3-pyridinyl]-4-n-butylcyclohexanacetamide;

α,α-difluoro-N-[6-methyl-2,4-bis(methylthio)-3-pyridinyl]-4-phenylcyclohexanacetamide;

α,α-difluoro-N-[6-methyl-2,4-bis(methylthio)-3-pyridinyl]-(4-isobutyl)phenylacetamide.

The present invention also provides pharmaceutical compositions comprising a compound of Formula I and a pharmaceutically acceptable carrier.

The compounds described above are useful as antiatherosclerotic and antihypercholesterolemic agents in a mammal when administered as pharmaceutical compositions to a mammal in need of treatment with such antiatherosclerotic and antihypercholesterolemic agents. The present invention includes pharmaceutical compositions containing an effective ACAT-inhibiting or antiatherosclerotic or cholesterol-lowering amount of the above described compounds of Formula I. The present invention also includes methods of treating hypercholesterolemia or atherosclerosis in a mammal comprising administering to the mammal a therapeutically effective amount of a compound of Formula I described above.

The compounds of the present invention can also be administered in combination with one or more additional therapeutic agents. Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

By "therapeutically effective amount" it is meant an amount of a compound of Formula I that when administered alone or in combination with an additional therapeutic agent to a cell or mammal is effective to inhibit ACAT so as to prevent or ameliorate the atherosclerosis or hypercholesterolemia disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The compounds herein described may have asymmetric centers. Unless otherwise indicated, all chiral, diastereomeric and racemic forms are included in the present invention. Many geometric isomers of olefins, C═N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable occurs more than one time in any constituent or in any formula, its definition on each occurrence is independent of its definition at every other occurrence. Thus, for example, if a group is shown to be substituted with 0–3 $R^{30}$, then said group may optionally be substituted with up to three $R^{30}$ and $R^{30}$ at each occurrence is selected independently from the defined list of possible $R^{30}$. Also, by way of example, for the group —$N(R^{5a})_2$, each of the two $R^{5a}$ substituents on N is independently selected from the defined list of possible $R^{5a}$. Similarly, by way of example, for the group —$C(R^7)_2$—, each of the two $R^7$ substituents on C is independently selected from the defined list of possible $R^7$.

When a bond to a substituent is shown to cross the bond connecting two atoms in a ring, then such substituent may be bonded to any atom on the ring.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$–$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "alkylthio" represents an alkyl group of indicated number of carbon atoms attached through an sulfur bridge; "dialkylamino" represents a N atom substituted with 2 alkyl groups of the indicated number of carbon atoms; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "—(alkyl)—", "—(alkyenyl)—" and "—(phenyl)—", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thiophenyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the educt molecule must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternate methods must then be used.

Compounds of Formula I may be prepared by one of the following amide formation reactions:

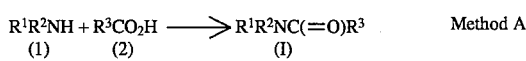

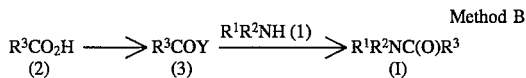

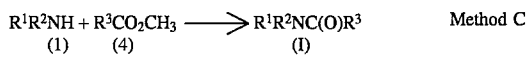

The amide formation reaction illustrated by the Method A represents one of the standard peptide coupling reactions, which employ one or a set of coupling reagents. Examples of the coupling reagents are well familiar to those skilled in the art, and typical examples may be found in Synthesis 453 (1972), Synthesis 549 (1974), or Richard C. Larock, Comprehensive Organic Transformations, VCH Publishers, New York, (1989) and references therein. Selected examples include but not limited to dicyclohexylcarbodiimide, N,N-dicarbonyldiimidazole and isobutyl chloroformate. This reaction is typically carried out in an inert solvent such as methylene chloride, chloroform, dichloroethane, diethyl ether, tetrahydrofuran or other suitable solvent, for from about 0.5 to 48 hours (preferably from about 1 to 18 hours) at a temperature ranging from −78° to reflux temperature (preferably at 0°–25°). This amide formation reaction may require additional reagent(s), such as N-methylmorpholine or triethylamine, depending the coupling reagent employed.

Alternatively the amide formation may be effected by first converting the acid, $R^3CO_2H$, to the corresponding acid halide, $R^3COY$ wherein Y is chloro or bromo, by reacting with a chlorinating or brominating agent, and then reacting with the amine, $R^1R^2NH$, in the presence of a suitable base as illustrated in the Method B. Examples of the chlorinating and brominating agents and conditions for acid halide formation reactions are well familiar to those skilled in the art, and typical examples may be found in Richard C. Larock, Comprehensive Organic Transformations, VCH Publishers, New York, (1989) and references therein. Selected examples of the chlorinating agent include but not limited to oxalyl chloride, thionyl chloride, phosphorous oxychloride, phosphorous trichloride and phosphorous pentachloride. This acid chrolide formation reaction may be carried out either in the absence of solvent or, alternatively, in the presence of an inert solvent such as methylene chloride, chloroform, dichloroethane, diethyl ether, tetrahydrofuran or other suitable solvent, for from about 0.5 to 48 hours (preferably from about 1 to 18 hours) at a temperature ranging from 0° to reflux temperature. Suitable bases for the following amide formation reaction between the acid halide and an amine include but not limited to pyridine, triethylamine, dimethylaminopyridine and imidazole. The amide formation reaction is typically carried out in pyridine or an inert solvent such as methylene chloride, chloroform, dichloroethane, diethyl ether, tetrahydrofuran or other suitable solvent, for from about 0.5 to 48 hours (preferably from about 1 to 18 hours) at a temperature ranging from 0° to reflux temperature.

Compounds of Formula I may also be prepared by reacting an ester, $R^3CO_2CH_3$, with an amine $R^1R^2NH$ in the presence of trimethylaluminum as illustrated in the Method C. This amide formation reaction is typically carried out in an inert solvent such as methylene chloride, dichloroethane, benzene or toluene for from about 0.5 to 48 hours (preferably from about 3 to 24 hours) at a temperature ranging from 25° to reflux temperature (preferably reflux temperature).

The acids and esters used in the amide formation reactions for the compounds of Formula I, wherein $R^3$ is $C(R^5)(R^6)XR^7$, may be prepared by one of the following methods:

Scheme 1

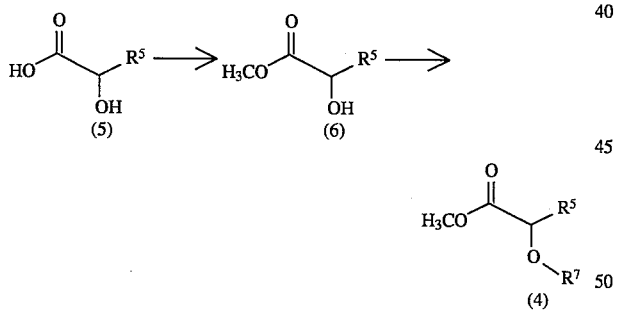

Mandelic acid or a substituted mandelic acid, when easily available, is first converted to an ester (6) (preferably methyl ester) by treating it with an acid such as sulfuric acid, hydrochloric acid, p-toluenesulfonic acid or camphorsulfonic acid in the corresponding alcohol (preferably methanol) as illustrated in the Scheme 1. Then the α-hydroxy group is alkylated with a base such as sodium hydride and $R^7$-Z wherein Z is Cl, Br or I to give an α-O-alkyl-mandeloester (4, wherein X is O). Typically the alkylation is carried out in an inert solvent such as tetrahydrofuran, benzene or N,N-dimethylformamide for from about 0.5 to 24 hours at a temperature ranging from 0° to reflux temperature. The alkylation may also be carried out by treating the hydroxy compound with $R^7$-Z in the presence of silver oxide ($Ag_2O$) for from 1 to 48 hours (preferably 8 to 24 hours) at a temperature ranging from 25° to reflux temperature.

Scheme 2

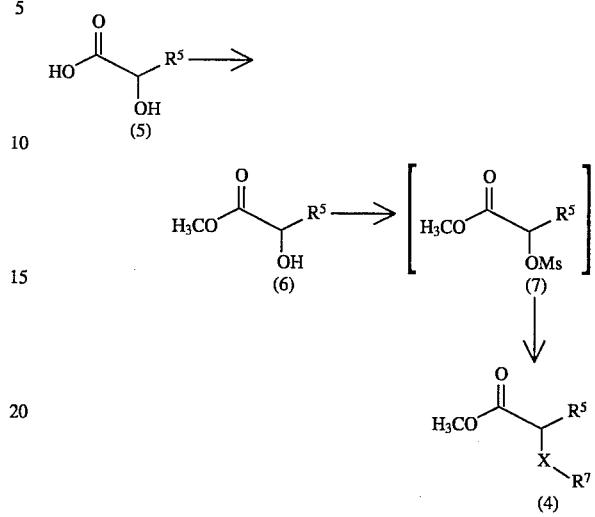

α-(Thio)alkoxy-phenylacetic acid esters (4, wherein X is O or S) may be prepared by converting the hydroxy group of the mandeloester (6) into a leaving group, such as methanesulfonyl ester, p-toluenesulfonyl ester (7) or an equivalent, and substituting it with an alcohol or a thiol in the presence of a base such as 1,8-diazabicyclo[5.4.0]undec-7-ene (DBU), 1,5-diazabicyclo[4.3.0]non-5-ene (DBN), sodium hydride or potassium tert-butoxide (Scheme 2). Typically sulfonyl esters prepared either by treating the hydroxy ester (6) with an alkylsulfonyl chloride in a chlorinated solvent in the presence of a base such as triethylamine or by treating an aromatic sulfonyl chloride in pyridine with or without a catalyst such as N,N-dimethyl-4-aminopyridine. The reaction is carried out for about 0.5 to 24 hours (preferably 0.5 to 2 hours) at a temperature ranging from 0° to reflux temperature (preferably room temperature). The substitution reaction is typically carried out in an inert solvent such as methylene chloride, dichloroethane, bezene or toluene for from about 0.5 to 24 hours (preferably 0.5 to 4 hours) at a temperature ranging from 0° to reflux temperature (preferably 25° to reflux temperature), when either DBU or DBN is employed as the base. When either sodium hydride or potassium tert-butoxide is used as the base, the reaction is typically carried out in an inert solvent such as tetrahydrofuran, diethyl ether, or benzene for from about 0.5 to 24 hours (preferably 0.5 to 4 hours) at a temperature ranging from 0° to reflux temperature (preferably 25° to reflux temperature).

Scheme 3

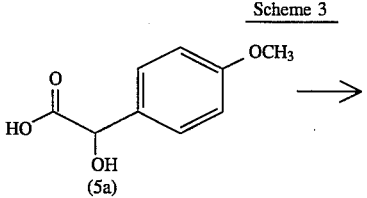

-continued
Scheme 3

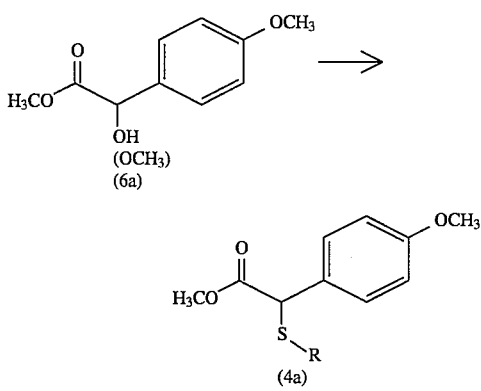

Certain α-thioalkoxy-phenylacetic acid esters (4, wherein X is S) may also be prepared by treating either an α-hydroxy ester or an α-alkoxy ester (6a) with a thiol in the presence of an acid catalyst such as sulfuric acid, hydrochloric acid, trifluoroacetic acid or boron trifluoride etherate (Scheme 3). The reaction is typically carried out in an inert solvent such as methylene chloride, dichloroethane, benzene or toluene for from 0.5 to 24 hours (preferably 0.5 to 4 hours) at a temperature ranging from 0° to reflux temperature (preferably 0° to 25°).

Scheme 4

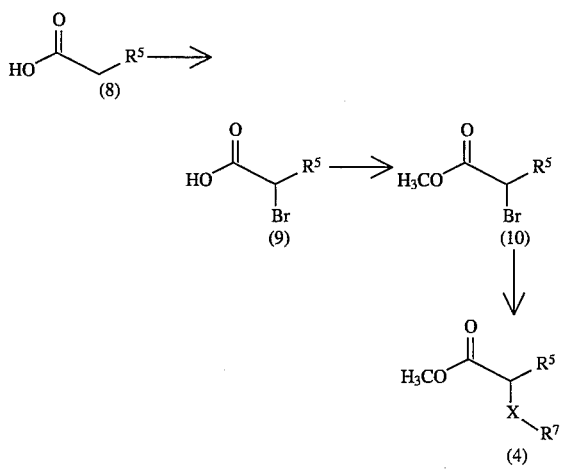

α-(Thio) alkoxy-phenylacetic acid esters (4, wherein X is O or S) may also be prepared from a phenylacetic acid (8) by a bezylic bromination, and an esterification followed a substitution reaction (Scheme 4). The bromination is typically carried out using either N-bromosuccinimide or 1,3-dibromo-5,5-dimethylhydantoin in carbon tetrachloride or benzene in the presence of a radical initiator such as benzoyl peroxide or azobisisobutyronitrile (AIBN) for from 0.5 to 16 hours at reflux temperature. The bromo-acid (9) is then converted to a bromo-ester (10) (preferably methyl ester) by treating it with an acid such as sulfuric acid, hydrochloric acid, p-toluenesulfonic acid or camphorsulfonic acid in the corresponding alcohol (preferably methanol) as described in the Scheme 1. Bromide of the bromo-ester (10) is converted to an alkoxy- or a thioalkoxy-ester (4) by treating with an alcohol or a thiol in the presence of a base such as 1,8-diazabicyclo[5.4.0]undec-7-ene (DBU), 1,5-diazabicyclo[4.3.0]non-5-ene (DBN), sodium hydride or potassium tert-butoxide. The substitution reaction is typically carried out in an inert solvent such as methylene chloride, dichloroethane, bezene or toluene for from about 0.5 to 24 hours (preferably 0.5 to 4 hours) at a temperature ranging from 0° to reflux temperature (preferably 25° to reflux temperature), when either DBU or DBN is employed as the base. When either sodium hydride or potassium tert-butoxide is used as the base, the reaction is typically carried out in an inert solvent such as tetrahydrofuran, diethyl ether, or benzene for from about 0.5 to 24 hours (preferably 0.5 to 4 hours) at a temperature ranging from 0° to reflux temperature (preferably 25° to reflux temperature).

Scheme 5

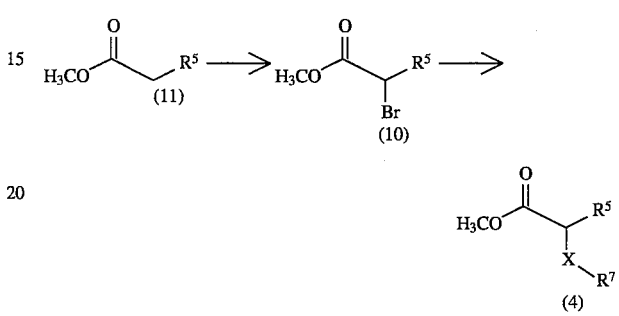

α-(Thio) alkoxy-phenylacetic acid esters (4, wherein X is O or S) may also be prepared from a phenylacetic acid ester (11) by brominating with either N-bromosuccinimide or 1,3-dibromo-5,5-dimethylhydantoin followed a substitution reaction (Scheme 5). The radical bromination is typically carried out using either N-bromosuccinimide or 1,3-dibromo-5,5-dimethylhydantoin in carbon tetrachloride or benzene in the presence of a radical initiator such as benzoyl peroxide or azobisisobutyronitrile (AIBN) for from 0.5 to 16 hours at reflux temperature. The bromination may also be achieved by first treating the phenylacetic acid ester (11) with a base, such as lithium diisopropylimide or lithium hexamethyldisilazide followed by bromine. This reaction is typically carried out in either tetrahydrofuran or diethyl ether for from 0.5 to 5 hours at a temperature ranging from −78° to room temperature. The substitution is then carried out by the same substition reaction as described in the Scheme 4 to provide the α-(thio)alkoxy-phenylacetic acid esters.

Scheme 6

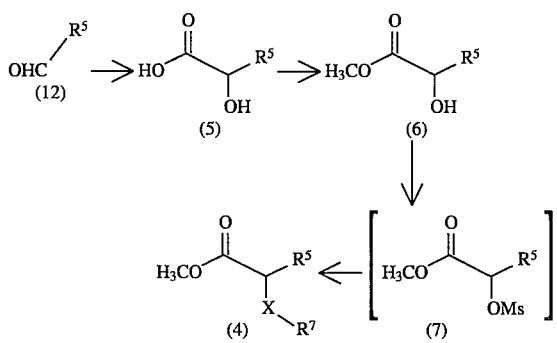

α-(Thio)alkoxy-phenylacetic acid esters (4, wherein X is O or S) may also be prepared from a benzaldehyde (12) through a mandelic acid (5). The mandelic acid is converted to the α-(thio)alkoxy-phenylacetic acid esters by the same procedures as described in Schemes 1 and 2 (Scheme 6). Process for mandelic acid synthesis is well documented in the chemistry literature. Some typical examples may be found in B. B. Corson, et al, Organic Synthesis Collective Volumn 1, 336 (1941) and references therein.

Scheme 7

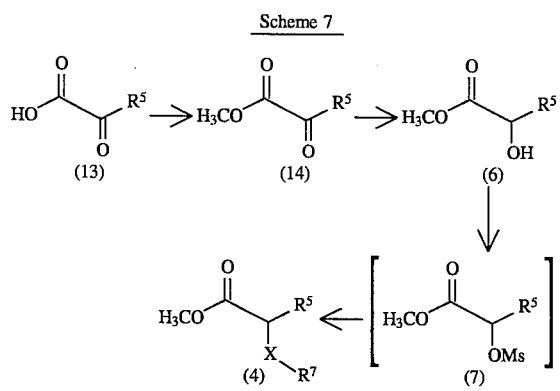

Certain α-thioalkoxy-phenylacetic acid esters or heterocyclic acid esters (4, wherein $R^5$ is substituted phenyl or heterocycles such as thiophene, and X is S) may also be prepared by first converting a glyoxylic acid (13) to an ester (14) and then reducing the α-keto group to an alcohol to give the corresponding α-hydroxy ester (6) (Scheme 7). The hydroxy-ester (6) may be converted to an α-thioalkoxy-acetic acid ester (4) according to a similar procedure that described in Schemes 1 and 2. The esterification reaction is typically carried out in an alcoholic solvent (preferably methanol) with an acid such as sufuric acid, hydrochloric acid, p-toluenesulfonic acid or camphorsulfonic acid as described in Sceheme 1. The reduction of ketone in typically carried out with sodium borohydride in either ethanol or methanol for from about 5 minutes to 2 hours (preferably 10 to 30 minutes) at a temperature ranging from −10° to 25° (preferably at 0°–10°).

The detailed processes for preparing the compounds of Formula I are illustrated by the following examples. It is, however, understood that this invention is not limited to the specific details of these examples. Melting points are uncorrected. All the temperatures are reported in Celsius. Proton nuclear magnetic resonance spectra ($^1$H NMR) were measured in chloroform-d ($CDCl_3$) unless otherwise specified and the peaks are reported in parts per million (ppm) downfield from tetramethylsilane (TMS). The coupling patterns are reported as follows: s, singlet; d, doublet; t, triplet; q, quartet; qt, quintet; m, multiplet.

EXAMPLE 1

N-[2,4-bis(methylthio)-6-methyl-3-pyridyl]-D-(−)-α-O-hexyl-mandeloamide

Part 1.

To a stirred solution of D-(−)-mandelic acid (20 g) in methanol (100 ml) was added concentrated sulfuric acid (6 g) and the mixture was refluxed for 2.5 hours. After cooling to room temperature it was concentrated to about 50 ml and the residue was dissolved in methylene chloride (about 300 ml). The solution was the washed with water, saturated sodium bicarbonte and water, dried (magnesium sulfate) and evaporated to give a clear oil, which crystallized upon cooling to give 21.7 g of methyl D-(−)-mandelate, a compound of Formula 6, wherein $R^5$ is phenyl.
Part 2.

To a mixture of methyl mandelate (6.65 g) and iodohexane (50 g) was added silver oxide (16.5 g) and the mixture was stirred in the dark for one day at room temperature. After filtration through Celite® the filtrate was evaporated to give an oily residue. It was column chromatographed on silica gel with elution by 3:7 ethyl acetate-hexane to give 9.3 g of pure methyl α-O-hexyl-mandelate, a compound of Formular 4, wherein $R^5$ is phenyl and $R^7$ is hexyl.
Part 3.

A solution of methyl α-O-hexyl-mandelate (9.3 g) and lithium iodide (44 g) in N,N-dimethylformamide (160 ml) was refluxed for 8 hours. After cooling it was acidified with 1N-HCl and was partitioned between methylene chloride and water. The organic layer was separated, washed with water, dried (magnesium sulfate) and evaporated to give an oily residue. It was purified by column chromatography on silica gel with elution by 1:1 ethyl acetate-hexane to provide the corresponding acid, α-O-hexyl-mandelic acid.
Part 4.

To a stirred solution of α-O-hexyl-mandelic acid (0.26 g) in dry methylene chloride (3 ml) at 0° was added N-methylmorpholine (0.26 ml) followed by isobutyl chloroformate (0.14 ml), and the mixture was stirred for 25 minutes at 0°. Then a solution of 3-amino-2,4-bis(methylthio)-6-methylpyridine (0.2 g) in methylene chloride (2 ml) was added and the mixture was stirred for 2.5 hours while raising the temperature to 25° gradually. It was partitioned between ethyl acetate and water, and the oranic layer was separated. The extract was washed with water and brine, dried (magnesium sulfate) and evaporated to give an oily residue. Purification by column chromatography on silica gel with elution by 2:8 ethyl acetate-hexane afforded an oily residue of pure N-[2,4-bis(methylthio)-6-methyl-3-pyridyl]-α-O-hexyl-mandeloamide, a compound of Formula I.
$^1$H NMR (300 MHz): δ7.99 (1H, s); 7.56–7.54 (2H, m); 7.39–7.24 (3H, m); 6.61 (1H, s); 4.89 (1H, s); 3.71–3.55 (2H, m); 2.92 (1H, d, J=8.42 Hz); 2.46 (3H, s); 2.45 (3H, s); 2.44 (3H, s); 1.71–1.64 (2H, m); 1.43–1.37 (2H, m); 1.31–1.23 (4H, m); 0.87 (3H, t, J=6.78 Hz).

EXAMPLE 2

N-[2,4-bis(methylthio)-6-methyl-3-pyridyl]-L-(+)-α-O-hexyl-mandeloamide

According to a similar procedure to that described in Example 1, the titled compound was prepared from L-(+)-mandelic acid.

m.p. (petroleum ether), 58°–59.5°
$^1$H NMR (300 MHz):δ7.99 (1H, s); 7.56–7.54 (2H, m); 7.39–7.24 (3H, m); 6.61 (1H, s); 4.89 (1H, s); 3.71–3.55 (2H, m); 2.92 (1H, d, J=8.42 Hz); 2.46 (3H, s); 2.45 (3H, s); 2.44 (3H, s); 1.71–1.64 (2H, m); 1.43–1.37 (2H, m); 1.31–1.23 (4H, m); 0.87 (3H, t, J=6.78 Hz).

EXAMPLE 14

N-[2,4-bis(methylthio)-6-methyl-3-pyridyl]-L-(+)-α-O-benzyl-mandeloamide

According to a similar procedure to that described in Example 1, methyl α-O-benzyl-mandelate, a compound of formula 4 wherein X is O, $R^5$ is phenyl and $R^7$ is benzyl, was prepared from L-(+)-mandelic acid. The amide formation reaction was carried out by the Method C as desccribed in detail below.

To a stirred solution of methyl α-O-benzyl-mandelate (0.257 g) and 3-amino-2,4-bis(methylthio)-6-methyl-pyridine (0.2 g) in dry methylene chloride (7 ml) was added a 2M-solution of trimethylaluminum in toluene (1 ml) dropwise and the mixture was stirred for 15 hours at room temperature. At the end of the stirring, it was cooled to 0° and acidified slowly with 1N-HCl. The mixture was extracted with methylene chloride, and the extract was washed with water, dried (magnesium sulfate) and evaporated to give an oily residue. It was column chromatographed on silica gel with elution by 1:9 the 3:7 ethyl acetate-hexane to give a solid product. Recrystallization from ethyl acetate and hexane gave 98 mg of pure N-[2,4-bis(methylthio)-6-methyl-3-pyridyl]-L-(+)-α-O-benzyl-mandeloamide, a compound of formula I.

m.p. (ethyl acetate and hexane), 125°–126°

$^1$H NMR (300 MHz): δ8.04 (1H, s); 7.59 (2H, d, J=8.05 Hz); 7.42–7.32 (8H, m); 6.61 (1H, s); 5.02 (1H, s); 4.71 (2H, s); 2.48 (3H, s); 2.47 (3H, s); 2.35 (3H, s).

EXAMPLE 40

N-[2,4-bis(methylthio)-6-methyl-3-pyridyl]-D-(−)-α-hexylthio-phenylacetamide

Part 1.

Same as Part 1 of Example 1.

Part 2.

To a stirred solution of methyl D-(−)-mandelate (20 g) and triethylamine (18.26 g) in dry methylene chloride (250 ml) at 0° was added dropwise methanesulfonyl chloride (15.16 g) over a period of 10 minutes, and the mixture was stirred for 1 hour at 0°–20°. At the end of the stirring was added 250 ml of methylene chloride and the solution was washed with water, 1N-HCl, water, saturated sodium bicarbonate and brine. It was dried (magnesium sulfate) and evaporated to give a crystalline solid of methyl D-(−)-α-O-methanesulfonyl-mandelate (28.7 g), a compound of formula 7 wherein $R^5$ is phenyl.

Part 3.

To a stirred solution of methyl L-(+)-α-O-methanesulfonyl-mandelate (3.36 g) in dry tetrahydrofuran (50 ml) was added a solution sodium hexanethiolate in 20 ml of tetrahydrofuran [prepared in a separate flask by treating hexanethiol (1.77 g) in tetrahydrofuran (20 ml) with sodium hydride (0.36 g)] and the mixture was continued to stir for 2 hours at room temperature. The reaction was quenched with saturated ammonium chloride and extracted with ethyl acetate. The extract was washed with water and brine, dried (magnesium sulfate) and evaporated to give an oily residue of methyl α-hexylthio-phenylacetate (3.7 g), a compound of formula 4 wherein X is S, $R^5$ is phenyl and $R^7$ is hexyl.

Part 4.

To a stirred solution α-hexylthio-phenylacetate (204 mg) and 3-amino-2,4-bis(methylthio)-6-methyl-pyridine (146 mg) in methylene chloride (5 ml) was added dropwise 2M solution of trimethylaluminum in toluene (0.4 ml), and the mixture was refluxed for 16 hours. After cooling to 0° it was acidified slowly with 1N hydrochloric acid, and extracted with ethyl acetate twice. The combined extracts were washed with water and brine, dried (magnesium sulfate) and evaporated to give a solid residue. It was purified by a column chromatography on silica gel with elution by 2:8 ethyl acetate-hexane to give a solid residue. Crystallization from ethyl ether and hexane to provide pure N-[2,4-bis(methylthio)-6-methyl-3-pyridyl]-α-hexylthio-phenylacetamide (24 mg).

m.p., 132°–133°

$^1$H NMR (300 MHz): δ8.15 (1H, s); 7.54 (2H, d, J=6.96 Hz); 7.37–7.29 (3H, m); 6.61 (1H, s); 4.71 (1H, s); 2.83 (2H, t, J=6.78 Hz); 2.47 (3H, s); 2.46 (3H, s); 2.35 (3H, s); 1.70–1.64 (2H, m); 1.42–1.37 (2H, m); 1.29–1.24 (4H, m); 0.86 (3H, t, J=6.78 Hz).

EXAMPLE 41

N-[2,4-bis(methylthio)-6-methyl-3-pyridyl]-L-(+)-α-hexylthio-phenylacetamide

According to a similar procedure to that described in Example 40, the titled compound was prepared. oil $^1$H NMR (300 MHz): δ8.18 (1H, s); 7.58–7.54 (2H, m); 7.39–7.29 (3H, m); 6.63 (1H, s); 4.73 (1H, s); 2.88–2.82 (2H, m); 2.49 (3H, s); 2.43 (3H, s); 2.36 (3H, s); 1.72–1.62 (2H, m); 1.43–1.36 (2H, m); 1.31–1.26 (4H, m); 0.88 (3H, t, J=6.77 Hz).

EXAMPLE 42

N-(2,6-diisopropyl-phenyl)-D-(−)-α-hexylthio-phenylacetamide

According to a similar procedure to that described in Example 40, the titled compound was prepared.

m.p., 141°–142°

$^1$H NMR (300 MHz): δ7.78 (1H, s); 7.53 (2H, d, J=6.96 Hz); 7.41–7.33 (3H, m); 7.32–7.23 (1H, m); 7.12 (2H, d, J=7.69 Hz); 4.74 (1H, s); 2.75–2.68 (2H, m); 1.71–1.64 (2H, m); 1.42–1.33 (2H, m); 1.07 (6H, t, J=6.96 Hz); 0.88 (3H, t, J=6.96 Hz).

EXAMPLE 46

N-[2,4-bis(methylthio)-6-methyl-3-pyridyl]-D-(−)-α-benzylthio-phenylacetamide

According to a similar procedure to that described in Example 40, the titled compound was prepared.

m.p., 156°–158°

$^1$H NMR (300 MHz): δ8.02 (1H, s); 7.46 (2H, d, J=6.59 Hz); 7.38 (2H, d, J=6.96 Hz); 7.35–7.28 (5H, m); 6.63 (1H, s); 4.55 (1H, s); 4.04 (2H, dd, J=13.18, 44.68 Hz); 2.49 (3H, s); 2.47 (3H, s); 2.37 (3H, s).

EXAMPLE 47

N-[2,4-bis(methylthio)-6-methyl-3-pyridyl]-L-(+)-α-benzylthio-phenylacetamide

According to a similar procedure to that described in Example 40, the titled compound was prepared.

$^1$H NMR (300 MHz): δ8.04 (1H, s); 7.49–7.46 (2H, m); 7.42–7.26 (m, 8H); 6.65 (1H, s); 4.58 (1H, s); 4.13 (1H, d, J=13.18 Hz, A of AB); 3.98 (1H, d, J=13.18 Hz, B of AB); 2.51 (3H, s); 2.49 (3H, s); 2.39 (3H, s).

EXAMPLE 48

N-(2,6-diisopropyl-phenyl)-D-(−)-α-benzylthio-phenylacetamide

According to a similar procedure to that described in Example 40, the titled compound was prepared.

m.p., 182.5°–183.5°

$^1$H NMR (300 MHz): δ7.11 (3H, d, J=7.69 Hz); 7.39–7.29 (6H, m); 7.27–7.22 (2H, m) 7.11 (2H, d, J=7.69 Hz); 4.60 (1H, s); 3.88 (2H, dd, J=13.18, 26.00 Hz); 2.85 (2H, bs); 1.09 (6H, s); 1.06 (6H, s).

EXAMPLE 49

N-[2,4-bis(methylthio)-6-methyl-3-pyridyl]-
D-(−)-α-ethylthio-phenylacetamide

According to a similar procedure to that described in Example 40, the titled compound was prepared.

m.p., 149°–151°

$^1$H NMR (300 MHz): δ8.11 (1H, s); 7.55 (2H, d, J=7.69 Hz); 7.39–7.29 (3H, m); 6.62 (1H, s); 4.75 (1H, s); 2.89–2.83 (2H, m); 2.48 (3H, s); 2.47 (3H, s); 2.36 (3H, s); 1.34 (3H, t, J=7.33 Hz).

EXAMPLE 50

N-[2,4-bis(methylthio)-6-methyl-3-pyridyl]-
L-(+)-α-ethylthio-phenylacetamide

According to a similar procedure to that described in Example 40, the titled compound was prepared.

m.p., 150°–152°

$^1$H NMR (300 MHz): δ8.11 (1H, s); 7.55 (2H, d, J=7.69 Hz); 7.39–7.29 (3H, m); 6.62 (1H, s); 4.75 (1H, s); 2.88–2.84 (2H, m); 2.48 (3H, s); 2.47 (3H, s); 2.36 (3H, s); 1.34 (3H, t, J=7.33 Hz).

EXAMPLE 63

N-[2,4-his (methylthio)-6-methyl-3-pyridyl]-
L-(+)-α-phenylthio-phenylacetamide

According to a similar procedure to that described in Example 40, the titled compound was prepared.

m.p., 156°–158°

$^1$H NMR (300 MHz): δ7.89 (1H, s); 7.57 (2H, d, J=6.96 Hz); 7.44 (2H, d, J=1.10 Hz); 7.38–7.32 (3H, m); 7.31–7.21 (3H, m); 6.58 (1H, s); 5.13 (1H, s); 2.43 (3H, s); 2.41 (3H, s); 2.30 (3H, s).

EXAMPLE 64

N-(2,6-diisopropyl-phenyl)-D-(−)-
α-benzylthio-phenylacetamide

According to a similar procedure to that described in Example 40, the titled compound was prepared.

m.p., 199°–200°

$^1$H NMR (300 MHz): δ7.92 (1H, s); 7.59 (2H, d, J=6.23 Hz); 7.46 (2H, d, J=7.69 Hz); 7.41–7.28 (2H, m); 7.27–7.20 (5H, m); 7.05 (2H, d, J=7.69 Hz); 5.26 (1H, s); 2.53 (2H, quintet, J=6.96 Hz); 0.97 (3H, s); 0.95 (3H, s); 0.88 (3H, s); 0.85 (3H, s).

EXAMPLE 85

N-[2,4-bis(methylthio)-6-methyl-3-pyridyl]-
α-hexylthio-4-chloro-phenylacetamide According to a similar procedure to that described in Example 40, the titled compound was prepared.

m.p., 164.5°–165.5°

$^1$H NMR (300 MHz): δ8.22 (1H, s); 7.47 (2H, d, J=8.42 Hz); 7.31 (2H, d, J=8.42 Hz); 6.61 (1H, s); 4.67 (1H, s); 2.82 (2H, t, J=8.79 Hz); 2.48 (3H, s); 2.46 (3H, s); 2.36 (3H, s); 1.69–1.60 (2H, m); 1.43–1.34 (2H, m); 1.29–1.24 (4H, m); 0.87 (3H, t, J=6.77 Hz).

EXAMPLE 89

N-[2,4-bis(methylthio)-6-methyl-3-pyridyl]-α-
benzylthio-4-chloro-phenylacetamide According to a similar procedure to that described in Example 40, the titled compound was prepared.

m.p., 200.5°–202.0°

$^1$H NMR (300 MHz): δ8.09 (1H, s); 7.41–7.36 (4H, m); 7.35–7.26 (SH, m); 6.65 (1H, s); 4.51 (1H, s); 4.04 (2H, dd, J=13.18, 46.51 Hz); 2.51 (3H, s); 2.49 (3H, s); 2.40 (3H, s).

EXAMPLE 90

N-[2,4-bis(methylthio)-6-methyl-3-pyridyl]-
α-(4-methoxy-benzylthio)-4-chloro-phenylacetamide Part 1.

According to a similar procedure to that described in Part 1 of Example 1, methyl 4-chloro-mandelate was prepared from 4-chloromandelic acid.

Part 2.

According to a similar procedure to that described in Part 2 of Example 40, methyl α-O-methanesulfonyl-4-chloro-mandelate wa,mandelate Part 3.

To a stirred solution of methyl α-methanesulfonyloxy-4-chloro-phenylacetate (0.28 g) and 4-methoxybenzylthiol (0.155 g) in dry methylene chloride (6 ml) was 1,8-diazabi-cyclo[5.4.0]undec-7-ene (DBU, 0.26 ml), and the mixture was continued to stir for 16 hours at room temperature. The reaction was quenched with 1N HCl and extracted with methylene chloride. The extract was washed with water and brine, dried (magnesium sulfate) and evaporated to give an oily residue. It was purified by column chromatography on silica gel with elution by 1:9 ethyl acetate-hexane to provide pure methyl α-(4-methoxy)benzylthio-4-chloro-phenylacetate (0.19 g), a compound of formula 4 wherein X is S, $R^5$ is 4-chloro-phenyl and $R^7$ is 4-methoxybenzyl.

Part 4.

According to a similar procedure to that described in Part 4 of Example 40, the titled compound was prepared from methyl α-(4-methoxy)benzylthio-4-chloro-phenylacetate.

m.p., 194.5°

$^1$H NMR (300 MHz): δ8.12 (1H, s); 7.40 (2H, d, J=8.79 Hz); 7.31–7.28 (4H, m); 6.86 (2H, d, J=8.42 Hz); 6.65 (1H, s); 4.49 (1H, s); 4.00 (2H, dd, J=13.19, 47.61 Hz); 3.80 (3H, s); 2.51 (3H, s); 2.48 (3H, s); 2.39 (3H, s).

EXAMPLE 91

N-[2,4-bis(methylthio)-6-methyl-3-pyridyl]-
α-(4-fluoro-benzylthio)-4-chloro-phenylacetamide According to a similar procedure to that described in Example 90, the titled compound was prepared.

m.p., 198.4°

$^1$H NMR (300 MHz): δ7.98 (1H, s); 7.40 (2H, d, J=8.42 Hz); 7.38–7.33 (4H, m); 7.02 (2H, t, J=8.42 Hz); 6.65 (1H, s); 4.48 (1H, s); 4.01 (2H, dd, J=13.18, 51.64 Hz); 2.51 (3H, s); 2.48 (3H, s); 2.39 (3H, s).

EXAMPLE 92

N-[2,4-bis(methylthio)-6-methyl-3-pyridyl]-
α-(4-chloro-benzylthio)-4-chloro-phenylacetamide According to a similar procedure to that described in Example 90, the titled compound was prepared.

m.p., 185°–187°

¹H NMR (300 MHz): δ7.95 (1H, s); 7.41 (2H, d, J=8.42 Hz); 7.32 (2H, d, J=8.42 Hz); 6.66 (1H, s); 4.49 (1H, s); 4.01 (2H, dd, J=13.55, 56.40 Hz); 2.52 (3H, s); 2.49 (3H, s); 2.40 (3H, s).

EXAMPLE 102

N-[2,4-bis(methylthio)-6-methyl-3-pyridyl]-α-phenylthio-4-chloro-phenylacetamide According to a similar procedure to that described in Example 40, the titled compound was prepared.

m.p., 176–177

¹H NMR (300 MHz): δ7.91 (1H, s); 7.48 (2H, d, J=6.59 Hz); 7.45 (2H, d, J=6.59 Hz); 7.34–7.27 (5H, m); 6.60 (1H, s); 5.09 (1H, s); 2.45 (3H, s); 2.44 (3H, s); 2.32 (3H, s).

EXAMPLE 103

N-[2,4-bis(methylthio)-6-methyl-3-pyridyl]-α-(4-methoxy-phenylthio)-4-chloro-phenylacetamide According to a similar procedure to that described in Example 90, the titled compound was prepared.

m.p., 163°–165°

¹H NMR (300 MHz): δ7.76 (1H, s); 7.42 (4H, t, J=8.42 Hz); 7.31 (2H, d, J=8.42 Hz); 6.82 (2H, d, J=8.42 Hz); 6.62 (1H, s); 4.93 (1H, s); 3.79 (3H, s); 2.47 (3H, s); 2.46 (3H, s); 2.35 (3H, s).

EXAMPLE 104

N-[2,4-bis(methylthio)-6-methyl-3-pyridyl]-α-(4-fluoro-phenylthio)-4-chloro-phenylacetamide According to a similar procedure to that described in Example 90, the titled compound was prepared.

m.p., 193.5°–195°

¹H NMR (300 MHz): δ7.66 (1H, s); 7.46 (2H, d, J=8.79 Hz); 7.44 (2H, d, J=5.13 Hz); 7.33 (2H, d, J=8.42 Hz); 7.00 (2H, t, J=8.79 Hz); 6.61 (1H, s); 5.00 (1H, s); 2.47 (3H, s); 2.46 (3H, s); 2.35 (3H, s).

EXAMPLE 118

N-[2,4-bis(methylthio)-6-methyl-3-pyridyl]-α-hexylthio-4-methoxy-phenylacetamide According to a similar procedure to that described in Example 40, the titled compound was prepared.

m.p., 129.5°–130.5°

¹H NMR (300 MHz): δ8.11 (1H, s); 7.46 (2H, d, J=8.79 Hz); 6.87 (2H, d, J=8.42 Hz); 6.62 (1H, s); 4.67 (1H, s); 3.79 (3H, s); 2.81 (2H, t, J=8.79 Hz); 2.47 (3H, s); 2.46 (3H, s); 2.36 (3H, s); 1.69–1.63 (2H, m); 1.41–1.37 (2H, m); 1.29–1.24 (4H, m); 0.86 (3H, t, J=6.78 Hz).

EXAMPLE 122

N-[2,4-bis(methylthio)-6-methyl-3-pyridyl]-α-benzylthio-4-methoxy-phenylacetamide According to a similar procedure to that described in Example 90, the titled compound was prepared.

m.p., 173°–175°

¹H NMR (300 MHz): δ7.98 (1H, s); 7.39 (2H, d, J=8.42 Hz); 7.35–7.26 (5H, m); 6.86 (2H, d, J=8.79 Hz); 6.64 (1H, s); 4.53 (1H, s); 4.03 (2H, dd, J=13.18,45.78 Hz); 3.78 (3H, s); 2.50 (3H, s); 2.48 (3H, s); 2.39 (3H, s).

EXAMPLE 123

N-[2,4-bis(methylthio)-6-methyl-3-pyridyl]-α-(4-chloro-benzylthio)-4-methoxy-phenylacetamide According to a similar procedure to that described in Example 90, the titled compound was prepared.

m.p., 178°–180°

¹H NMR (300 MHz): δ7.82 (1H, s); 7.40 (2H, d, J=8.42 Hz); 7.32 (4H, quartet, J=6.59, 10.26 Hz); 6.88 (2H, d, J=8.79 Hz); 6.65 (1H, s); 4.50 (1H, s); 3.99 (2H, dd, J=13.55, 57.13 Hz); 3.80 (3H, s); 2.51 (3H, s); 2.49 (3H, s); 2.39 (3H, s).

EXAMPLE 124

N-[2,4-bis(methylthio)-6-methyl-3-pyridyl]-α-(4-fluoro-benzylthio)-4-methoxy-phenylacetamide According to a similar procedure to that described in Example 90, the titled compound was prepared.

m.p., 176°–177°

¹H NMR (300 MHz): δ7.87 (1H, s); 7.42–7.33 (4H, m); 7.02 (2H, t, J=8.79 Hz); 6.88 (2H, d, J=8.79 Hz); 6.65 (1H, s); 4.50 (1H, s); 4.01 (2H, dd, J=13.18, 52.01 Hz); 3.80 (3H, s); 2.51 (3H, s); 2.49 (3H, s); 2.40 (3H, s).

EXAMPLE 125

N-[2,4-bis(methylthio)-6-methyl-3-pyridyl]-α-(4-methoxy-benzylthio)-4-methoxy-phenylacetamide According to a similar procedure to that described in Example 90, the titled compound was prepared.

m.p., 168.0°–169.5°

¹H NMR (300 MHz): δ8.02 (1H, s); 7.40 (2H, d, J=8.79 Hz); 7.32 (2H, d, J=8.42 Hz); 6.87 (4H, d, J=8.79 Hz); 6.65 (1H, s); 4.52 (1H, s); 4.00 (2H, dd, J=13.18, 46.88 Hz); 3.81 (3H, s); 3.79 (3H, s); 2.52 (3H, s); 2.49 (3H, s); 2.40 (3H, s).

EXAMPLE 135

N-[2,4-bis(methylthio)-6-methyl-3-pyridyl]-α-phenylthio-4-methoxy-phenylacetamide According to a similar procedure to that described in Example 90, the titled compound was prepared.

m.p., 165.0°–166.5°

¹H NMR (300 MHz): δ7.88 (1H, s); 7.51 (2H, d, J=8.79 Hz); 7.48–7.45 (2H, m); 7.32–7.24 (3H, m); 6.90 (2H, d, J=8.79 Hz); 6.59 (1H, s); 5.13 (1H, s); 3.81 (3H, s); 2.45 (3H, s); 2.43 (3H, s); 2.32 (3H, s).

EXAMPLE 136

N-[2,4-bis(methylthio)-6-methyl-3-pyridyl]-α-(4-fluoro-phenylthio)-4-methoxy-phenylacetamide According to a similar procedure to that described in Example 90, the titled compound was prepared.

m.p., 182.3°

$^1$H NMR (300 MHz): δ7.59 (1H, s); 7.45 (2H, d, J=4.76 Hz); 7.44 (2H, d, J=4.76 Hz); 6.98 (2H, d, J=8.42 Hz); 6.88 (2H, d, J=8.79 Hz); 6.59 (1H, s); 5.01 (1H, s); 3.80 (3H, s); 2.45 (3H, s); 2.44 (3H, s); 2.32 (3H, s).

EXAMPLE 137

N-[2,4-bis(methylthio)-6-methyl-3-pyridyl]-α-(4-methoxy-phenylthio)-4-methoxy-phenylacetamide According to a similar procedure to that described in Example 90, the titled compound was prepared.

m.p., 154.4°

$^1$H NMR (300 MHz): δ7.68 (1H, s); 7.44 (2H, d, J=6.96 Hz); 7.41 (2H, d, J=6.96 Hz); 6.87 (2H, d, J=8.79 Hz); 6.80 (2H, d, J=8.79 Hz); 6.59 (1H, s); 4.95 (1H, s); 3.80 (3H, s); 3.77 (3H, s); 2.45 (3H, s); 2.44 (3H, s); 2.33 (3H, s).

EXAMPLE 146

N-[2,4-bis(methylthio)-6-methyl-3-pyridyl]-α-O-methyl-4-methoxymandeloamide

Part 1.

To a stirred solution of 4-methoxymandelic acid (10.6 g) in methanol (150 ml) was added concentrated sulfuric acid (1.6 ml), and the mixture was refluxed for 3.5 hours. After cooling it was concentrated to about 70 ml and partitioned between methylene chloride and water. The organic layer was separated and washed sturated sodium bicarbonate, water and brine. It was dried (magnesium sulfate) and evaporated to give a mixture of methyl 4-methoxymandelate and methyl α-O-methyl-4-methoxymandelate as an oil. The residue was separated by column chromatography on silica gel with elution by 3:7 ethyl acetate-hexane to give 11 g of methyl 4-methoxymandelate and 2.4 g of methyl α-O-methyl-4-methoxymandelate as oils.

Part 2.

According to a similar procedure to that described in Part 4 of Example 40, the titled compound (0.175 g) was prepared from methyl α-O-methyl-4-methoxymandelate (0.196 g).

m.p., 130°–131°

$^1$H NMR (300 MHz): δ7.94 (1H, s); 7.46 (2H, d, J=8.79 Hz); 6.91 (2H, d, J=8.42 Hz); 6.62 (1H, s); 4.76 (1H, s); 3.80 (3H, s); 3.50 (3H, s); 2.49 (3H, s); 2.47 (3H, s); 2.36 (3H, s).

EXAMPLE 147

N-(2,6-diisopropyl-phenyl)-α-O-methyl-4-methoxymandeloamide

According to a similar procedure to that described in Example 146, the titled compound was prepared.

m.p., 165°–165.5°

$^1$H NMR (300 MHz): δ7.88 (1H, s); 7.42 (2H, d, J=8.42 Hz); 7.22 (1H, s); 7.12 (2H, d, J=7.69); 6.91 (2H, d, J=8.79 Hz); 4.77 (1H, s); 3.81 (3H, s); 3.48 (3H, s); 1.15 (6H, d, J=6.96 Hz); 1.06 (6H, d, J=6.96).

EXAMPLE 148

N-[2,4-bis(methylthio)-6-methyl-3-pyridyl]-α-hexylthio-4-fluoro-phenylacetamide

Part 1.

A solution of 4-fluorophenylacetic acid (9.7 g), N-bromosuccinimide (11.2 g) and azobisisobutyronitrile (AIBN, 0.2 g) in carbontetrachloride (100 ml) was reluxed for 2 hours. After cooling it was filtered through Celite® and the filtrate was evaporated to give an oily residue of α-bromo-4-fluorophenylacetic acid, which was used for next step without purification.

Part 2.

The α-bromo-4-fluorophenylacetic acid from Part 1 was dissolved in methanol (100 ml) and was added Dowex-50X-400® (2.7 g) to the solution. The mixture was refluxed for 6 hours and the resin was removed by filtering through Celite® after cooling. The filtrate was evaporated to give an oily residue, which was purified by column chromatography on silica gel with elution by 1:9 ethyl acetate-hexane to afford methyl α-bromo-4-fluorophenylacetate (87% yield).

Part 3.

To a stirred suspension of sodium hydride (0.114 g) in dry tetrahydrofuran (15 ml) was added hexanethiol (0.69 ml) dropwise, and the mixture was stirred for 1 hour at room temperature. Then a solution of methyl α-bromo-4-fluorophenylacetate (1 g) in tetrahydrofuran (15 ml) was added dropwise, and the mixture was stirred for 5 hours at room temperature. The reaction was quenched with saturated ammonium chloride and the product was extracted with ethyl ether. The extract was washed with water and brine, dried (magnesium sulfate) and evaporated to give an oily residue. Column chromatography on silica gel with elution by 5:95 ethyl acetate-hexane provided pure methyl α-hexylthio-4-fluorophenylacetate (0.7 g), a compound of Formula 4 wherein, X is S, $R^5$ is 4-fluorophenyl and $R^7$ is hexyl.

Part 4.

According to a similar procedure to that described in Part 4 of Example 40, the titled compound (0.143 g) was prepared from methyl α-hexylthio-4-fluorophenylacetate (0.34 g).

m.p., 149°–150°

$^1$H NMR (300 MHz): δ8.20 (1H, s), 7.52 (2H, dd, J=6.96, 5.50 Hz), 7.04 (2H, t, J=8.79 Hz), 6.63 (1H, s), 4.69 (1H, s), 2.84 (2H, t, J=6.96 Hz), 2.49 (3H, s), 2.47 (3H, s), 2.37 (3H, s), 1.68 (2H, m), 1.40 (2H, m), 1.30–1,26 (4H, m), 0.87 (3H, t, J=6.59 Hz).

EXAMPLE 152

N-[2,4-bis(methylthio)-6-methyl-3-pyridyl]-α-benzylthio-4-fluoro-phenylacetamide According to a similar procedure to that described in Example 148, the titled compound was prepared.

m.p., 188.5°–190.0°

$^1$H NMR (300 MHz): δ8.03 (1H, s), 7.46–7.27 (6H, m), 7.01 (2H, t, J=8.79 Hz), 6.65 (1H, s), 4.53 (1H, s), 4.12 (1H, d, J=13.18 Hz), 3.97 (1H, d, J=13.18 Hz), 2.51 (3H, s), 2.48 (3H, s), 2.39 (3H, s).

EXAMPLE 153

N-[2,4-bis(methylthio)-6-methyl-3-pyridyl]-α-(4-fluoro-benzylthio)-4-fluoro-phenylacetamide Part 1.

Same as Part 1 of Example 148.

Part 2.

Same as Part 1 of Example 148.

Part 3.

To a stirred solution of methyl α-bromo-4-fluorophenylacetate (1 g) and 4-fluorobenzylthiol (0.69 g) in dry methylene chloride (10 ml) was added 1,8-diazabicyclo[5.4.0]undec-7-ene (DBU, 0.91 ml) dropwise, and the mixture was stirred for 30 minutes at room temperature After cooling to 0°, 7 ml of 1N HCl was added dropwise and the product was extracted with ethyl ether. The extract was washed with water and brine, dried (magnesium sulfate) and evaporated to give an oily residue. Column chromatography on silica gel with elution by 5:95 ethyl acetate-hexane provided pure methyl α-(4-fluoro)-benzylthio-4-fluorophenylacetate (0.75 g), a compound of Formula 4 wherein, X is S, $R^5$ is 4-fluorophenyl and $R^7$ is 4-fluoro-benzyl.
Part 4.

According to a similar procedure to that described in Part 4 of Example 148, the titled compound was prepared.
m.p., 186°–188°
$^1$H NMR (300 MHz): δ8.00 (1H, s), 7.45 (2H, dd, J=8.42, 5.49 Hz), 7.36 (2H, dd, J=8.42, 5.49 Hz), 7.03 (4H, t, J=8.42 Hz), 6.65 (1H, s), 4.52 (1H, s), 4.11 (1H, d, J=13.18 Hz), 3.94 (1H, d, J=13.18 Hz), 2.52 (3H, s), 2.49 (3H, s), 2.39 (3H, s).

EXAMPLE 154

N-[2,4-bis(methylthio)-6-methyl-3-pyridyl]-α-(4-methoxy-benzylthio)-4-fluoro-phenylacetamide According to a similar procedure to that described in Example 148, the titled compound was prepared.
m.p., 182°–183°
$^1$H NMR (300 MHz): δ8.11 (1H, s), 7.43 (2H, dd, J=8.42, 5.13 Hz), 7.30 (2H, d, J=8.79 Hz), 7.01 (2H, t, J=8.79 Hz), 6.86 (2H, d, J=8.42 Hz), 6.65 (1H, s), 4.51 (1H, s), 4.08 (1H, d, J=13.18 Hz), 3.92 (1H, d, J=13.18 Hz), 3.80 (3H, s), 2.51 (3H, s), 2.48 (3H, s), 2.39 (3H, s).

EXAMPLE 165

N-[2,4-bis(methylthio)-6-methyl-3-pyridyl]-α-phenylthio-4-fluoro-phenylacetamide According to a similar procedure to that described in Example 148, the titled compound was prepared.
m.p., 156°–158°
$^1$H NMR (300 MHz): δ7.92 (1H, s), 7.53 (2H, dd, J=8.79, 5.13 Hz), 7.45 (2H, d, J=6.59 Hz), 7.31–7.23 (3H, m), 7.01 (2H, t, J=8.79 Hz), 6.58 (1H, s), 5.12 (1H, s), 2.44 (3H, s), 2.43 (3H, s), 2.31 (3H, s).

EXAMPLE 166

N-[2,4-bis(methylthio)-6-methyl-3-pyridyl]-α-(4-fluoro-phenylthio)-4-fluoro-phenylacetamide According to a similar procedure to that described in Example 153, the titled compound was prepared.
m.p., 172.5°–174°
$^1$H NMR (300 MHz): δ7.68 (1H, s), 7.52–7.42 (4H, m), 7.04 (2H, t, J=8.79 Hz), 6.99 (2H, t, J=8.79 Hz), 6.60 (1H, s), 5.03 (1H, s), 2.46 (3H, s), 2.45 (3H, s), 2.34 (3H, s).

EXAMPLE 167

N-[2,4-bis(methylthio)-6-methyl-3-pyridyl]-α-(4-methoxy-phenylthio)-4-fluoro-phenylacetamide According to a similar procedure to that described in Example 148, the titled compound was prepared.
m.p., 171.5°–173°

$^1$H NMR (300 MHz): δ7.76 (1H, s), 7.45 (2H, dd, J=8.79, 5.49 Hz), 7.39 (2H, d, J=8.79 Hz), 7.01 (2H, t, J=8.79 Hz), 6.80 (2H, d, J=8.79 Hz), 6.60 (1H, s), 4.95 (1H, s), 3.77 (3H, s), 2.45 (6H, s), 2.33 (3H, s).

EXAMPLE 176

N-[2,4-bis(methylthio)-6-methyl-3-pyridyl]-α-hexylthio-3,4-dichloro-phenylacetamide Part 1.

According to a similar procedure to that described in Part 1 of Example 148 α-bromo-3,4-dichloro-phenylacetic acid was prepared from 3,4-dichlorophenylacetic acid.
Part 2.

According to a similar procedure to that described in Part 2 of Example 148 methyl α-bromo-3,4-dichloro-phenylacetate was prepared from α-bromo-3,4-dichloro-phenylacetic acid.
Part 3.

According to a similar procedure to that described in Part 3 of Example 148 methyl α-hexylthio-3,4-dichloro-phenylacetate was prepared from methyl α-bromo-3,4-dichloro-phenylacetate.
Part 4.

To a stirred solution of methyl α-hexylthio-3,4-dichloro-phenylacetate (0.197 g) in tetrahydrofuran (10 ml) were added a solution of lithium hydroxide monohydrate (0.123 g) in water (10 ml) and methanol (10 ml), and the mixture was continued to stir for 2 hours at room temperature. At the end of the stirring it was evaporated to remove the organic solvents and the residue was partitioned between methylene chloride and 1N HCl. The organic layer was separated, washed with brine, dried (sodium sulfate) and evaporated to give an oily residue of α-hexylthio-3,4-dichloro-phenylacetic acid (0.179 g).
Part 5.

To a stirred solution of α-hexylthio-3,4-dichloro-phenylacetic acid (0.179 g) and N,N-dimethylformamide (0.01 ml) in dry methylene chloride at 0° was added a 2M solution of oxalyl chloride in methylene chloride (0.52 ml), and the mixture was continued to stir for 2 hours at room temperature. Then all the volatiles removed by evaporation, and the residue and 3-amino-2,4-bis(methylthio)-6-methyl-pyridine (0.209 g) were dissolved in methylene chloride (10 ml). The solution was cooled to 0° and triethylamine (0.33 ml) was added dropwise. It was stirred at room temperature for 16 hours and partitioned between methylene chloride and 1N sodium hydroxide. The organic layer was separated, washed with water and brine, dried (sodium sulfate) and evaporated to give an oily residue. Purification by column chromatography on silica gel provided the titled compound as white solid.
$^1$H NMR (300 MHz): δ8.28 (1H, s), 7.72 (1H, d, J=1.8 Hz), 7.45–7.38 (2H, m), 6.66 (1H, s), 4.65 (1H, s), 2.88–2.83 (2H, m), 2.52 (3H, s), 2.49 (3H, s), 2.40 (3H, m), 1.72–1.66 (2H, m), 1.44–1.27 (6H, m), 0.89 (3H, t, J=6.6 Hz).
Mass spectrum (NH$_3$-Cl/DDIP): m/e 503.0 (M+H)$^+$.

EXAMPLE 180

N-[2,4-bis(methylthio)-6-methyl-3-pyridyl]-α-benzylthio-3,4-dichloro-phenylacetamide According to a similar procedure to that described in Example 176 the titled compound was prepared.

¹H NMR (300 MHz): δ8.17 (1H, s), 7.62 (1H, d, J=2.2 Hz), 7.41–7.26 (7H, m), 6.67 (1H, s), 4.47 (1H, s), 4.14 (1H, d, J=13.2 Hz), 3.99 (1H, d, J=13.2 Hz), 2.54 (3H, s), 2.50 (3H, s), 2.42 (3H, s).

Mass spectrum (NH$_3$-CI/DDIP): m/e 509.0 (M+H)$^+$.

High resolution mass spectrum (NH$_3$-CI/DEP): calculated for C$_{23}$H$_{23}$Cl$_2$N$_2$OS$_3$ (M+H)$^+$, 509.034959; found, 527.034680.

EXAMPLE 181

N-[2,4-bis(methylthio)-6-methyl-3-pyridyl]-α-(4-fluoro-benzylthio)-3,4-dichloro-phenylacetamide According to a similar procedure to that described in Example 176 the titled compound was prepared.

¹H NMR (300 MHz): δ8.08 (1H, s), 7.62 (1H, d, J=2.2 Hz), 7.42–7.26 (4H, m), 7.07–7.01 (2H, m), 6.67 (1H, s), 4.45 (1H, s), 4.12 (1H, d, J=13.6 Hz), 3.96 (1H, d, J=13.6 Hz), 2.54 (3H, s), 2.50 (3H, s), 2.42 (3H, s).

Mass spectrum (NH$_3$-CI/DDIP): m/e 527.0 (M+H)$^+$.

High resolution mass spectrum (NH$_3$-CI/DEP): calculated for C$_{23}$H$_{22}$FN$_2$OS$_3$Cl$_2$ (M+H)$^+$, 527.025538; found, 527.024304.

EXAMPLE 182

N-[2,4-bis(methylthio)-6-methyl-3-pyridyl]-α-(4-methoxy-benzylthio)-3,4-dichloro-phenylacetamide According to a similar procedure to that described in Example 176 the titled compound was prepared.

¹H NMR (300 MHz): δ8.20 (1H, s), 7.61 (1H, d, J=2.2 Hz), 7.39 (1H, d, J=8.4 Hz), 7.32–7.28 (3H, m), 6.90–6.87 (2H, m), 6.67 (1H, s), 4.46 (1H, s), 4.11 (1H, d, J=13.2 Hz), 3.95 (1H, d, J=13.2 Hz), 3.82 (3H, s), 2.54 (3H, s), 2.50 (3H, s), 2.42 (3H, s).

Mass spectrum (NH$_3$-CI/DDIP): m/e 539.0 (M+H)$^+$.

High resolution mass spectrum (NH$_3$-CI/DEP): calculated for C$_{24}$H$_{25}$N$_2$O$_2$S$_3$Cl$_2$ (M+H)$^+$, 539.045524; found, 539.044122.

EXAMPLE 204

N-[2,4-bis(methylthio)-6-methyl-3-pyridyl]-α-hexylthio-2,4-difluoro-phenylacetamide Part 1.

According to a similar procedure to that described in Part 1 of Example 1 methyl 2,4-difluoromandelate was prepared from 2,4-difluoromandelic acid.

Part 2.

To a stirred solution of methyl 2,4-difluoromandelate (0.42 g) and triethylamine (0.87 ml) in dry methylene chloride (5 ml) at 0° was added dropwise methanesulfonyl chloride (0.161 ml), and the mixture was stirred for 40 minutes at 0°–20°. At the end of the stirring were hexanethiol (0.322 ml) and 1,8-diazabicyclo[5.4.0]undec-7-ene (DBU, 0.622 ml) and the mixture was stirred for 3 hours at room temperature. It was then partitioned between ethyl acetate and water, the organic layer was washed with water, 1N-HCl and water. It was dried (magnesium sulfate) and evaporated to give an oily residue. Purification by column chromatography on silica gel with elution by 5:95 ethyl acetate-hexane provided pure methyl α-hexylthio-2,4-difluoro-phenylacetate, a compound, of formula 4 wherein X is R$^5$ is 2 4-difluorophenyl and R$^7$ is hexyl.

Part 3.

According to a similar procedure to that described in Part 4 of Example 40 the titled compound was prepared.
m.p., 138°–139°

¹H NMR (300 MHz): δ8.37 (1H, s), 7.62 (1H, dt, J=6.23, 8.42 Hz), 6.92–6.80 (2H, m), 6.65 (1H, s), 4.96 (1H, s), 2.83 (2H, m), 2.51 (3H, s), 2.48 (3H, s), 2.40 (3H, s), 1.67 (2H, m), 1.40 (2H, m), 1.29 (4H, m), 0.87 (3H, t, J=6.60 Hz).

EXAMPLE 210

N-[2,4-bis(methylthio)-6-methyl-3-pyridyl]-α-(4-methoxy-benzylthio)-2,4-difluoro-phenylacetamide According to a similar procedure to that described in Example 204 the titled compound was prepared.
m.p., 147.5°–148°

¹H NMR (300 MHz): δ8.21 (1H, s), 7.58 (1H, dt, J=6.23, 8.42 Hz), 7.30 (2H, d, J=8.79 Hz), 6.89–6.76 (2H, m), 6.86 (2H, d, J=8.79 Hz), 6.66 (1H, s), 4.80 (1H, s), 4.07 (1H, d, J=12.82 Hz), 3.92 (1H, d, J=12.82 Hz), 3.80 (3H, s), 2.52 (3H, s), 2.49 (3H, s), 2.41 (3H, s).

EXAMPLE 232

N-[2,4-bis(methylthio)-6-methyl-3-pyridyl]-α-hexylthio-3,4-dimethoxy-phenylacetamide Part 1.

According to a similar procedure to that described in Part 1 of Example 032 α-bromo-3,4-dimethoxy-phenylacetic acid was prepared from 3,4-dimethoxyphenylacetic acid.

Part 2.

The α-bromo-3,4-dimethoxyphenylacetic acid (7 g) was dissolved in methanol (100 ml) and was added Dowex-50X-400® (1 g) to the solution. The mixture was refluxed for 5 hours and the resin was removed by filtering through Celite® after cooling. The filtrate was evaporated to give a mixture of methyl α-bromo-3,4-dimethoxyphenylacetate and methyl α-methoxy-3,4-dimethoxyphenylacetate as an oily residue, which were separated by a column chromatography on silica gel with elution by 2:8 ethyl acetate-hexane.

Part 3.

To a stirred solution of methyl α-methoxy-3,4-dimethoxyphenylacetate (0.39 g) in methylene chloride (5 ml) were added hexanethiol (0.35 ml) and 3 drops of concentrated sulfuric acid and the mixture was stirred for 30 minutes. Then it was washed with water and brine, dried (magnesium sulfate) and evaporated to give an oily residue. Purification by column chromatography on silica gel with elution by 1:9 ethyl acetate-hexane provided methyl α-hexylthio-3,4-dimethoxyphenylacetate (0.37 g), a compound of Formula 4 wherein X is S, R$^5$ is 3,4-dimethoxyphenyl and R$^7$ is hexyl.

Part 4.

According to a similar procedure to that described in Part 4 of Example 40 the titled compound was prepared.

¹H NMR (300 MHz): δ8.09 (1H, s); 7.22–7.08 (2H, m); 6.84 (1H, d, 1H); 6.63 (1H, s); 4.67 (1H, s); 3.90 (3H, s); 3.86 (3H, s); 2.82 (2H, t, J=7.32 Hz); 2.48 (3H, s); 2.47 (3H, s); 2.36 (3H, s); 1.709–1.62 (2H, m); 1.52–1.23 (6H, m); 0.89–0.84 (3H, m).

EXAMPLE 236

N-[2,4-bis(methylthio)-6-methyl-3-pyridyl]-α-benzylthio-3,4-dimethoxy-phenylacetamide According to a similar procedure to that described in Example 232 the titled compound was prepared.

¹H NMR (300 MHz): δ7.94 (1H, s); 7.40–7.25 (5H, m); 6.99–6.98 (2H, m); 6.82–6.79 (1H, m); 6.41 (1H, s); 4.52 (1H, S); 4.09 (1H, d, J=12.82 Hz; A of AB); 3.95 (1H, d, J=13.18 Hz, B of AB); 3.86–3.85 (6H, m); 2.497 (3H, s); 2.493 (3H, s); 2.47 (3H, s).

EXAMPLE 237

N-[2,4-bis(methylthio)-6-methyl-3-pyridyl]-α-(4-fluoro-benzylthio)-3,4-dimethoxy-phenylacetamide According to a similar procedure to that described in Example 232 the titled compound was prepared.

¹H NMR (300 MHz): δ7.82 (1H, s); 7.38 (2H, m); 7.04–6.98 (4H, m); 6.81 (1H, d, J=8.79 Hz); 6.64 (1H, s); 4.49 (1H, s); 4.08 (1H, d, J=13.55 Hz, A of AB); 3.92 (1H, d, J=13.18 Hz, B of AB); 3.87 (1H, s); 3.85 (1H, s); 2.49 (1H, s); 2.47 (1H, s); 2.38 (1H, s).

EXAMPLE 260

N-[2,4-bis(methylthio)-6-methyl-3-pyridyl]-α-hexylthio-4-butoxy-phenylacetamide

Part 1.

According to a similar procedure to that described in Part 1 of Example 148, α-bromo-4-butoxy-phenylacetic acid was prepared from 4-butoxyphenylacetic acid.

Part 2.

The α-bromo-4-butoxyphenylacetic acid (4.1 g) was dissolved in methanol (150 ml) and was added Dowex-50X-400® (0.5 g) to the solution. The mixture was refluxed for 5 hours and the resin was removed by filtering through Celite® after cooling. The filtrate was evaporated to give a mixture of methyl α-bromo-4-butoxyphenylacetate and methyl α-methoxy-4-butoxyphenylacetate as an oily residue, which was used for next step without separation.

Part 3.

According to a similar procedure to that described in Part 3 of Example 232, methyl α-hexylthio-4-butoxyphenylacetate was prepared from the mixture of methyl α-bromo-4-butoxyphenylacetate and methyl α-methoxy-4-butoxyphenylacetate, prepared as described in Part 2.

Part 4.

According to a similar procedure to that described in Part 4 of Example 40 the titled compound was prepared.

m.p., 131.2°

¹H NMR (300 MHz): δ8.08 (1H, s); 7.45 (2H, d, J=8.79 Hz); 6.88 (2H, d, J=8.79 Hz); 6.62 (1H, s); 4.67 (1H, s); 3.94 (2H, t, J=6.59 Hz); 2.81 (2H, d, J=8.79 Hz); 2.48 (1H, s); 2.45 (1H, s); 2.36 (1H, s); 1.77–1.65 (4H, m); 1.51–1.31 (4H, m); 1.29–1.25 (4H, m); 0.96 (3H, t, J=7.32 Hz); 0.87 (3H, t, J=6.77 Hz).

EXAMPLE 264

N-[2,4-bis(methylthio)-6-methyl-3-pyridyl]-α-benzylthio-4-butoxy-phenylacetamide According to a similar procedure to that described in Example 260 the titled compound was prepared.

m.p., 154.2°

¹H NMR (300 MHz): δ7.94 (1H, s); 7.40–7.26 (7H, m); 6.84 (1H, d, J=8.79 Hz); 6.64 (1H, s); 4.52 (1H, s); 4.09 (1H, d, J=13.18 Hz, A of AB); 3.94 (1H, d, J=13.18 Hz, B of AB); 3.95–3.92 (2H, m); 2.50 (1H, s); 2.47 (1H, s); 2.38 (1H, s); 1.76–1.71 (2H, m); 1.51–1.43 (2H, m); 0.95 (3H, t, J=7.32 Hz).

EXAMPLE 265

N-[2,4-bis(methylthio)-6-methyl-3-pyridyl]-α-benzylthio-4-butoxy-phenylacetamide According to a similar procedure to that described in Example 260 the titled compound was prepared.

m.p., 161.6°

¹H NMR (300 MHz): δ7.86 (1H, s); 7.39–7.34 (4H, m); 7.01 (2H, t, J=8.61 Hz); 6.87 (1H, d, J=8.79 Hz); 6.65 (1H, s); 4.50 (1H, s); 4.08 (1H, d, J=13.18 Hz, A of AB); 3.97–3.89 (3H, m); 2.51 (3H, s); 2.48 (3H, s); 2.39 (3H, s); 1.78–1.73 (2H, m); 1.54–1.46 (2H, m); 0.96 (3H, t, J=7.32 Hz).

EXAMPLE 288

N-[2,4-bis(methylthio)-6-methyl-3-pyridyl]-α-hexylthio-4-phenoxy-phenylacetamide According to a similar procedure to that described in Example 176 the titled compound was prepared.

¹H NMR (300 MHz): δ8.21 (1H, s), 7.53 (2H, d, J=8.4 Hz), 7.36–7.31 (2H, m), 7.13–7.08 (1H, m), 7.02–6.99 (4H, m), 6.64 (1H, s), 4.72 (1H, s), 2.89–2.84 (2H, m), 2.50 (3H, s), 2.48 (3H, s), 2.39 (3H, s), 1.75–1.64 (2H, m), 1.47–1.30 (6H, m), 0.89 (3H, t, J=6.6 Hz).

Mass spectrum (NH₃-CI/DDIP): m/e 527.2 (M+H)⁺.

EXAMPLE 292

N-[2,4-bis(methylthio)-6-methyl-3-pyridyl]-α-benzylthio-4-phenoxy-phenylacetamide According to a similar procedure to that described in Example 176 the titled compound was prepared.

¹H NMR (300 MHz): δ7.92 (1H, s), 7.46–7.43 (2H, m), 7.36–7.26 (7H, m), 7.13–7.08 (1H, m), 7.01–6.96 (4H, m), 6.66 (1H, s), 4.52 (1H, s), 4.11 (1H, d, J=13.2 Hz), 3.93 (1H, d, J=13.2 Hz), 2.52 (3H, s), 2.49 (3H, s), 2.40 (3H, s).

EXAMPLE 295

N-[2,4-bis(methylthio)-6-methyl-3-pyridyl]-α-(4-chloro-benzylthio)-4-phenoxy-phenylacetamide According to a similar procedure to that described in Example 176 the titled compound was prepared.

¹H NMR (300 MHz): δ8.09 (1H, s), 7.46–6.95 (13H, m), 6.66 (1H, s), 4.56 (1H, s), 4.14 (1H, d, J=13.2 Hz), 4.00 (1H, d, J=13.2 Hz), 2.52 (3H, s), 2.50 (3H, s), 2.41 (3H, s).

EXAMPLE 316

N-[2,4-bis(methylthio)-6-methyl-3-pyridyl]-α-hexylthio-3-phenoxy-phenylacetamide Part 1.

According to a similar procedure to that described in Part 1 of Example 148, 3-phenoxyoxyphenylacetic acid was bominated to give a mixture of α-bromo-3-phenoxy-phenylacetic acid and bromo-3-(4'-bromophenoxy)-phenylacetic acid (ratio, about 4:1).

Part 2.

The mixture of α-bromo-3-phenoxy-phenylacetic acid and α-bromo-3-(4'-bromophenoxy)-phenylacetic acid (3.26 g) was dissolved in methanol (30 ml) and was added conc. sulfuric acid (10 drops) to the solution. The mixture was refluxed for 4 hours and neutralized with sat'd sodium bicarbonate after cooling. Concentration followed by extraction with ethyl acetate and evaporation gave a mixture of methyl α-bromo-3-phenoxy-phenylacetate and methyl α-bromo-3-(4'-bromophenoxy)-phenylacetate as an oily residue, which was used for next step without separation.
Part 3.

According to a similar procedure to that described in Part 3 of Example 148, a mixture of methyl α-hexylthio-3-phenoxy-phenylacetate and methyl α-hexylthio-3-(4'-bromophenoxy)-phenylacetate was prepared from the mixture of methyl α-bromo-3-phenoxy-phenylacetate and methyl α-bromo-3-(4'-bromophenoxy)-phenylacetate, prepared in Part 2.
Part 4.

According to a similar procedure to that described in Part 4 of Example 176, a mixture of α-hexylthio-3-phenoxy-phenylacetic acid and α-hexylthio-3-(4'-bromophenoxy)-phenylacetic acid was prepared from the mixture of methyl α-hexylthio-3-phenoxy-phenylacetate and methyl α-hexylthio-3-(4'-bromophenoxy)-phenylacetate, prepared in Part 3.
Part 5.

According to a similar procedure to that described in Part 5 of Example 176, a mixture of the titled compound and N-[2,4-bis(methylthio)-6-methyl-3-pyridyl]-α-hexylthio-3-(4'-bromophenoxy)-phenylacetoamide (Example 055) was prepared from the mixture of α-hexylthio-3-phenoxy-phenylacetic acid and α-hexylthio-3-(4'-bromo-phenoxy)-phenylacetic acid, prepared in Part 4. The two products were separated by column chromatography on silica gel with elution by 1:9 ethyl acetate-hexane (ratio, about 4:1).

$^1$H NMR (300 MHz): δ8.20 (1H, s), 7.34–7.28 (5H, m), 7.11–7.06 (1H, m), 7.01 (2H, d, J=7.69 Hz), 6.97–6.93 (1H, m), 4.68 (1H, s), 2.87–2.82 (2H, m), 2.48 (3H, s), 2.47 (3H, s), 2.34 (3H, s), 1.74–1.62 (2H, m), 1.46–1.24 (6H, m), 0.88 (3H, t, J=6.6 Hz).

Mass spectrum (NH$_3$-CI/DDIP): m/e 527.2 (M+H)$^+$.

EXAMPLE 317

N-[2,4-bis(methylthio)-6-methyl-3-pyridyl]-α-hexylthio-3-(4'-bromophenoxy)-phenylacetamide The titled compound was obtained as a minor product during the preparation of N-[2,4-bis(methylthio)-6-methyl-3-pyridyl]-α-hexylthio-3-phenoxy-phenylacetoamide (Example 316).

$^1$H NMR (300 MHz): δ8.24 (1H, s), 7.41 (2H, d, J=8.79 Hz), 7.35–7.33 (2H, m), 7.26 (1H, s), 6.95–6.92 (1H, m), 6.89 (2H, d, J=8.79 Hz), 6.64 (1H, s), 4.68 (1H, s), 2.88–2.83 (2H, m), 2.48 (3H, s), 2.47 (3H, s), 2.35 (3H, s), 1.74–1.63 (2H, m), 1.46–1.29 (6H, m), 0.88 (3H, t, J=6.6 Hz).

Mass spectrum (NH$_3$-CI/DDIP): m/e 605.607 (M+H)$^+$.

EXAMPLE 321

N-[2,4-bis(methylthio)-6-methyl-3-pyridyl]-α-benzylthio-3-phenoxy-phenylacetamide According to a similar procedure to that described in Example 316 the titled compound N-[2,4-bis(methylthio)-6-methyl-3-pyridyl]-α-benzylthio-3-(4'-bromophenoxy)-phenylacetoamide (minor product, Example 322) were prepared.

$^1$H NMR (300 MHz): δ8.08 (1H, s), 7.40–7.20 (10H, m), 7.11–7.06 (1H, m), 7.00–6.91 (3H, m), 6.64 (1H, s), 4.53 (1H, s), 4.12 (1H, d, J=13.2 Hz), 3.99 (1H, d, J=13.2 Hz), 2.49 (6H, s), 2.36 (3H, s).

EXAMPLE 322

N-[2,4-bis(methylthio)-6-methyl-3-pyridyl]-α-benzylthio-3-(4'-bromophenoxy)-phenylacetamide The titled compound was obtained as a minor product during the preparation of N-[2,4-bis(methylthio)-6-methyl-3-pyridyl]-α-benzylthio-3-phenoxy-phenylacetoamide (Example 321).

$^1$H NMR (300 MHz): δ8.13 (1H, s), 7.43–7.17 (10H, m), 6.94–6.85 (3H, m), 6.65 (1H, s), 4.53 (1H, s), 4.13 (1H, d, J=13.2 Hz), 3.99 (1H, d, J=13.2 Hz), 2.49 (6H, s), 2.37 (3H, s).

EXAMPLE 325

N-[2,4-bis(methylthio)-6-methyl-3-pyridyl]-α-(4-chloro-benzylthio)-3-phenoxy-phenylacetamide According to a similar procedure to that described in Example 316 the titled compound N-[2,4-bis(methylthio)-6-methyl-3-pyridyl]-α-(4-chloro)benzylthio-3-(4'-bromophenoxy)-phenylacetoamide (minor product, Example 326) were prepared.

$^1$H NMR (300 MHz): δ7.91 (1H, s), 7.35–6.92 (13H, m), 6.64 (1H, s), 4.49 (1H, s), 4.09 (1H, d, J=13.2 Hz), 3.92 (1H, d, J=13.2 Hz), 2.49 (6H, s), 2.36 (3H, s).

EXAMPLE 326

N-[2,4-bis(methylthio)-6-methyl-3-pyridyl]-α-(4-chloro-benzylthio)-3-(4'-bromophenoxy)-phenylacetamide The titled compound was obtained as a minor product during the preparation of N-[2,4-bis(methylthio)-6-methyl-3-pyridyl]-α-(4-chloro)benzylthio-3-phenoxy-phenylacetoamide (Example 325).

$^1$H NMR (300 MHz): δ7.97 (1H, s), 7.44–7.18 (9H, m), 6.95–6.85 (3H, m), 6.65 (1H, s), 4.49 (1H, s), 4.10 (1H, d, J=13.2 Hz), 3.93 (1H, d, J=13.2 Hz), 2.49 (6H, s), 2.37 (3H, s).

EXAMPLE 347

N-[2,4-bis(methylthio)-6-methyl-3-pyridyl]-α-hexylthio-2-phenoxy-phenylacetamide According to a similar procedure to that described in Example 176 the titled compound was prepared.

$^1$H NMR (300 MHz): δ8.43 (1H, s), 7.72 (1H, dd, J=7.7, 1.2 Hz), 7.36–7.30 (2H, m), 7.25–7.06 (5H, m), 6.87 (1H, dd, J=8.1, 1.5 Hz), 6.65 (1H, s), 5.19 (1H, s), 2.88–2.70 (2H, m), 2.50 (3H, s), 2.49 (3H, s), 2.39 (3H, s), 1.68–1.56 (2H, m), 1.40–1.18 (6H, m), 0.84 (3H, t, J=6.6 Hz).

Mass spectrum (NH$_3$-CI/DDIP): m/e 527.0 (M+H)$^+$.

High resolution mass spectrum (NH$_3$-CI/DEP): calculated for $C_{28}H_{35}N_2O_2S_3$ (M+H)$^+$, 527.186069; found, 527.186079.

EXAMPLE 375

N-[2,4-bis(methylthio)-6-methyl-3-pyridyl]-α-hexylthio-4-trifluoromethyl-phenylacetamide According to a similar procedure to that described in Example 204 the titled compound was prepared.

m.p., 174°–175°

$^1$H NMR (300 MHz): δ8.31 (1H, s), 7.66 (2H, t, J=8.79 Hz), 7.62 (2H, t, J=8.06 Hz), 6.64 (1H, s), 4.74 (1H, s), 2.89–2.83 (2H, m), 2.50 (3H, s), 2.48 (3H, s), 2.38 (3H, s), 1.68 (2H, m), 1.45–1.37 (2H, m), 1.33–1.26 (4H, m), 0.87 (3H, t, J=6.96 Hz).

EXAMPLE 379

N-[2,4-bis(methylthio)-6-methyl-3-pyridyl]-α-benzylthio-4-trifluoromethyl-phenylacetamide According to a similar procedure to that described in Example 90 the titled compound was prepared.

m.p., 203°–203.5°

$^1$H NMR (300 MHz): δ8.22 (1H, s), 7.58 (4H, s), 7.41–7.30 (4H, m), 6.67 (! H, s), 4.59 (1H, s), 4.16 (1H, d, J=13.19 Hz), 4.00 (1H, d, J=13.19 Hz), 2.53 (3H, s), 2.50 (3H, s), 2.41 (3H, s).

EXAMPLE 380

N-[2,4-bis(methylthio)-6-methyl-3-pyridyl]-α-(4-fluoro-benzylthio)-4-trifluoromethyl-phenylacetamide According to a similar procedure to that described in Example 90 the titled compound was prepared.

m.p., 201.5°–203°

$^1$H NMR (300 MHz): δ8.12 (1H, s), 7.59 (4H, s), 7.37 (2H, dd, J=8.42, 5.13 Hz), 7.04 (2H, t, J=8.60 Hz), 6.66 (1H, s), 4.56 (1H, s), 4.19 (1H, d, J=13.18 Hz), 3.96 (1H, d, J=13.18 Hz), 2.53 (3H, s), 2.50 (3H, s), 2.41 (3H, s).

EXAMPLE 381

N-[2,4-bis(methylthio)-6-methyl-3-pyridyl]-α-(4-methoxy-benzylthio)-4-trifluoromethyl-phenylacetamide According to a similar procedure to that described in Example 204 the titled compound was prepared.

m.p., 190.5°–192°

$^1$H NMR (300 MHz): δ8.24 (1H, s), 7.58 (4H, s), 7.32 (2H, d, J=8.42 Hz), 6.88 (2H, d, J=8.42 Hz), 6.67 (1H, s), 4.57 (1H, s), 4.12 (1H, d, J=13.18 Hz), 3.96 (1H, d, J=13.18 Hz), 3.82 (3H, s), 2.53 (3H, s), 2.50 (3H, s), 2.41 (3H, s).

EXAMPLE 393

N-[2,4-bis(methylthio)-6-methyl-3-pyridyl]-α-(4-fluoro-phenylthio)-4-trifluoromethyl-phenylacetamide According to a similar procedure to that described in Example 90 the titled compound was prepared.

m.p., 217.5°–219°

$^1$H NMR (300 MHz): δ7.81 (1H, s), 7.62 (4H, s), 7.46 (2H, dd, J=8.79, 5.13 Hz), 7.00 (2H, t, J=8.79 Hz), 6.61 (1H, s), 5.06 (1H, s), 2.47 (3H, s), 2.46 (3H, s), 2.35 (3H, s).

EXAMPLE 394

N-[2,4-bis(methylthio)-6-methyl-3-pyridyl]-α-(4-methoxy-phenylthio)-4-trifluoromethyl-phenylacetamide According to a similar procedure to that described in Example 90 the titled compound was prepared.

m.p., 187°–189°

$^1$H NMR (300 MHz): δ7.90 (1H, s), 7.41 (2H, d, J=8.79 Hz), 6.82 (2H, d, J=8.79 Hz), 6.62 (1H, s), 4.99 (1H, s), 3.79 (3H, s), 2.47 (6H, s), 2.36 (3H, s).

EXAMPLE 403

N-[2,4-bis(methylthio)-6-methyl-3-pyridyl]-α-hexylthio-4-isopropylphenylacetamide Part 1.

To a stirred suspension of 4-isopropylbenzaldehyde (21.4 g) and sodium cyanide (6.9 g) in water (25 ml) at 0° was added saturated sodium bisulfite (40 ml) dropwise over a period of 30 minutes. During the addition about 50 g of ice was also added in small portions. After the addition the mixture was warmed up to room temperature gradually. Resulting waxy 4-isopropylmandelonitrile was separated by decantation and the aqueous layer was extracted with benzene. The benzene extract was evaporated and, the residue was combined with the waxy material. The 4-isopropylmandelonitrile was dissolved in concentrated hydrochloric acid (25 ml) and the mixture was stirred at room temperature overnight. It was then stirred in a 100° oil bath for 3 hours. After cooling was added water to dissolve the solid material and the product was extracted with ethyl ether throughly. The combined extracts were washed with brine, dried (sodium sulfate) and evaporated to give 4-isopropylmandelic acid as an oil (17 g).

Part 2.

To a solution of 4-isopropylmandelic acid (17 g) in methanol (150 ml) was added Dowex-50X-400® and the mixture was refluxed for 4 hours. After cooling it was filtered through Celite® and the filtrate was evaporated to give a syrupy residue of methyl 4-isopropylmandelate (18.9 g), which solidified upon storing at room temperature.

Part 3.

To a solution of methyl 4-isopropylmandelate (18.9 g) and triethylamine (12.7 ml) in dry methylene chloride (50 ml) at 0° was added methanesulfonyl chloride (7.2 ml) dropwise, and the mixture was stirred for 1 hr at 0°–25°. At end of the stirring it was diluted with methylene chloride (150 ml), and washed with water, 1N-HCl, water and brine. After drying (magnesium sulfate), it was evaporated to give an oily residue. Column chromatography on silica gel with elution by 1:9 ethyl acetate-hexane provided the desied methyl α-O-methanesulfonyl-4-isopropylmandelate (17.6 g).

Part 4.

According to a similar procedure to that described in Part 3 of Example 90 methyl α-hexylthio-4-isopropylmandeloamide (185 mg) was prepared from methyl α-O-methanesulfonyl-4-isopropylmandelate (290 mg)

Part 5.

According to a similar procedure to that described in Part 4 of Example 40, the titled compound (50.8 mg) was prepared from methyl α-hexylthio-4-isopropylmandeloamide (171 mg)

m.p., 109°–110°

¹H NMR (300 MHz): δ8.17 (1H, s); 7.48 (2H, d, J=8.06 Hz); 7.22 (2H, d, J=8.42 Hz); 6.64 (1H, s); 4.71 (1H, s); 2.92–2.82 (3H, m); 2.49 (3H, s); 2.47 (3H, s); 2.37 (3H, s);1.72–1.63 (2H, m); 1.46–1.36 (2H, m);1.31–1.18 (4H, m); 1.25 (3H, s); 1.22 (3H, s); 0.88 (3H, t, J=6.59 Hz).

EXAMPLE 407

N-[2,4-bis(methylthio)-6-methyl-3-pyridyl]-α-benzylthio-4-isopropylphenylacetamide According to a similar procedure to that described in Example 403, the titled compound was prepared.
m.p., 184°–185°
¹H NMR (300 MHz): δ8.04 (1H, s); 7.41–7.24 (7H, m); 7.19 (2H, d, J=8.42 Hz); 6.65 (1H, s); 4.55 (1H, s); 4.14 (1H, d, J=13.18 Hz, A of AB); 3.99 (1H, d, J=13.18 Hz, B of AB); 2.90–2.86 (1H, m); 2.51 (3H, s); 2.49 (3H, s); 2.39 (3H, s); 1.23 (3H, s); 1.21 (3H, s).

EXAMPLE 410

N-[2,4-bis(methylthio)-6-methyl-3-pyridyl]-α-(4-chloro-benzylthio)-4-isopropylphenylacetamide According to a similar procedure to that described in Example 403, the titled compound was prepared.
m.p., 189°–190.5°
¹H NMR (300 MHz): δ7.85 (1H, s); 7.39 (2H, d, J=8.06 Hz); 7.32 (4H, quartet, J=8.60, 13.92 Hz); 7.20 (2H, d, J=8.06 Hz); 6.46 (1H, s); 4.51 (1H, s); 4.10 (1H, d, J=13.18Hz, A of AB); 3.92 (1H, d, J=13.55 Hz, B of AB); 2.91–2.86 (1H, m); 2.51 (3H, s); 2.49 (3H, s); 2.39 (3H, s); 1.23 (3H, s); 1.21 (3H, s).

EXAMPLE 411

N-[2,4-bis(methylthio)-6-methyl-3-pyridyl]-α-(4-butoxy-benzylthio)-4-isopropylphenylacetamide According to a similar procedure to that described in Example 403, the titled compound was prepared.
m.p., 159°–161°
¹H NMR (300 MHz): δ8.09 (1H, s); 7.39 (2H, d, J=8.03 Hz); 7.30 (2H, d, J=8.42 Hz); 7.19 (2H, d, J=8.06 Hz); 6.85 (2H, d, J=8.42 Hz); 6.64 (1H, s); 4.54 (1H, s); 4.33 (1H, d, J=13.18 Hz, A of AB); 3.95 (1H, d, J=12.82 Hz, B of AB); 2.92–2.83 (1H, m); 2.51 (3H, s); 2.48 (3H, s); 2.38 (3H, s); 1.81–1.72 (2H, m); 1.56–1.43 (2H, m); 1.23 (3H, s); 1.21 (3H, s); 0.98 (3H, t, J=7.32 Hz).

EXAMPLE 431

N-[2,4-bis(methylthio)-6-methyl-3-pyridyl]-α-hexylthio-4-tert-butylphenylacetamide Part 1.
A solution of methyl 4-tert-butylphenylacetate (3.0 g), 1,3-dibromo-5,5-dimethylhydantoin (3.28 g) and azobisisobutyronitrile (AIBN, 0.01 g) in carbon tetrachloride (100 ml) was stirred in a 70° oil bath for hours. After cooling the mixture was filtered through Celite® and the filtrate was evaporated to give an oily residue of methyl α-bromo-4-tert-butylphenylacetate.
Part 2.
To a stirred solution of methyl α-bromo-4-tert-butylphenylacetate (0.42 g) and hexanethiol (0.25 ml) in dry methylene chloride (5 ml) was added 1,8-diazabicyclo[5.4.0]undec-7-ene (DBU, 0.33 ml) dropwise, and the mixture was stirred for 30 minutes at room temperature After cooling to 0°, 3 ml of 1N HCl was added dropwise and the product was extracted with ethyl ether. The extract was washed with water and brine, dried (magnesium sulfate) and evaporated to give an oily residue. Column chromatography on silica gel with elution by 5:95 ethyl acetate-hexane provided pure methyl α-hexylthio-4-tert-butylphenylacetate (0.38 g), a compound of Formula 4 wherein, X is S, $R^5$ is 4-tert-butylphenyl and $R^7$ is hexyl.
Part 3.
According to a similar procedure to that described in Part 4 of Example 40, the titled compound was prepared from α-hexylthio-4-tert-butylphenylacetate.
m.p., 144.5°
¹H NMR (300 MHz): δ8.18 (1H, s); 7.48 (2H, d, J=8.05 Hz); 7.37 (2H, d, J=8.42 Hz); 6.63 (1H, s); 4.71 (1H, s); 2.91–2.81 (2H, m); 2.49 (3H, s); 2.48 (3H, s); 2.37 (3H, s); 1.74–1.61 (2H, m); 1.51–1.37 (2H, m); 1.37–1.24 (13H, m); 0.883 (3H, t, J=6.77 Hz).

EXAMPLE 435

N-[2,4-bis(methylthio)-6-methyl-3-pyridyl]-α-benzylthio-4-tert-butylphenylacetamide According to a similar procedure to that described in Example 431, the titled compound was prepared.
m.p., 197.1°
¹H NMR (300 MHz): d 8.04 (1H, s); 7.41–7.28 (9H, m); 6.65 (1H, s); 4.56 (1H, s); 4.14 (1H, d, J=13.18 Hz, A of AB); 3.99 (1H, d, J=13.18 Hz, B of AB); 2.51 (3H, s); 2.49 (3H, s); 2.40 (3H, s); 1.29 (9H, s).

EXAMPLE 437

N-[2,4-bis(methylthio)-6-methyl-3-pyridyl]-α-(4-chloro-benzylthio)-4-tert-butylphenylacetamide According to a similar procedure to that described in Example 431, the titled compound was prepared.
m.p., 202.7°
¹H NMR (300 MHz): δ7.85 (1H, s); 7.42–7.28 (8H, m); 6.65 (1H, s); 4.52 (1H, s); 4.11 (1H, d, J=13.5 Hz, A of AB), 3.92 (1H, d, J=13.2 Hz, B of AB); 2.51 (3H, s); 2.49 (3H, s); 2.40 (3H, s); 1.30 (9H, s).

EXAMPLE 439

N-[2,4-bis(methylthio)-6-methyl-3-pyridyl]-α-(4-tert-butyl-benzylthio)-4-tert-butylphenylacetamide According to a similar procedure to that described in Example 431, the titled compound was prepared.
m.p., 202°–205°
¹H NMR (300 MHz): δ8.10 (1H, s); 7.42–7.31 (8H, m); 6.65 (1H, s); 4.59 (1H, s); 4.12 (1H, d, J=13.18 Hz, B of AB); 3.98 (1H, d, J=13.18 Hz, A of AB);; 2.51 (3H, s); 2.49 (3H, s); 2.39 (3H, s); 1.32 (9H, s); 1.29 (9H, s).

EXAMPLE 459

N-[2,4-bis(methylthio)-6-methyl-3-pyridyl]-α-hexylthio-4-biphenylacetamide

According to a similar procedure to that described in Example 153, the titled compound was prepared.

¹H NMR (300 MHz): δ8.24 (1H, s); 7.64–7.26 (9H, m); 6.63 (1H, s); 4.60 (1H, s); 2.90–2.84 (2H, m); 2.49 (3H, s); 2.48 (3H, s); 2.36 (3H, s); 1.73–1.67 (2H, m); 1.44–1.37 (2H, m); 1.33–1.25 (4H, m); 0.876 (3H, t, J=6.77 Hz.).

EXAMPLE 463

N-[2,4-bis(methylthio)-6-methyl-3-pyridyl]-α-benzylthio-4-biphenylacetamide

According to a similar procedure to that described in Example 153, the titled compound was prepared.

¹H NMR (300 MHz): δ8.11 (1H, s); 7.59–7.51 (6H, m); 7.45–7.26 (8H, m); 6.65 (1H, s); 4.60 (1H, s); 4.15 (1H, d, J=13.18 Hz, A of AB); 4.00 (1H, d, J=13.18 Hz, B of AB); 2.51 (3H, s), 2.48 (3H, s); 2.84 (3H, s).

EXAMPLE 464

N-[2,4-bis(methylthio)-6-methyl-3-pyridyl]-α-(4-fluoro-benzylthio)-4-biphenylacetamide According to a similar procedure to that described in Example 153, the titled compound was prepared.

m.p., 209°–211°

¹H NMR (300 MHz): δ7.99 (1H, s); 7.58–7.52 (6H, m); 7.52–7.32 (5H, m); 7.02 (2H, t, J=8.6 Hz); 6.65 (1H, s); 4.57 (1H, s); 4.13 (1H, d, J=13.18 Hz, A of AB); 3.96 (1H, d, J=13.18 Hz, B of AB); 2.51 (3H, s); 2.48 (3H, s); 2.39 (3H, s).

EXAMPLE 465

N-[2,4-bis(methylthio)-6-methyl-3-pyridyl]-α-(4-methoxy-benzylthio)-4-biphenylacetamide According to a similar procedure to that described in Example 153, the titled compound was prepared.

m.p., 194°–196°

¹H NMR (300 MHz): δ8.14 (1H, s); 7.57–7.51 (7H, m); 7.44–7.39 (2H, m); 7.33 (2H, d, J=8.79 Hz); 6.87 (1H, d, J=8.79 Hz); 6.65 (1H, s); 4.58 (1H, s); 4.18 (1H, d, J=13.18 Hz, A of AB); 3.96 (1H, d, J=13.18 Hz, B of AB); 3.81 (3H, s); 2.51 (3H, s); 2.48 (3H, s); 2.39 (3H, s).

EXAMPLE 467

N-[2,4-bis(methylthio)-6-methyl-3-pyridyl]-α-(4-butoxy-benzylthio)-4-biphenylacetamide According to a similar procedure to that described in Example 153, the titled compound was prepared.

m.p., 164.6°

¹H NMR (300 MHz): δ8.17 (1H, s); 7.58–7.53 (6H, m); 7.52–7.40 (2H, m); 7.36–7.31 (3H, m); 6.87 (2H, d, J=8.42 Hz); 6.66 (1H, s); 4.14 (1H, s); 4.12 (1H, d, J=13.18 Hz, A of AB); 3.97 (1H, d, J=13.18 Hz, B of AB); 2.52 (1H, s); 2.49 (1H, s); 2.40 (1H, s); 1.82–1.73 (2H, m); 1.60–1.45 (2H, m); 0.98 (3H, t, J=7.32 Hz).

EXAMPLE 484

N-[2,4-bis(methylthio)-6-methyl-3-pyridyl]-α-(3-pyridyl-methylthio)-4-biphenylacetamide According to a similar procedure to that described in Example 153, the titled compound was prepared.

m.p., 209°–211°

¹H NMR (300 MHz): δ8.648–8.642 (1H, m); 8.54–8.52 (1H, m); 7.83 (1H, s); 7.78–7.77 (1H, m); 7.59–7.55 (5H, m); 7.46–7.35 (3H, m); 6.66 (1H, s); 4.62 (1H, s); 4.41 (1H, d, J=13.18 Hz, A of AB); 3.99 (1H, d, J=13.18 Hz, B of AB); 2.51 (1H, s); 2.49 (1H, s); 2.39 (1H, s).

EXAMPLE 487

N-[2,4-bis(methylthio)-6-methyl-3-pyridyl]-α-hexylthio-4-nitro-phenylacetamide

According to a similar procedure to that described in Example 176 the titled compound was prepared.

m.p., 171°–172°.

¹H NMR (300 MHz): δ8.36 (1H, s) 8.24–8.21 (2H, m), 7.75–7.72 (2H, m), 6.66 (1H, s), 4.78 (1H, s), 2.91–2.83 (2H, m), 2.52 (3H, s), 2.50 (3H, s), 2.40 (3H, s), 1.75–1.59 (2H, m), 1.55–1.25 (6H, m), 0.89 (3H, t, J=6.6 Hz).

EXAMPLE 515

N-[2,4-bis(methylthio)-6-methyl-3-pyridyl]-α-hexylthio-3,4-methylenedioxyphenylacetamide According to a similar procedure to that described in Example 90 the titled compound was prepared from 3,4-methylenedioxymandelic acid.

¹H NMR (300 MHz): δ8.14 (1H, S ), 7.08–7.07 (1H, m), 7.04–7.01 (1H, m), 6.81–6.78 (1H, m), 6.64 (ill, s), 5.96 (2H, s), 4.64 (1H, s), 2.85–2.80 (2H, m), 2.50 (3H, s), 2.48 (3H, s), 2.39 (3H, s), 1.73–1.62 (2H, m), 1.45–1.27 (6H, m), 0.88 (3H, t, J=6.6 Hz).

Mass spectrum (NH₃-CI/DDIP): m/e 479.0 (M+H)⁺.

High resolution mass spectrum (NH₃-CI/DEP): calculated for $C_{23}H_{31}N_2O_3S_3$ (M+H)⁺, 479149684; found, 479.148384.

EXAMPLE 522

N-[2,4-bis(methylthio)-6-methyl-3-pyridyl]-α-(4-chloro-benzylthio)-3,4-methylenedioxyphenylacetamide According to a similar procedure to that described in Example 90 the titled compound was prepared from 3,4-methylenedioxymandelic acid.

¹H NMR (300 MHz): consistent with predicted structure.

EXAMPLE 543

N-[2,4-bis(methylthio)-6-methyl-3-pyridyl]-α-hexylthio-2-thienylacetamide

Part 1.

To a stirred solution of 2-thiopheneglyoxylic acid (1 g) in methanol (10 ml) was added 5 drops of concentrated sufuric acid and the mixture was refluxed for 4 hours. Then the methanol was evaporated off and the residue was partitioned between ethyl acetate and water. The organic extract was washed with water and brine, dried (sodium sulfate) and evaporated to give methyl 2-thiopheneglyoxylate as an oil (1.01 g).

Part 2.

To a stirred solution of methyl 2-thiopheneglyoxylate (1.01 g) in ethanol (20 ml) in an ice bath was added sodium borohydride (0.113 g) in 1 ml of water, and the mixture was stirred for 10 minutes. The reaction was quenched with aqueous acetic acid and the mixture was partitioned between methylene chloride and water. The organic extract was washed with brine, dried (sodium sulfate) and evaporated to give methyl α-hydroxy-2-thienylacetate as an oil (0.903 g).
Part 3.

According to a similar procedure to that described in part 2 of Example 204, methyl α-hexylthio-2-thienylacetate (0.93 g) was prepared from methyl α-hydroxy-2-thienylacetate (0.903 g).
Part 4.

According to a similar procedure to that described in part 4 of Example 176, α-hexylthio-2-thienylacetic acid (0.84 g) was prepared from methyl α-hexylthio-2-thienylacetate (0.93 g).
Part 5.

According to a similar procedure to that described in part 5 of Example 176, the titled compound (1.02 g) was prepared from α-hexylthio-2-thienylacetic acid (0.84 g). Recrstallization from ethyl acetate and hexane provided chromatographically pure compound.

m.p., 122.5°–123.5°

$^1$H NMR (300 MHz): δ7.93 (1H, s), 7.30–7.28 (2H, m), 7.01–6.98 (1H, m), 6.64 (1H, s), 4.98 (1H, s), 2.92–2.82 (2H, m), 2.50 (3H, s), 4.48 (3H, s), 2.39 (3H, s), 1.74–1.63 (2H, m), 1.46–1.38 (2H, m), 1.37–1.24 (4H, m), 0.88 (3H, t, J=6.6 Hz).

Mass spectrum (NH$_3$-CI/DDIP): m/e 441.0 (M+H)$^+$.

High resolution mass spectrum (NH$_3$-CI/DEP): calculated for $C_{20}H_{29}N_2O_1S_4$ (M+H)$^+$, 441.116276; found, 441.116449.

EXAMPLE 600

N-[2,4-bis(methylthio)-6-methyl-3-pyridyl]-α-hexylthio-4-butyl-phenylacetamide

According to a similar procedure to that described in Example 403, the titled compound was prepared.

m.p., 99.5°–100.5°

$^1$H NMR (300 MHz): δ8.14 (1H, s); 7.46 (2H, d, J=8.06); 7.17 (2H, d, J=8.06); 6.63 (1H, s); 4.70 (1H, s); 2.85 (2H, t, J=6.96); 2.60 (2H, t, J=7.69); 2.49 (3H, s); 2.48 (3H, s); 2.37 (3H, s); 1.72–1.60 (2H, m); 1.58–1.53 (2H, m); 1.43–1.35 (4H, m); 1.32–1.25 (4H, m); 0.91 (3H, t, J=7.32); 0.89 (3H, t, J=7.32).

EXAMPLE 607

N-[2,4-bis(methylthio)-6-methyl-3-pyridyl]-α-(4-chloro-benzylthio)-4-butyl-phenylacetamide According to a similar procedure to that described in Example 403, the titled compound was prepared.

m.p., 138.0°–140.0°

$^1$H NMR (300 MHz): δ7.82 (1H, s); 7.38 (2H, d, J=8.06); 7.34 (2H, d, J=8.79); 7.29 (2H, d, J=8.79); 7.16 (2H, d, J=8.06); 6.65 (1H, s); 4.51 (1H, s); 4.10(1H, d, J=13.18, A of AB); 3.91 (1H, d, J=13.18, B of AB); 2.59 (2H, t, J=7.32); 2.50 (3H, s); 2.49 (3H, s); 2.39 (3H, s); 1.60–1.52 (2H, m); 1.37–1.29 (2H, m); 0.91 (3H, t, J=7.32).

EXAMPLE 617

N-[2,4-bis(methylthio)-6-methyl-3-pyridyl]-α-(4-butyl-benzylthio)-4-butyl-phenylacetamide According to a similar procedure to that described in Example 403, the titled compound was prepared.

m.p., 135°–137°

$^1$H NMR (300 MHz): δ8.05 (1H, s); 7.38 (2H, d, J=8.06); 7.30 (2H, d, J=8.06); 7.14 (4H, d, J=8.06); 6.65 (1H, s); 4.56 (1H, s); 4.10 (1H, d, J=12.82,A of AB); 3.96 (1H, d, J=12.82, B of AB); 2.58 (4H, quartet, J$_1$=6.96, J2=14.65); 2.50 (3H, s); 2.49 (3H, s); 2.39 (3H, s); 1.64–1.51 (4H, m); 1.34 (4H, septet, J=7.51); 0.93 (3H, t, J=7.33); 0.91 (3H, t, J=7.33).

For the preparation of the compounds of Formula I wherein R$^3$ is CH$_2$XR$^4$, wherein R$^4$ is CH$_2$CHR$^{10}$R$^{11}$ and X is S, the method shown in Scheme 8 may be conveniently employed. Diethyl malonate may be deprotonated under relatively mild conditions, employing such conditions as sodium in ethanol or sodium hydride in dimethylsulfoxide. The sodium malonate may then be alkylated with an appropriate electrophile, such as a halide or psuedohalide compound (including iodides, bromides, chlorides, toluenesulfonates, methanesulfonates, etc.). Two identical or different groups may be incorporated into the structure of the product, compound (15). Bulky diethyl malonate compounds such as (15) may be hydrolyzed at one ester group using mild conditions, such as dilute ethanolic sodium hydroxide. The monoester compound (16) may then be decarboxylated, employing either high temperature or reagents such as piperidine or morpholine in solvents such as pyridine at reflux temperature. The ester compound (17) may be reduced to the substituted ethanol (18) using such reagents as lithium aluminum hydride, diisobutylalumnium hydride, etc.

Scheme 8

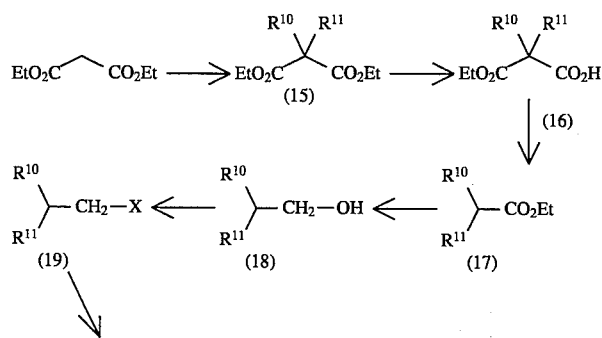

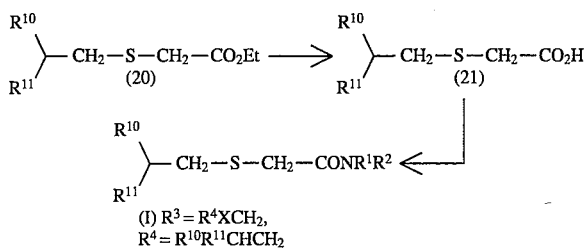

The sequence (15)–(18) may also proceed through the malonic acid analogue, available by stronger hydrolysis conditions applied to compound (15). The diacid is subjected to decarboxylation and reduction exactly as described above. The hydroxy group in compound (18) may then be converted to a halide or psuedohalide group for further synthesis. For example, the bromide may be prepared by treating the alcohol with such reagents as phosphorus tribromide, carbon tetrabromide/triphenylphosphine, etc. The halide group in compound (19) is then treated with a mercaptoacetic ester. This reaction may be performed with the salt of the mercaptan (formed with such reagents as sodium hydride, etc.), or the reaction may be performed in the presence of a base to buffer the reaction. Also, a catalyst such as a tetraalkylammonium iodide salt may be present to accelerate the reaction. The ester group on the sulfide compound (20) is then hydrolzyed to the acid compound (21). This may then be coupled to an appropriately-substituted amine to afford the compound of Formula I.

For the preparation of the compounds of Formula I wherein $R^3$ is $-CH_2XR^4$, and $R^4$ is the group $-CH_2CHR^{10}R^{11}$, and $R^9$ is a phenyl, substituted phenyl, or heteroaromatic group, the method shown in Scheme 9 may be conveniently employed. An arylacetonitrile compound (22) may be alkylated at the benzylic carbon atom using such conditions as sodium hydride in dimethylsulfoxide, followed by an alkyl halide or psuedohalide. The alkylated nitrile compound (23) may then be hydrolyzed to the carboxylic ester (24) or acid (25), depending on the conditions used. Typically, refluxing 6N aqueous hydrochloric or sulfuric acid will effect this transformation. The ester (24), if prepared, can then be hydrolyzed to the acid (25) using conditions like sodium hydroxide in alcoholic solvent. Either the ester (24) or the acid (25) may be reduced to the hydroxymethyl compound (26), using reagents such as borane•tetrahydrofuran, lithium aluminum hydride, etc. The hydroxyl group may be then be converted to halide or psuedohalide to give compound (27). This compound may then be used to alkylate ethyl thioglycolate, employing conditions such as potassium carbonate in dimethylformamide. The sulfide ester (28) may then be converted to the amide compound of Formula I using the techniques discussed above.

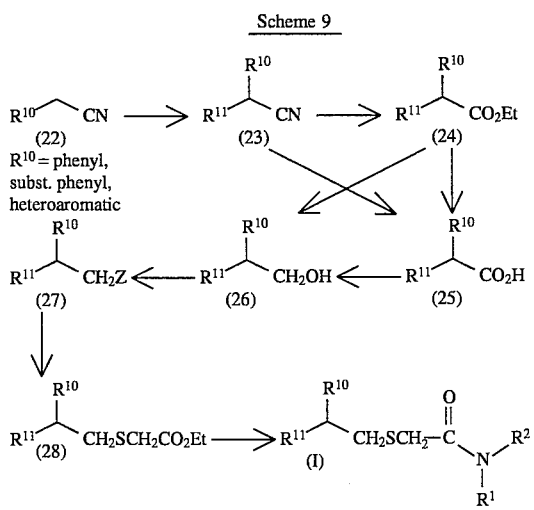

Scheme 9

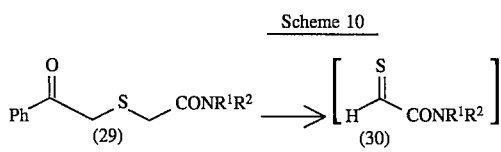

Scheme 10

-continued
Scheme 10

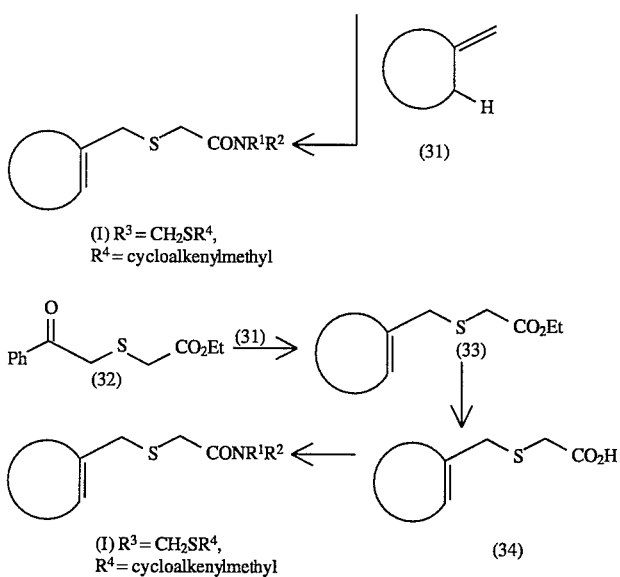

(I) R³ = CH₂SR⁴,
R⁴ = cycloalkenylmethyl

For the compounds of Formula I wherein $R^3$ is $CH_2XR^4$ and $R^4$ is a cycloalkenylmethyl or bicycloalkenylmethyl group, a method involving the "ene" reaction of a thioaldehyde and a methylene-substituted cycloalkane may be conveniently used (Scheme 10). For example, a phenacylthioacetamide of the type (29) undergoes a facile cleavage reaction when irradiated with visible light (270 W sun lamp), generating the thioformyl carboxamide (30) in situ. This route in analogous to the chemistry employed by Vedejs, et al., *J. Org. Chem.*, v. 53., p. 2220 (1988). The thioaldehyde compound is a very reactive intermediate, and will undergo an ene reaction with methylenecycloalkanes of the type (31) to give exclusively the allyl sulfide compound. Alternatively, the ester-substituted compound (32) may be treated in a similar manner to that above to give the ester compound (33). The ester group may be hydrolyzed to the acid compound (34) using reagents such as sodium hydroxide, etc. The acid may then be coupled to an appropriately-substituted amine as discussed earlier to give the final product.

Scheme 11

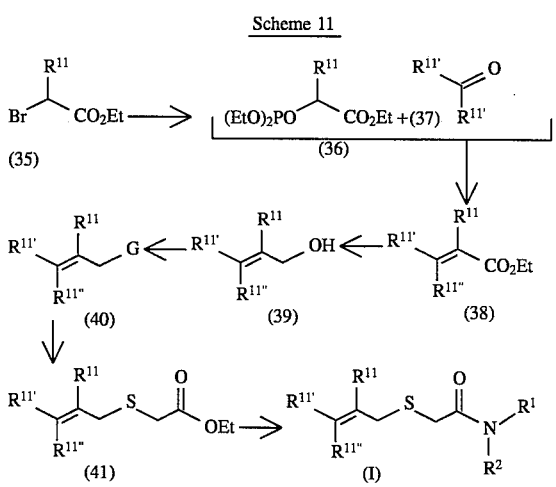

Preparation of the compounds of Formula I wherein $R^3$ is $CH_2XR^4$, X is S, and $R^4$ is a substituted allyl group, may be accomplished according to the method shown in Scheme 11.

An appropriately-substituted α-bromoester XX is subjected to the conditions of the Arbuzov reaction (trialkylphosphite, heat), to give the phosphonate compound (36). This is then treated with a base, such as sodium hydride. The salt then is allowed to react with a carbonyl compound of formula (37), to give the unsaturated ester compound (38). Double bond stereoisomers at this point may be separated, and taken on separately in the rest of the synthesis. Reduction of the ester group with a reagent like diisobutylaluminum hydride gives the allylic alcohol compound (39). The hydroxyl group is converted to a leaving group (G) to give compound (40). This is allowed to react with a mercaptoacetate under basic conditions (potassium carbonate, for example), which generates the sulfide ester (41). Conversion of the ester group to an amide is performed in the usual way, thus affording the specified compounds of Formula I.

The detailed processes for preparing the compounds of Formula I are illustrated by the following examples. It is, however, understood that this invention is not limited to the specific details of these examples. Melting points are uncorrected. All the temperatures are reported in Celsius. Proton nuclear magnetic resonance spectra ($^1$H NMR) were measured in chloroform-d ($CDCl_3$) unless otherwise specified and the peaks are reported in parts per million (ppm) downfield from tetramethylsilane (TMS). The coupling patterns are reported as follows: s, singlet; d, doublet; t, triplet; q, quartet; qt, quintet; m, multiplet.

EXAMPLE 1005

N-[2,4-bis(methylthio)-6-methylpyridin-3-yl]-2-(2-butyldecylthio)-acetamide

Part 1.

A mixture of sodium hydride (50% w/w suspension in mineral oil, 2.40 g, 50.0 mmol) in dimethylsulfoxide (50 mL) was cooled to 5° C., and a solution of diethyl butylmalonate (10.0 mL, 45.5 mmol) in dimethylsulfoxide (10 mL) was added dropwise with vigorous stirring. After 4 hours, the solution was treated with iodooctane (8.20 mL, 44.3 mmol), and the solution was stirred an additional 12 hours. It was poured into water (400 mL), and extracted with ethyl acetate (2×500 mL). The extracts were washed in sequence with water (3×400 mL), then saturated brine (400 mL). The extracts were then combined, dried over anhydrous magnesium sulfate, filtered and evaporated. The resulting oil was separated by flash chromatography (3:97 ethyl acetate-hexane) to afford the product, diethyl butyl-octylmalonate, as an oil (13.7 g, 41.7 mmol, 94%).

$^1$H NMR (300 MHz): δ4.17 (4H, q, J=7.0 Hz); 1.91–1.81 (4H, m); 1.37–1.07 (22H, m); 0.90 (3H, t, J=7.3 Hz); 0.88 (3H, t, J=7.0 Hz).

Mass spectrum (NH$_3$-CI/DDIP): m/z 330 (20%); 329 (98%); 327 (47%); 255 (100%).

Part 2.

The diester from Part 1 above (13.7 g, 41.7 mmol) was dissolved in 95% ethanolic sodium hydroxide (400 mL, 0.25M, 100 mmol), and heated to reflux overnight. The solution was cooled and evaporated. The residue was acidified to pH 5 with 1N hydrochloric acid, and extracted with ethyl acetate (2×200 mL). The extracts were combined, dried over anhydrous magnesium sulfate, filtered and evaporated. The resulting solid represented sufficiently pure product, monoethyl butyloctylmalonate (12.6 g, 41.7 mmol, 100%).

m.p., 95°–97°

$^1$H NMR (300 MHz): δ4.29 (2H, q, J=7.3 Hz); 2.00–1.91 (4H, m); 1.39–1.18 (19H, m); 0.90 (3H, t, J=7.0 Hz); 0.87 (3H, t, J=7.0 Hz).

Mass spectrum (NH$_3$-CI/DDIP): m/z 318 (33%); 302 (19%); 301 (100%); 257 (23%); 246 (21%).

Part 3.

A solution of the acid from Part 2 above (12.6 g, 41.7 mmol) and morpholine (5.00 mL, 57.2 mmol) in pyridine (30 mL), and the solution was heated to reflux for 14 hours. The solution was cooled and evaporated, and the residue was taken up in methylene chloride (250 mL). This solution was washed with 1N hydrochloric acid (3×200 mL), and the organic phase was dried over anhydrous magnesium sulfate, filtered and evaporated. The resulting oil represented sufficiently pure product, ethyl 2-butyldecanoate (10.35 g, 40.4 mmol, 97%).

$^1$H NMR (300 MHz): δ4.13 (2H, q, J=7.3 Hz); 2.40–2.29 (1H, m); 1.70–1.58 (2H, m); 1.56–1.41 (2H, m); 1.39–1.20 (19H, m); 0.89 (3H, t, J=6.6 Hz); 0.88 (3H, t, J=7.0 Hz).

Mass spectrum (NH$_3$-CI/DDIP): m/z 258 (2%); 257 (11%); 229 (100%).

Part 4.

A solution of lithium aluminum hydride in tetrahydrofuran (100 mL, 1.0M, 100 mmol) was cooled to 0° C., and treated dropwise with a solution of the ester prepared in Part 3 above (10.3 g, 40.4 mmol) in tetrahydrofuran (30 mL). After stirring for 16 hours and warming to ambient temperature, the solution was recooled to 0° C., and quenched by the slow, sequential addition of 4 mL water/12 mL 15% aqueous sodium hydroxide/12 mL water. The resulting mixture was filtered through a short column of celite, then dried over anhydrous magnesium sulfate, filtered and evaporated. The resulting oil represented sufficiently pure product, 2-butyl-1-decanol (8.89 g).

$^1$H NMR (300 MHz): δ3.54 (2H, t, J=5.3 Hz); 1.50–1.18 (22H, m); 0.90 (3H, t, J=6.6 Hz); 0.86 (3H, t, J=6.6 Hz).

Part 5.

A solution of phosphorus tribromide (1.50 mL, 15.8 mmol) and pyridine (0.60 mL, 7.42 mmol) in benzene (30 mL) was cooled to 0° C., and a solution of the alcohol prepared in Part 4 above (8.89 g) and pyridine (0.3 mL, 3.71 mmol) was added dropwise. The solution was stirred for 40 hours, then poured over ice (150 g) and allowed to melt. This mixture was extracted with ether (2×200 mL), and the extracts were combined, dried over anhydrous magnesium sulfate, filtered and evaporated to afford 1-bromo-2-butyl-decane as an oil (5.63 g, 20.3 mmol, 49%).

$^1$H NMR (300 MHz): δ3.45 (2H, d, J=4.8 Hz); 1.68–1.58 (1H, m); 1.43–1.20 (20H, m); 0.91 (3H, t, J=6 Hz); 0.90 (3H, t, J=6 Hz).

Part 6.

A solution of the bromide prepared in Part 5 above (5.63 g, 20.3 mmol), ethyl mercaptoacetate (2.30 mL, 21.0 mmol), potassium carbonate (3.19 g, 23.1 mmol) and tetra-n-butylammonium iodide (1.60 g, 4.33 mmol) in tetrahydrofuran (40 mL) was heated to reflux for 14 hours. The solution was cooled, poured into water (200 mL), and extracted with methylene chloride (2×200 mL). The extracts were combined, dried over anhydrous magnesium sulfate, filtered and evaporated. The residual oil was separated by flash chromatography (1:19 ethyl acetate-hexane) to afford the product, ethyl 2-(2-butyldecylthio)acetate, as an oil (4.97 g, 15.7 mmol, 77%).

$^1$H NMR (300 MHz): δ4.19 (2H, q, J=7.0 Hz); 3.18 (2H, s); 2.61 (2H, d, J=6.2 Hz); 1.60–1.51 (1H, m); 1.40–1.20 (23H, m); 0.90 (3H, t, J=6.2 Hz); 0.88 (3H, t, J=7.0 Hz).

Mass spectrum (NH$_3$-CI/DDIP): m/z 344 (100%); 318 (12%); 317 (59%); 229 (1%).

Part 7.

A solution of the ester prepared in Part 6 above (3.97 g, 12.5 mmol) and sodium hydroxide (1.05 g, 26.3 mmol) in 95% ethanol (100 mL) was stirred at ambient temperature for 14 hours. The solution was evaporated, and the residue was acifified to pH 5 with 1N hydrochloric acid. This mixture was diluted to 250 mL with water, and extracted with ethyl acetate (2×250 mL). The extracts were combined, dried over anhydrous magnesium sulfate, filtered and evaporated to afford the product, 2-(2-butyldecylthio)acetic acid, as an oil (3.25 g, 11.3 mmol, 90%).

$^1$H NMR (300 MHz): δ3.23 (2H, s); 2.64 (2H, d, J=6.2 Hz); 1.62–1.51 (1H, m); 1.40–1.20 (20H, m); 0.90 (3H, t, J=6.6 Hz); 0.88 (3H, t, J=7.0 Hz).

Mass spectrum (NH$_3$-CI/DDIP): m/z 307 (19%); 306 (100%); 289 (12%).

Part 8.

A solution of the acid prepared in Part 7 above (3.25 g, 11.3 mmol) and 2 drops dimethylformamide in methylene chloride (20 mL) was treated with a solution of oxalyl chloride in methylene chloride (16.9 mL, 2.0M, 33.8 mmol). After stirring for 12 hours, the solution was evaporated. A portion of the residue (1.73 g) was taken up in tetrahydrofuran (10 mL). This solution was added to an ice-cooled solution of 3-amino-2,4-bis(methylthio)-6-methylpyridine (1.12 g, 5.59 mmol) and potassium carbonate (0.94 g, 6.8 mmol) in tetrahydrofuran (20 mL). The solution was stirred for 12 hours, then poured into water (200 mL) and extracted with methylene chloride (2×200 mL). The extracts were combined, dried over anhydrous sodium sulfate, filtered and evaporated. The residual material was separated by flash chromatography to afford the title product as a solid, recrystalized from ether (1.73 g, 3.67 mmol, 66%).

m.p., 78°–79°

$^1$H NMR (300 MHz): δ8.25 (1H, br s); 6.67 (1H, s); 3.39 (2H, s); 2.77 (2H, d, J=6.6 Hz); 2.52 (3H, s); 2.50 (3H, s); 2.42 (3H, s); 1.70–1.60 (1H, m); 1.42–1.20 (20H, m); 0.89 (3H, t, J=7 Hz); 0.88 (3H, t, J=7.0 Hz).

$^{13}$C NMR (300 MHz, CDCl$_3$): δ168.0, 157.0, 156.3, 148.4, 123.4, 113.8, 38.7, 37.7, 37.0, 33.3, 32.9, 31.9, 30.0, 29.6, 29.3, 28.8, 26.6, 24.3, 23.0, 22.7, 20.9, 14.1, 14.0, 12.8.

IR (KBr): 3234, 2956, 2924, 2854, 1662, 1564, 1536, 1506, 1436, 1340, 808 cm$^{-1}$.

Mass spectrum (NH$_3$-CI/DDIP): m/z 473 (17%); 472 (29%); 471 (100%).

Elemental analysis: calculated C 61.23, H 8.99, N 5.95; observed C 61.37, H 9.00, N 5.93.

EXAMPLE 1022

N-[2,4-bis(methylthio)-6-methylpyridin-3-yl]-1-(2-phenylheptylthio)acetamide

Part 1.

Sodium hydride (2.2 g of 50% w/w slurry in mineral oil, 47.0 mmol) was washed with hexane and dried under vacuum. Dimethylsulfoxide (40 mL) was added, and the mixture was stirred and cooled in an ice bath while a solution of benzyl cyanide (5.0 g, 42.7 mmol) in dimethylsulfoxide (10 mL) was added dropwise. The ice bath was removed, and the solution was allowed to stir for 4 hours. The deep red solution was then cooled again to 0° C., and a solution of 1-iodopentane (5.60 mL, 42.7 mmol) in dimethyl-sulfoxide (10 mL) was added dropwise. The mixture was stirred and allowed to come to ambient temperature over 12 hours. It was poured into water (200 mL), and extracted with ethyl acetate (2×200 mL). The extracts were washed in sequence with water (3×200 mL), then combined, dried over anhydrous magnesium sulfate, filtered and evaporated. The oily residue was separated by column chromatography (3:97 ethyl acetate-hexane) to afford the product, 2-phenylheptanenitrile, as a clear oil (4.41 g, 23.5 mmol, 55%).

$^1$H NMR (300 MHz): δ7.40–7.28 (5H, m); 3.77 (1H, dd, J=8.4, 6.6 Hz); 2.00–1.80 (2H, m); 1.59–1.40 (2H, m); 1.39–1.22 (4H, m); 0.88 (3H, t, J=6.7 Hz).

Part 2.

A solution of the nitrile from Part 1 above (4.41 g, 23.5 mmol) in ethanol (1 mL) was treated with a solution prepared from concentrated sulfuric acid (3.30 mL) and water (4.70 mL). This mixture was heated to reflux for 12 hours, then cooled and poured over ice (100 g). After the mixture was allowed to melt, it was extracted with ethyl acetate (2×100 mL). The extracts were combined, dried over anhydrous magnesium sulfate, filtered and evaporated. The residual oil (4.73 g) gave a $^1$H NMR spectrum consistent with a 1:2 mixture of ethyl 2-phenylheptanoate and 2-phenylheptanoic acid.

Part 3.

A solution of the mixture of compounds prepared in Part 2 above in tetrahydrofuran (20 mL) was added dropwise to an ice-cooled slurry of lithium aluminum hydride (1.83 g, 48.3 mmol) in tetrahydrofuran (30 mL). The ice bath was removed, and the resulting solution was warmed to reflux for 12 hours. The mixture was again cooled to 0° C., and quenched by the addition of 2 mL water, 6 mL 15% aqueous sodium hydroxide, and 6 mL water. The resulting mixture was filtered through celite, dried over anhydrous potassium carbonate, filtered and evaporated to afford the product, 2-phenylheptanol, as a clear, colorless oil (4.19 g, 21.8 mmol, 99%).

$^1$H NMR (300 MHz): δ7.37–7.14 (5H, m); 3.79–3.64 (2H, m); 2.82–2.71 (1H, m); 1.75–1.51 (2H, m); 1.34–1.13 (6H, m); 0.84 (3H, t, J=6 Hz).

Part 4.

A solution of the alcohol prepared in Part 3 above (4.19 g, 21.8 mmol) and carbon tetrabromide (9.39 g, 28.3 mmol) in tetrahydrofuran (35 mL) was cooled to 0° C. and a solution of triphenylphosphine (7.43 g, 28.3 mmol) in tetrahydrofuran (20 mL) was added dropwise. After stirring overnight and warming to ambient temperature, the solution was evaporated, and the residual oil was separated by flash chromatography (1:9 ethyl acetate-hexane) to afford the product, 1-bromo-2-phenylheptane (5.26 g, 20.6 mmol, 95%).

$^1$H NMR (300 MHz): δ7.40–7.15 (5H, m); 3.55 (2H, d, J=7.0 Hz); 2.97–2.87 (1H, m); 1.96–1.85 (1H, m); 1.68–1.57 (1H, m); 1.33–1.12 (6H, m); 0.83 (3H, t, J=6.6 Hz).

Part 5.

A solution of the bromide prepared in Part 4 above (5.26 g, 20.6 mmol), thiolacetic acid (1.60 mL, 22.7 mmol), potassium carbonate (3.42 g, 24.7 mmol) and tetra-n-butylammonium iodide (1.52 g, 4.12 mmol) in tetrahydrofuran (40 mL) was stirred at ambient temperature overnight. The mixture was poured into water (100 mL), and extracted with methylene chloride (2×100 mL). The extracts were combined, dried over anhydrous magnesium sulfate, filtered and evaporated. The residual oil was purified by elution through a plug of silica gel with 1:9 ethyl acetate-hexane, and evaporation gave the product, 2-phenyl-1-thioacetyl-heptane, as an oil (4.24 g, 16.9 mmol, 82%).

$^1$H NMR (300 MHz): δ7.32–7.12 (5H, m); 3.23 (1H, dd, J=13.2, 4.6 Hz); 3.05 (1H, dd, J=13.2, 8.4 Hz); 2.78–2.68 (1H, m); 2.27 (3H, s); 1.80–1.70 (1H, m); 1.68–1.58 (1H, m); 1.30–1.09 (6H, m); 0.83 (3H, t, J=6.6 Hz).

Mass spectrum (NH$_3$-CI/DDIP): m/z 269 (23%); 268 (100%); 251 (32%).

Part 6.

A solution of the thioacetate from Part 5 above (4.24 g, 16.9 mmol) in 95% ethanol (150 mL) at 0° C. was treated with sodium hydroxide (1.50 g, 37.2 mmol), and the mixture was stirred for 14 hours. The solution was evaporated, and the residue was taken up into water (100 mL) and acidified to pH 5 with 1N hydrochloric acid. This mixture was then extracted with methylene chloride (2×100 mL), and the extracts were combined, dried over anhydrous magnesium sulfate, filtered and evaporated. The oily residue was purified by elution through a plug of silica gel with 1:19 ethyl acetate-hexane, and evaporation gave the product, 1-mercapto-2-phenylheptane, as an oil (3.13 g, 15.0 mmol, 89%).

$^1$H NMR (300 MHz): δ7.38–7.09 (5H, m); 2.90–2.65 (3H, m); 1.88–1.77 (1H, m); 1.67–1.54 (1H, m); 1.35–1.09 (6H, m); 0.83 (3H, t, J=6 Hz).

Part 7.

A solution of the thiol prepared in Part 6 above (0.50 g, 2.40 mmol), N-[2,4-bis(methylthio)-6-methylpyridin-3-yl]-1-chloroacetamide (0.55 g, 2.00 mmol), and potassium carbonate (0.36 g, 2.58 mmol) in tetrahydrofuran (10 mL) and dimethylformamide (0.3 mL) was heated to 50° C. for 24 hours. The mixture was cooled, poured into water (100 mL), and extracted with methylene chloride (2×100 mL). The extracts were combined, dried over anhydrous sodium sulfate, filtered and evaporated. The residual material was separated by flash chromatography (3:7 ethyl acetate-hexane) to afford the title product, which was purified by recrystallization from ether-methylene chloride (152 mg, 0.34 mmol, 14%).

m.p., 116°–118°

$^1$H NMR (300 MHz): δ8.08 (1H, br s); 7.35–7.17 (5H, m); 6.66 (1H, s); 3.35 (1H, d, J=16.8 Hz); 3.27 (1H, d, J=16.8 Hz); 3.09 (1H, dd, J=12.5, 7.0 Hz); 3.02 (1H, dd, J=12.5, 8.0 Hz); 2.91–2.80 (1H, m); 2.51 (3H, s); 2.50 (3H, s); 2.39 (3H, s); 1.86–1.75 (1H, m); 1.73–1.60 (1H, m); 1.28–1.14 (6H, m); 0.83 (3H, t, J=6 Hz).

$^{13}$C NMR (300 MHz, CDCl$_3$): δ167.6, 157.0, 156.6, 148.5, 43.6, 128.5, 127.7, 126.7, 123.4, 113.8, 45.7, 40.4, 36.7, 35.8, 31.8, 27.1, 24.4, 22.5, 14.0, 13.9, 12.9.

IR (KBr): 3248, 2928, 1662, 1564, 1536, 1502, 1438, 808, 700 cm⁻.

Mass spectrum (NH₃-Cl/DDIP): m/z 451 (17%); 450 (29%); 449 (100%); 227 (1%).

Elemental analysis: calculated C 61.57, H 7.19, N 6.24; observed C 61.32, H 7.07, N 6.16.

EXAMPLE 1038

N-[2,4-bis(methylthio)-6-methylpyridin-3-yl]-2-[(6,6-dimethylbicyclo[3.1.1]hepten-2-yl)methyl]thioacetamide Method 1

Part 1.

The method of Wang, C.-S., *J. Het. Chem.*, v. 7, p. 389 (1970) was used to convert 4-hydroxy-6-methyl-2-pyrone (45.5 g, 361 mmol) into 4-hydroxy-6-methyl-2-pyridone (38.3 g, 306 mmol, 85%), then 4-hydroxy-6-methyl-2-pyridone (55.6 g, 447 mmol) into 4-hydroxy-6-methyl-3-nitro-2-pyridone (36.3 g, 213 mmol, 48%). The method of Albert, et al., *J. Chem. Soc.*, p. 3832 (1954) was used to convert 4-hydroxy-6-methyl-3-nitro-2-pyridone (36.3 g, 213 mmol) into 2,4-dichloro-6-methyl-3-nitropyridine (21.2 g, 102 mmol, 48%). This material was dissolved in methanol (150 mL), cooled to 0° C., and treated with sodium thiomethoxide (15.0 g, 214 mmol). After being allowed to stir for 1 2 hours, the reaction mixture was filtered, and the pre cipitate was washed with ether. The solid product, 2,4-bis(methylthio)-6-methyl-3-nitropyridine (23.3 g, 101 mmol, 99%), had a melting point of 179°–180° C.

¹H NMR (300 MHz): δ6.79 (1H, s); 2.56 (3H, s); 2.53 (3H, s); 2.47 (3H, s).

Mass spectrum (NH₃-Cl/DDIP): m/z 233 (10%); 232 (12%); 231 (100%).

Part 2.

A solution of the nitropyridine compound from Part 1 above (11.0 g, 47.8 mmol) and hydrochloric acid (conc., 21 mL) in acetic acid (480 mL) was cooled to 0° C., and treated in small portions with zinc powder (36.7 g, 561 mmol). After being allowed to stir for 2 hours, the mixture was filtered and neutralized with sodium bicarbonate. This was extracted twice with methylene chloride, and the extracts were combined, dried over anhydrous sodium sulfate, filtered and evaporated. The residue was separated by flash chromatogaphy (1:9 ethyl acetate-hexane) to afford the product, 3-amino-2,4-bis(methylthio)-6-methylpyridine, as a solid.

¹H NMR (300 MHz): δ6.73 (1H, s); 4.03 (2H, s); 2.60 (3H, s); 2.45 (3H, s); 2.43 (3H, s).

Mass spectrum (NH₃-Cl/DDIP): m/z 203 (9%); 202 (12%); 201 (100%); 189 (1%).

An alternate procedure may be used to prepare 2,4-bis(methylthio)-6-methyl-3-nitropyridine. The nitro compound (24.0 g, 30.3 mmol) was suspended in 242 mL of 1:1 water-dioxane, and stirred at ambient temperature while ammonium hydroxide (conc. aqueous, 53 mL) was added. The solution was stirred vigorously for 15 minutes, and sodium hydrosulfite (47.0 g, 270 mmol) was added in portions over 30 minutes. The solution, which warmed and formed a milky white suspension, was stirred for 1 hour, then filtered (with washing with ethyl acetate) and evaporated. The residual liquid was extracted with ethyl acetate (3×), and the extracts were combined, dried over anhydrous magnesium sulfate, filtered and evaporated to afford the product (9.43 g, 45%).

Part 3.

A solution of 3-amino-2,4-bis(methylthio)-6-methylpyridine (0.38 g, 1.88 mmol) and triethylamine (0.30 mL, 2.07 mmol) in tetrahydrofuran (8 mL) was cooled to 0° C. and treated with a solution of chloroacetyl chloride (0.18 mL, 2.26 mmol) in tetrahydrofuran (4 mL). After being stirred for 10 hours, the mixture was poured into water (100 mL), and this was extracted with ethyl acetate (2×100 mL). The extracts were combined, dried over anhydrous sodium sulfate, filtered and evaporated. The resulting solid was recrystallized to purity from ether, mp 190°–192° C., to afford N-[2,4-bis(methylthio)-6-methyl-pyridin-3-yl]-2-chloroacetamide (0.39 g, 1.41 mmol, 75%).

¹H NMR (300 MHz): δ7.69 (1H, br s); 6.68 (1H, s); 4.26 (2H, s); 2.53 (3H, s); 2.51 (3H, s); 2.43 (3H, s).

Mass spectrum (NH₃-Cl/DDIP): m/z 279 (42%); 278 (17%); 277 (100%); 227 (4%).

Part 4.

Potassium carbonate (19.4 g, 140 mmol) was suspended in tetrahydrofuran (500 mL), and thiolacetic acid (10.0 mL, 140 mmol) was added dropwise. Then, a solution of 2-chloroacetophenone (16.6 g, 108 mmol) in tetrahydrofuran (100 mL) was added dropwise, and the mixture was allowed to stir for 10 hours. It was poured into water (700 mL), and the resulting mixture was extracted with ethyl acetate (700 mL), then methylene chloride (700 mL). The extracts were combined, dried over anhydrous magnesium sulfate, filtered and evaporated. The residual oil was purified by filtration through a short plug of silica gel (1:1 ethyl acetate-hexane) to afford phenacylthioacetate (20.0 g, 103 mmol, 96%) as an oil.

¹H NMR (300 MHz): δ7.99 (2H, d, J=8.4 Hz); 7.60 (1H, t, J=7.7 Hz); 7.48 (2H, t, J=8.1 Hz); 4.41 (2H, s); 2.41 (3H, s).

Mass spectrum (NH₃-Cl/DDIP): m/z 212 (100%); 197 (2%); 196 (4%); 195 (19%); 153 (1%).

Part 5.

A solution of the thioacetate from Part 4 above (8.70 g, 44.8 mmol) in ether (50 mL) was stirred vigorously while aqueous sodium hydroxide solution (50 mL, 2N, 100 mmol) was added. This mixture was stirred for 2 hours, then separated. The aqueous layer was cooled to 0° C. and acidified to pH 5 with 1N hydrochloric acid. This was extracted with methylene chloride (2×100 mL), and the extracts were combined, dried over anhydrous magnesium sulfate, filtered and evaporated. The residual liquid was distilled (110°–120° C., 1 mm Hg, bulb-to-bulb) to afford the pure product, 2-mercaptoacetophenone (6.00 g, 39.4 mmol, 88%).

¹H NMR (300 MHz): δ7.97 (2H, dd, J=8.2, 1.2 Hz); 7.63–7.57 (1H, m); 7.52–7.45 (2H, m); 3.97 (2H, d, J=7.3 Hz); 2.14 (1H, t, J=7.3 Hz).

Mass spectrum (NH₃-Cl/DDIP): m/z 172 (5%); 171 (10%); 170 (100%); 153 (20%); 138 (15%).

Part 6.

A solution of the chloride compound from Part 3 above (0.49 g, 1.77 mmol), 2-mercaptoacetophenone (0.49 g, 3.22 mmol), and potassium carbonate (0.27 g, 1.95 mmol) in tetrahydrofuran (20 mL) was heated to 50° C. for 6 hours. The mixture was then cooled, and poured into water (100 mL). This was extracted with methylene chloride (2×100 mL). The extracts were combined, dried over anhydrous sodium sulfate, filtered and evaporated. The resulting solid was recrystallized from ether (mp 140°–142° C.) to afford pure N-[2,4-bis(methylthio)-6-methylpyridin-3-yl]-2-phenacylthioacetamide (0.433 g, 1.10 mmol, 62%).

¹H NMR (300 MHz): δ8.11 (1H, br s); 8.02–7.96 (2H, m); 7.65–7.45 (3H, m); 6.66 (1H, s); 4.31 (2H, s); 3.46 (2H, s); 2.49 (3H, s); 2.48 (3H, s); 2.39 (3H, s).

Mass spectrum (NH$_3$-CI/DDIP): m/z 395 (17%); 394 (25%); 393 (100%); 285 (1%); 275 (5%).

Part 7.

A solution of the sulfide from Part 6 above (0.50 g, 1.27 mmol) and b-pinene (2.10 mL, 12.7 mmol) in 30 mL 4:1 benzene-dimethylformamide in a 100 mL roundbottom flask was suspended in 3% aqueous copper sulfate solution in a pyrex dish, fitted with a tapwater cooling line. The bath was suspended above a 270 W sun lamp. The apparatus was irradiated for 7 hours while the bath temperature was maintained below 30° C. using the water line. After this time, the contents of the reaction flask were evaporated, and the oily residue was separated by flash chromatography (1:4 ethyl acetate-hexane) to afford the title product (27 mg, 66 mmol, 5%).

Method 2

Part 1.

A solution of phosphorus tribromide (2.00 mL, 21.1 mmol) and pyridine (0.65 mL, 8.03 mmol) in benzene (20 mL) was cooled to 0° C., and a solution of (1R)-(−)-myrtenol (10.0 mL, 62.7 mmol) in benzene (10 mL) was added dropwise. The mixture was allowed to stir for 14 hours, then poured over ice (150 g) and allowed to warm to ambient temperature. The resulting mixture was extracted with ethyl acetate (2×200 mL), and the extracts were combined, dried over anhydrous magnesium sulfate, filtered and evaporated. The resulting oil was sufficiently pure product, 2-(bromomethyl)-6,6-dimethylbicyclo[3.1.1]heptene (13.5 g, 62.7 mmol, 100%).

$^1$H NMR (300 MHz): δ5.68 (1H, br s); 3.96 (1H, d, J=9.9 Hz); 3.94 (1H, d, J=9.9 Hz); 2.44 (1H, dr, J=8.8, 5.5 Hz); 2.34–2.20 (3H, m); 2.12–2.04 (1H, m); 1.31 (3H, s); 1.17 (1H, d, J=8.8 Hz); 0.83 (3H, s).

Mass spectrum (NH$_3$-CI/DDIP): m/z 217 (16%); 216 (2%); 215 (19%); 135 (100%).

Part 2.

A suspension of the bromide compound from Part 1 above (7.47 g, 34.7 mmol), thiolacetic acid (2.80 mL, 39.2 mmol), potassium carbonate (5.96 g, 43.1 mmol) and tetra-n-butylammonium iodide (2.50 g, 6.77 mmol) in tetrahydrofuran (50 mL) was heated to reflux for 12 hours, then cooled and poured into water (200 mL). This was extracted with methylene chloride (2×200 mL), and the extracts were combined, dried over anhydrous magnesium sulfate, filtered and evaporated. The oily residue was separated by flash chromatography (1:19 ethyl acetate-hexane) to afford the product, 6,6-dimethyl-2-(thioacetylmethyl)-bicyclo[3.1.1]-heptene, as an oil (4.91 g, 23.3 mmol, 67%).

$^1$H NMR (300 MHz): δ5.48 (1H, dd, J=3.0, 1.4 Hz); 3.54 (1H, d, J=13.5 Hz); 3.50 (1H, d, J=13.5 Hz); 2.37 (1H, dt, J=8.8, 5.7 Hz); 2.32 (3H, s); 2.26–2.00 (4H, m); 1.27 (3H, s); 1.14 (1H, d, J=8.8 Hz); 0.80 (3H, s).

Mass spectrum (NH$_3$-CI/DDIP): m/z 211 (17%); 167 (40%); 155 (37%); 135 (100%).

Part 3.

A solution of the thioacetate from Part 2 above (1.17 g, 5.56 mmol) in methanol (20 mL) was treated with potassium carbonate (1.54 g, 11.1 mmol), and stirred at ambient temperature for 6 hours. The mixture was evaporated, and the residue was taken up in tetrahydrofuran (20 mL). The mixture was treated with the chloride from Method A, Part 3 above (1.40 g, 5.06 mmol), and heated to reflux for 14 hours. After being cooled, the reaction mixture was poured into 200 mL water, and extracted with methylene chloride (2×200 mL). The extracts were combined, dried over anhydrous sodium sulfate, filtered and evaporated. The residual material was separated by flash chromatography (3:7 ethyl acetate-hexane) to afford the title product as a solid (0.77 g, 1.88 mmol, 37%).

m.p., 66°–68°

$^1$H NMR (300 MHz): δ8.26 (1H, br s); 6.66 (1H, s); 5.51 (1H, br s); 3.38 (1H, d, J=13.2 Hz); 3.35 (2H, s); 3.25 (1H, dd, J=13.2, 1.1 Hz); 2.52 (3H, s); 2.50 (3H, s); 2.42 (3H, s); 2.35–2.06 (6H, m); 1.30 (3H, s); 0.86 (3H, s).

$^{13}$C NMR (300 MHz, CDCl$_3$): δ167.6, 157.0, 156.6, 148.6, 142.0, 123.4, 122.2, 113.8, 45.3, 40.6, 39.1, 38.2, 34.7, 31.8, 31.4, 26.2, 24.5, 21.2, 14.0, 12.9.

Mass spectrum (NH$_3$-CI/DDIP): m/z 411 (18%); 410 (24%); 409 (100%); 359 (1%); 287 (2%).

Elemental analysis: calculated C 58.79, H 6.91, N 6.86; observed C 58.77, H 6.85, N 6.74.

EXAMPLES 1031 AND 1032

N-[2,4-bis(methylthio)-6-methylpyridin-3-yl]-2-(E- and Z-2-pentyloct-2-enyl)thioacetamide Part 1.

A mixture of ethyl 2-bromoheptanoate (20.0 mL, 100 mmol) and triethylphosphite (20.0 mL, 114 mmol) was heated to 120°. Over the course of six hours, ethyl bromide begins to evolve, and is collected by a distillation head. The resulting liquid is sufficiently pure triethyl 2-phosphonoheptanoate (27.1 g, 92.2 mmol, 92%).

Part 2.

A slurry of sodium hydride (0.95 g, 39.6 mmol) in tetrahydrofuran (40 mL) was cooled to 0°, and a solution of the phosphonate compound from Part 1 (11.6 g, 39.4 mmol) in tetrahydrofuran (20 mL) was added dropwise with stirring. The ice bath was removed, and after 1 hour at ambient temperature, the mixture was treated with hexanal (5.00 mL, 41.6 mmol), and the resulting mixture was allowed to stir overnight. It was poured into water (250 mL), and this was extracted with ethyl acetate (2×250 mL). The extracts were combined, dried over anhydrous magnesium sulfate, filtered and evaporated. The residual oil was separated by flash chromatography (2:98 ethyl acetate-hexane) to afford, first, ethyl Z-2-pentyloct-2-enoate (4.13 g, 17.1 mmol, 43%), then ethyl E-2-pentyloct-2-enoate (4.20 g, 17.5 mmol, 44%), both clear, colorless oils.

For the Z isomer:

$^1$H NMR (300 MHz): δ5.82 (1H, t, J=7.3 Hz); 4.20 (2H, q, J=7.1 Hz); 2.38 (2H, q, J=7.3 Hz); 2.23 (2H, t, J=7.3 Hz); 1.48–1.30 (12H, m); 1.30 (3H, t, J=7.1 Hz); 0.89 (3H, t, J=6 Hz); 0.88 (3H, t, J=7 Hz).

Mass spectrum (NH$_3$-CI/DDIP): m/z 258 (4%); 242 (25%); 241 (100%).

For the E isomer:

$^1$H NMR (300 MHz): δ6.73 (1H, t, J=7.5 Hz); 4.18 (2H, q, J=7.3 Hz); 2.28 (2H, t, J=7.3 Hz); 2.16 (2H, t, J=7.3 Hz); 1.51–1.25 (12H, m); 1.29 (3H, t, J=7.3 Hz); 0.90 (3H, t, J=6.6 Hz); 0.89 (3H, t, J=6.6 Hz).

Mass spectrum (NH$_3$-CI/DDIP): m/z 258 (8%); 242 (15%); 241 (100%); 195 (1%).

Part 3.

The Z isomer from Part 2 above (3.04 g, 12.6 mmol) was dissolved in dichloromethane (20 mL), and the solution was cooled to 0°. A solution of diisobutylaluminum hydride in dichloromethane (26.0 mL, 1.0M, 26.0 mmol) was added by syringe dropwise, and the resulting mixture was stirred overnight. It was recooled to 0°, and quenched by the slow addition of 5 mL water. The mixture was diluted to 150 mL dichloromethane, and washed with an equal volume of 0.5N hydrochloric acid. The organic phase was dried over anhydrous magnesium sulfate, filtered and evaporated to afford sufficiently pure product, Z-2-pentyloct-2-en-1-ol, as a clear, colorless oil (2.43 g, 12.3 mmol, 97%).

$^1$H NMR (300 MHz): δ5.31 (1H, t, J=7.3 Hz); 4.13 (2H, d, J=5.5 Hz); 2.15–2.02 (4H, m); 1.49–1.20 (12H, m); 1.08 (1H, t, J=5.5 Hz); 0.89 (3H, t, J=6.6 Hz); 0.88 (3H, t, J=6.2 Hz).

Mass spectrum (CH$_4$-Cl/DDIP): m/z 199 (27%); 198 (32%); 111 (100%).

The E isomer (3.13 g, 13.0 mmol) was treated in a similar manner to afford E-2-pentyloct-2-en-1-ol (2.47 g, 12.4 mmol, 96%).

$^1$H NMR (300 MHz): δ5.40 (1H, t, J=7.1 Hz); 4.03 (2H, d, J=5.1 Hz); 2.13–1.99 (4H, m); 1.42–1.22 (13H, m); 0.89 (6H, t, J=6.6 Hz).

Mass spectrum (CH$_4$-Cl/DDIP): m/z 199 (55%); 197 (100%); 179 (47%).

Part 4.

The Z alcohol from Part 3 above (2.43 g, 12.3 mmol) in benzene (10 mL) was added dropwise to an ice-cooled solution of phosphorus tribromide (0.50 mL, 5.27 mmol) and pyridine (0.30 mL, 3.71 mmol) in benzene (20 mL). The mixture was stirred for 48 hours, then poured over ice (120 g). The mixture was allowed to melt, and extracted with ethyl acetate (2×150 mL). The extracts were combined, dried over anhydrous potassium carbonate, filtered and evaporated. The resulting oil was sufficiently pure Z-1-bromo-2-pentyl-2-octene (3.14 g, 12.0 mmol, 98%).

$^1$H NMR (300 MHz): δ5.40 (1H, t, J=7.3 Hz); 4.01 (2H, s); 2.20–1.90 (4H, m); 1.50–1.20 (12H, m); 0.89 (6H, t, J=6.8 Hz).

The E alcohol from Part 3 above (2.47 g, 12.4 mmol) was treated in a similar manner to afford E-1-bromo-2-pentyl-2-octene (3.27 g, 12.5 mmol, 100%).

$^1$H NMR (300 MHz): δ5.60 (1H, t, J=7.3 Hz); 4.01 (2H, s); 2.23–2.00 (4H, m); 1.46–1.23 (12H, m); 0.90 (3H, t, J=6.6 Hz); 0.89 (3H, t, J=6.6 Hz).

Part 5.

A solution of the Z bromide from Part 4 above (3.14 g, 12.0 mmol), ethyl mercaptoacetate (1.30 mL, 11.9 mmol), and potassium carbonate (1.97 g, 14.2 mmol) in tetrahydrofuran (25 mL) was heated to reflux for 12 hours. The mixture was cooled, and poured into water (100 mL). This was extracted with ethyl acetate (2×120 mL), and the extracts were washed in sequence with brine, combined, dried over anhydrous magnesium sulfate, filtered and evaporated. The residue was separated by flash chromatography (2:98 ethyl acetate-hexane) to afford the product, ethyl 2-(Z-2-pentyl-2-octenyl)thioacetate, as an oil (2.82 g, 9.38 mmol, 79%).

$^1$H NMR (300 MHz): δ5.36 (1H, t, J=7.3 Hz); 4.18 (2H, q, J=7.0 Hz); 3.31 (2H, s); 3.13 (2H, s); 2.16–2.00 (4H, m); 1.45–1.22 (15H, m); 0.89 (6H, t, J=6.6 Hz).

Mass spectrum (NH$_3$-Cl/DDIp): m/z 318 (89%); 302 (16%); 301 (82%); 181 (100%).

The E bromide from Part 4 above (3.27 g, 12.5 mmol) was treated in a similar manner to afford ethyl 2-(E-2-pentyl-2-octenyl)thioacetate as an oil (2.61 g, 8.69 mmol, 73%).

$^1$H NMR (300 MHz): δ5.30 (1H, t, J=7.3 Hz); 4.18 (2H, q, J=7.3 Hz); 3.21 (2H, s); 3.10 (2H, s); 2.17–2.00 (4H, m); 1.42–1.22 (15H, m); 0.89 (6H, t, J=6.6 Hz).

Mass spectrum (NH$_3$-Cl/DDIP): m/z 318 (97%); 302 (15%); 301 (93%); 181 (100%).

Part 6.

The Z sulfide ester from Part 5 above (1.40 g, 4.66 mmol) was stirred in ethanolic sodium hydroxide solution (37.5 mL of 0.25N, 9.38 mmol) for 10 hours. The solution was evaporated, and the residue was acidified to pH 5 with 1N hydrochloric acid. This mixture was diluted to 100 mL with water, then extracted with ethyl acetate (2×100 mL). The extracts were washed in sequence with brine, combined, dried over anhydrous magnesium sulfate, filtered and evaporated. The residue was taken up in dichloromethane (15 mL), 1 drop of dimethylformamide was added, and the resulting solution was treated with a solution of oxalyl chloride (14.0 mmol) in dichloromethane (7 mL). The solution was stirred for 2 hours, then evaporated. The oily residue was taken up in tetrahydrofuran (10 mL), and the solution was slowly added to an ice-cooled solution of 3-amino-2,4-bis(methylthio)-6-methylpyridine (800 mg, 3.99 mmol) and potassium carbonate (0.69 g, 4.99 mmol) in tetrahydrofuran (20 mL). After stirring for 12 hours, the mixture was poured into 100 mL water, and extracted with ethyl acetate (2×100 mL). The extracts were washed in sequence with brine, combined, dried over anhydrous sodium sulfate, filtered and evaporated. The residue was separated by flash chromatography (1:4 ethyl acetate-hexane), and the Z isomer of the title product was recrystallized to purity from ether-hexane (m.p., 100°–101°) (first crop 820 mg, 1.80 mmol, 45%).

$^1$H NMR (300 MHz): δ8.32 (1H, br s); 6.67 (1H, s); 5.41 (1H, t, J=7.3 Hz); 3.44 (2H, s); 3.34 (2H, s); 2.52 (3H, s); 2.50 (3H, s); 2.42 (3H, s); 2.20–2.03 (4H, m); 1.50–1.20 (12H, m); 0.87 (3H, t, J=6.3 Hz); 0.86 (3H, t, J=6.9 Hz).

$^{13}$C NMR (300 MHz, CDCl$_3$): δ167.8, 157.0, 156.6, 148.6, 133.3, 130.8, 123.4, 113.8, 35.7, 35.6, 32.9, 31.5, 29.7, 28.1, 28.0, 27.9, 24.5, 22.6, 22.5, 14.1 (2C), 14.0, 12.9.

IR (KBr): 3232, 2956, 2924, 1662, 1566, 1538, 1506, 808 cm$^{-1}$.

Mass spectrum (NH$_3$-Cl/DDIP): m/z 457 (17%); 456 (28%); 455 (100%).

Elemental analysis: calculated C 60.75, H 8.42, N 6.16; observed C 60.77, H 8.35, N 6.18.

The E isomer was prepared in a similar manner in 78% yield as a solid.

m.p., 76°–77°

$^1$H NMR (300 MHz): δ8.21 (1H, br s); 6.67 (1H, s); 5.41 (1H, t, J=7.3 Hz); 3.36 (2H, s); 3.32 (2H, s); 2.52 (3H, s); 2.50 (3H, s); 2.42 (3H, s); 2.20–2.00 (4H, m); 1.47–1.22 (12H, m); 0.90 (3H, t, J=6 Hz); 0.88 (3H, t, J=6Hz).

$^{13}$C NMR (300 MHz, CDCl$_3$): δ167.7, 156.9, 156.5, 148.6, 33.2, 131.6, 123.4, 113.7, 39.7, 34.3, 31.9, 31.6, 29.5, 28.4, 28.1, 28.0, 24.4, 22.6, 22.5, 14.1 (2C), 14.0, 12.9.

IR (KBr): 3256, 2956, 2926, 2856, 1676, 1564, 1532, 1480, 1436, 1340, 808 cm$^{-1}$.

Mass spectrum (NH$_3$-Cl/DDIP): m/z 457 (17%); 456 (28%); 455 (100%); 227 (3%).

Elemental analysis: calculated C 60.75, H 8.42, N 6.16; observed C 61.06, H 8.41, N 5.77.

c)$^1$H NMR (300 MHz): δ8.63 (1H, br s); 7.40 (2H, d, J=8.0 Hz); 7.21 (1H, t, J=8.0 Hz); 5.47 (1H, br s); 3.38 (2H, s); 3.32 (1H, d, J=13.2 Hz); 3.20 (1H, dd, J=13.2, 1.1 Hz); 2.47–2.09 (5H, m); 1.31 (3H, s); 1.16 (1H, d, J=8.8 Hz); 0.86 (3H, s). $^{13}$C NMR (300 MHz, CDCl$_3$): δ167.1, 141.9, 133.7, 132.1, 128.7, 128.5, 122.1, 45.3, 40.5, 39.0, 38.2, 34.7, 31.8, 31.4, 26.2, 21.2. Mass spectrum (NH$_3$-Cl/DDIP): m/z 372 (68%); 371 (22%); 370 (100%); 253 (9%); 135 (66%). Elemental analysis: calculated C 58.38, H 5.72, N 3.78; observed C 58.66, H 5.73, N 3.61.

For preparation of the compounds of Formula I wherein R$^3$ is CF$_2$R$^8$, the method shown in Scheme 12 may be conveniently employed. α-Keto esters (43) may be prepared by treating ethyl or methyl oxalate with an aryl or alkylmagnesium bromide, which may be prepared by reacting an aryl or alkylbromide (42) with magnesium, in ethyl ether or tetrahydrofuran. The α-keto ester (43) may then be treated with diethylaminosufur trifluoride (DAST) at a temperature ranging from 20° to 60° according to the procedure described in W. J. Middleton and E. M. Bingham; J. Org. Chem. 1980, 45,2883–2887. Treatment of the resulting a,α-difluoroaryl or α-,α-difluoroalkyl acetate (44) with a base such as potassium hydroxide, sodium hydroxide or lithium hydroxide in ethanol-water or methanol-water at a temperature ranging from 20° to reflux temperature gives the corresponding acid. The α,α-difluoro carboxylic acid of formula (45) may be converted to the acid chloride of formula (46) by treatment with oxalyl chloride or thionyl chloride as described earlier.

Scheme 12

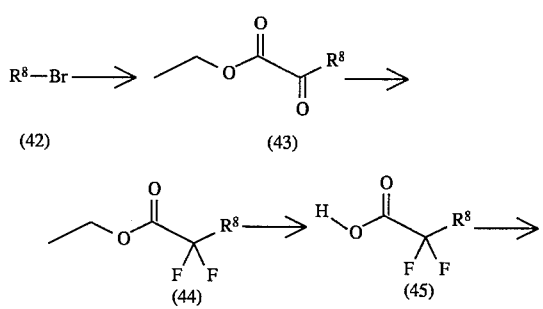

Alternatively, α,α-difluoroaryl or α,α-difluoroalkyl acetate (44) may also be synthesized by reacting iododifluoroacetates with an alkene and zinc in the presence of catalytic amount of nickel dichloride hexahydrate as described in Z.-Y. Yang and D. J. Burton; J. Chem. Soc. Chem. Commun, 223–224, 1992 and references therein (Scheme 13).

Scheme 13

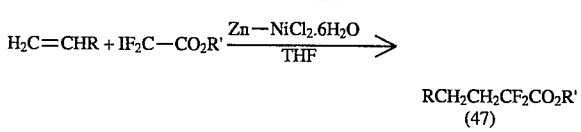

RCH$_2$CH$_2$CF$_2$CO$_2$R'
(47)

The amides of formula (48) and imides of formula (49) may be prepared by treatment of a primary amine R$^1$—NH$_2$ with an acid chloride of formula (46). This reaction typically carried out in anhydrous methylene chloride or 1,2-dichoroethane as a solvent in the presence of a base such as triethylamine, pyridine or dimethylaminopyridine as an acid scavenger.

Scheme 14

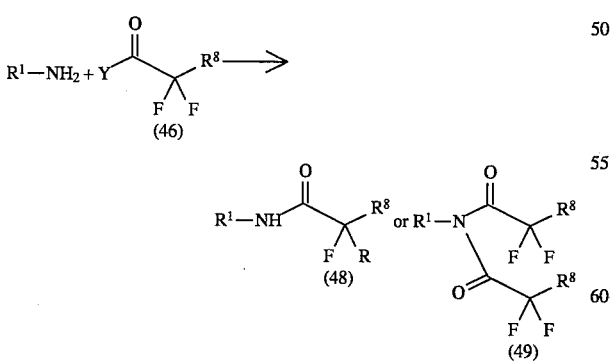

For preparation of the compounds of Formula I wherein R$^3$ is C(O)R$^8$, the method shown in Scheme 15 may be conveniently employed. An α-keto esters (43), which may be prepared as described in Scheme 12, may be treated with a base such as potassium hydroxide, lithium hydroxide or sodium hydroxide in a polar solvent such as water, methanol or a mixture of water and methanol, or with a strong acid such as sulfuric acid, hydrochloric acid in water or a mixture of water and dioxane at a temperature ranging from 20° to reflux temperature of the solvent to give α-keto acids of formula (50). The α-keto acids (50) may be converted to α-keto acid halides of formula (51) and then to α-keto amides of Formula I wherein R$^3$ is C(O) R$^8$ as described in the Method B of the amide formation. Typically α-keto acid halides (51) are prepared by treating α-keto acids (50) with oxalyl chloride or thionyl chloride in an inert solvent such as methylene chloride, dichloroethane or diethyl ether at a temperature ranging from 20° to reflux temperature. Amides of Formula I are typically prepared by treatment of an amine, R$^1$R$^2$—NH with the acid chloride of formula (51) in the presence of a base such as triethylamine, pyridine or dimethylaminopyridine as an acid scavenger.

Scheme 15

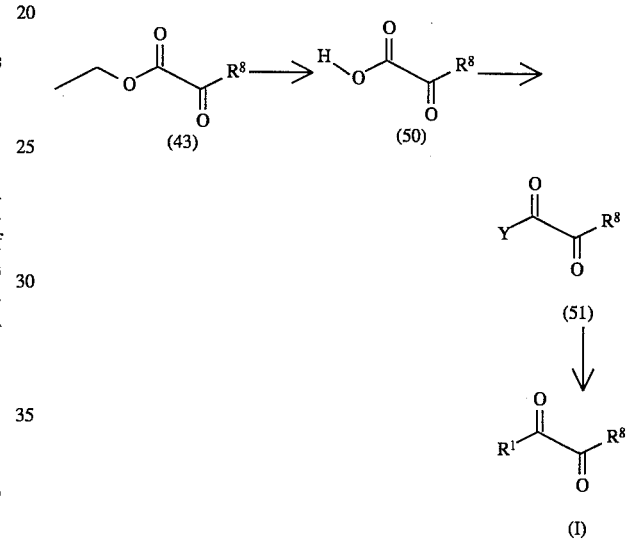

Alternatively, the compounds of Formula I wherein R$^3$ is C(O)R$^8$, may be prepared by treatment of amine R$^1$—NH$_2$ with methyl oxalyl chloride to give methyl oxamates of formula (52) which can be treated with a Grignard reagent R$^8$MgX or a lithium reagent R$^8$Li to provide the amides of Formula I (Scheme 16).

Scheme 16

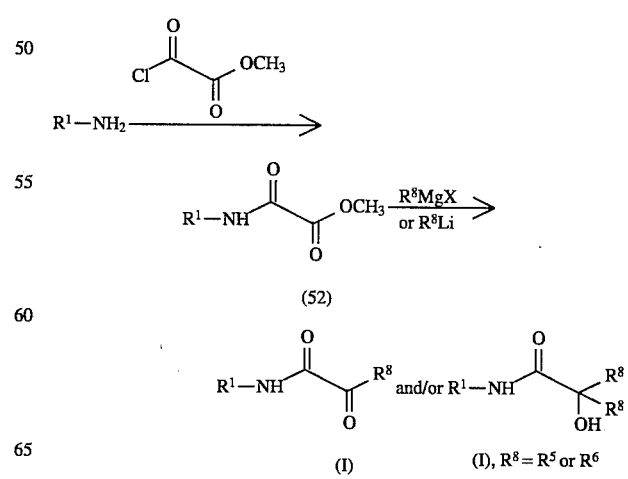

EXAMPLE 2001

N-[2,4-bis(methylthio)-6-methyl-3-pyridyl]-a,a-difluoro-(4-isobutyl)phenylacetamide Part 1.

To a stirred solution of a,α-difluoro-4-isobutyl-phenylacetic acid (500 mg, 2.2 mmol) in methylene chloride (10 ml) was added oxalyl chloride (300 mg, 2.4 mmol) followed by catalytic amount of dimethyl formamide. The mixture was stirred at room temperature for 2 hours and then was evaporated in vacuo to remove all the volitiles. The resulting residue was used without purification for the subsequent step.

Part 2.

To a stirred solution of 3-amino-2,4-bis(methylthio)-6-methyl-pyridine (140 mg, 0.7 mmol) and N,N-dimethyl-4-amino-pyridine (10 mg, 0.1 mmol) in dichloroethane (5 ml) was added a,α-difluoro-4-isobutyl-phenylacetyl chloride (160 mg, 0.6 mmol) and the mixture was stirred at room temperature for 48 hours. At the end of the stirring the mixture was diluted with ethyl acetate and washed with 1N NaOH solution. The organic layer was washed with water, dried ($Na_2SO_4$) and evaporated to give an oily residue. Purification by column chromatography on silica gel with elution by 3:1 mixture of hexane and ethyl acetate to give the titled compound as an oil. The oil was dissolved in methylene chloride and triturated with hexane to give white solid (0.11 g, 45%).

m.p., 134.9°–135.4°

$^1$H-NMR (300 MHz): δ7.66–7.63 (d, 2H, J=8 Hz, $H_{AR}$), 7.48 (s, 1H, NH), 7.26–7.29 (d, 2H, J=6 Hz, $H_{Ar}$), 6.65 (s, 1H, $H_{pyr}$), 2.54–2.51 (d, 2H, $CH_2$), 2.49 (s, 6H, 2$CH_3$), 2.39 (s, 3H, $CH_3$), 1.93–1.84 (m, 1H, CH), 0,91–0.89 (d, 6H, J=6 Hz, 2$CH_3$).

$^{19}$F-NMR ($CDCl_3$/F11): δ–101.99 (s, 2F, $CF_2$)

Mass spectrum ($NH_3$-CI/DDIP): m/e 411 (M+H)$^+$.

EXAMPLE 2005

N-[2,4-bis(methylthio)-6-methyl-3-pyridyl]-2-cyclohexyl-2,2-difluoro-acetamide

Preparation of 2-(4-isobutylcyclohexyl)-2,2-difluoro ethanoic acid

Part 1.

a,α-difluoro-4-isobutyl-phenylacetic acid (900 mg, 3.9 mmol) and platinum oxide (50 mg) were suspended in acetic acid (10 ml). The mixture was hydrogenated at 50 psi for 24 hours. The mixture was filtered over celite, washed with methylene chloride, concentrated in vacuo to give 2-cyclohexyl-2,2-difluoro-acetic acid as an oil (800 mg, 88%).

Mass spectrum ($NH_3$-CI/DDIP): m/e 235 (M+H)$^+$.

Parts 2 and 3.

According to similar procedures to that described in parts 1 and 2 of Example 2001, 2-cyclohexyl-2,2-difluoro-acetic acid was converted to the titled compound.

m.p., 173.3°–173.8°

Mass spectrum ($NH_3$-CI/DDIP): m/e 417.2 (M+H)$^+$.

EXAMPLE 2029

N-[2,4-bis(methylthio)-6-methyl-3-pyridyl]-α,α-difluoro-4-chloro-phenylacetamide Part 1.

To a solution of diethyloxylate (2.94 g, 20.1 mmol) in 3 ml of anhydrous tetrahydrofuran was added 4-chlorophenylmagnesium bromide (30 ml of 0.33M solution in diethyl ether (10 ml) and tetrahydrofuran (20 ml)) dropwise over one hour period at –10°. After stirring at –10° for another 30 minutes, 40 ml of 5% HCl was added to quench the reaction. The organic layer was then separated, washed with sat.$NH_4Cl$, sat.$NaHCO_3$ and brine, dried over anhydrous $Na_2SO_4$ and evaporated the solvent in vacuo to give a crude product (2.63 g). 600 mg of this crude product was then mixed with 0.5 ml of DAST (3.8 mmol). The mixture was warmed to 40° and then cooled to room temperature. After stirring at room temperature for two hours, the reaction mixture was poured on ice and extracted with ethyl acetate. The organic layer was washed with water, dried over anhydrous $Na_2SO_4$ and removed the solvent in vacuo to give crude product which was purified by flash column chromatography to give 261 mg of pure ethyl 4-chlorophenyl-2,2-difluoroacetate.

Part 2.

Ethyl 4-chlorophenyl-2,2-difluoroacetate (250 mg) and potassium hydroxide (300 mg) were mixed in 27 ml of ethanol and 2.4 ml of water and the reaction mixture was refluxed for four hours. The mixture was then acidified and extracted with ethyl acetate. The organic layer was washed with water, dried over anhydrous $Na_2SO_4$ and the solvent was removed in vacuo to give a product which was dissolved in 410 mg of oxalyl chloride with catalytic amount of N,N-dimethylformamide. The mixture was stirred for two hours and excess oxalyl chloride was removed in vacuo to give 4-chlorophenyl-2,2-difluoroethanoyl chloride which was used as is for the subsequent step.

Part 3.

4-Chlorophenyl-2,2-difluoroethanoyl chloride obtained from previous step was added to a solution of 2,4-bis(methylthio)-3-amino-6-methylpyridine (221 mg, 1.1 mmol) and catalytic amount of N,N-dimethyl-4-aminopyridine in 5 ml of anhydrous methylene chloride and stirred at room temperature overnight. After quenching the reaction with water, the mixture was extracted with ethyl acetate, washed with brine, dried over anhydrous $Na_2SO_4$ and removed the solvent to give the titled compound (50 mg).

m.p., 162°–164°

Mass spectrum ($NH_3$-CI/DDIP): m/e 289 (M+H)$^+$.

EXAMPLE 2032

N-[2,4-bis(methylthio)-6-methyl-3-pyridyl]-α,α-difluoro-4-biphenylacetamide

Part 1.

4-Biphenyl-2,2-difluoroacetic acid (402 mg. 1.73 mmol) was dissolved in 3 ml of thionyl chloride and refluxed for two hours. Excess thionyl chloride was removed in vacuo to give 2,2-difluoro-4-biphenylacetyl chloride (392 mg) which was used as is for the subsequent step.

Part 2.

4-Biphenyl-2,2-difluoroethanoyl chloride (300 mg, 1.16 mmol) obtained from previous step was added to a solution of 2,4-bis(methylthio)-3-amino-6-methylpyridine (148 mg, 1.1 mmol) in anhydrous 1,2-dichloroethane (8 ml) and triethylamine (0.1 ml), and the mixture was stirred at room temperature for four hours. After quenching the reaction with 2 ml of methanol, the solvent was removed by evaporation to give the crude product which was purified by flash column chromatography to give the titled compound (267 mg).

m.p., 173°–174°

Mass spectrum ($NH_3$-CI/DDIP): m/e 431 $(M+H)^+$.

EXAMPLE 2033

N-[2,4-bis(methylthio)-6-methyl-3-pyridyl]-α,α-difluoro-4-trifluoromethyl-phenylacetamide Part 1.

4-Chlorophenyl-2,2-difluoroacetic acid (400 mg) was dissolved in thionyl chloride (3 ml) and the solution was refluxed for two hours. Excess thionyl chloride was removed in vacuo to give 4-trifluoromethylphenyl-2,2-difluoroethanoyl chloride (406 mg) as an oil, which was used as is for the subsequent step.

Part 2.

4-Trifluoromethylphenyl-2,2-difluoroethanoyl chloride (300 mg, 1.16 mmol) obtained from previous step was added to a solution of 3-amino-2,4-bis(methylthio)-6-methylpyridine (146 mg, 1.1 mmol) in anhydrous 1,2-dichloroethane (8 ml) and triethylamine (0.1 ml) and the mixture was stirred at room temperature for four hours. After quenching the reaction with 2 ml of methanol, the solvent was removed by evaporation to give the crude product which was purified by flash column chromatography to give 101.9 mg of the titled compound and 166 mg of N-[α,α-difluoro-4-(trifluoromethyl) phenylacetyl]-N-[2,4-bis(methylthio)-6-methyl-3-pyridyl]-α,α-difluoro-4-(trifluoromethyl) phenylacetoimide [Mass spectrum ($NH_3$-CI/DDIP): m/e 645 $(M+H)^+$].

Data of Example 2033 m.p., 179°–180.5°

Mass spectrum ($NH_3$-CI/DDIP): m/e 423 $(M+H)^+$.

EXAMPLE 2138

N-[2,4-bis(methylthio)-6-methyl-3-pyridyl]-4-biphenylglyoxylamide

Part 1.

To a solution of 3-amino-2,4-bis(methylthio)-6-methylpyridine (1.0 g, 5.0 mmol) in anhydrous 1,2-dichoroethane (10 ml) and triethylamine (5.2 ml) was added methyl oxalyl chloride (1.225 g, 10 mmol) and the mixture was stirred at room temperature for 30 minutes. After quenching the reaction with methanol, the solvent was removed by evaporation. Then the residue was purified by flash column chromatography to give N-[2,4-bis(methylthio)-6-methyl-3-pyridyl]methyl oxamate as a solid (1.26 g) m.p., 153°–155°.

Part 2.

To a solution of N-[2,4-bis(methylthio)-6-methyl-3-pyridyl]methyl oxamate (300 mg, 1.05 mmol) in anhydrous tetrahydronfuran (20 ml) was added 10 ml of biphenyl mangesium bromide (made from 470 mg of biphenyl bromide and 50 mg of mangenesium) dropwise at –3°. After quenching the reaction with methanol and water, the mixture was extracted with ethyl acetate, washed with brine, dried over anhydrous $Na_2SO_4$ and removed the solvent to give the titled product (80 mg).

m.p., 219°–221°

Mass spectrum ($NH_3$-CI/DDIP): m/e 409.0 $(M+H)^+$.

EXAMPLE 2139

N-[2,4-bis(methylthio)-6-methyl-3-pyridyl]-phenylglyoxylamide

To a solution of N-[2,4-bis(methylthio)-6-methyl-3-pyridyl]methyl oxamate (201 mg, 0.7 mmol) in anhydrous tetrahydronfuran (8 ml) was added 1.1 ml of phenyllithium (1.8M solution in cyclohexane) dropwise at –78° C. After quenching the reaction with methanol and water, the mixture was extracted with ethyl acetate, washed with brine, dried over anhydrous $Na_2SO_4$ and removed the solvent to give an oily residue. The residue was purified by flash column chromatography on silica gel to give 14 mg of the titled compound and N-[2,4-bis(methylthio)-6-methyl-3-pyridyl]-diphenylglycolyiamide [Mass spectrum ($NH_3$-CI/DDIP): m/e 411.0 $(M+H)^+$].

Data of Example 2139 m.p., 229°–231°

Mass spectrum ($NH_3$-CI/DDIP): m/e 333.0 $(M+H)^+$.

Utility

The compounds of this invention possess antiatherosclerotic and antihypercholesteolemic efficacy, as evidenced by their activity in the ACAT assays, as described below.

The compounds of the invention are effective antiatherosclerotic agents that act in a variety of ways. The compounds may be inhibitors of the enzyme acyl CoA:cholesterol acyl transferase (ACAT). Inhibition of ACAT has a variety of antiatherosclerotic effects, including inhibiting esterification and transport of cholesterol across the intestinal wall. In addition, by inhibiting cholesterol ester formation, the compounds may be useful in preventing the formation of cholesterol ester rich macrophages (foam cells) in the arterial wall. Foam cells are a source of the large quantity of cholesterol ester found in atheromatous lesions, as compared to the surrounding undiseased tissue. Other compounds of the invention may be inhibitors of cholesterol biosynthesis in the liver. Some compounds of the invention are both ACAT inhibitors and inhibitors of cholesterol biosynthesis.

A. Assay of the Inhibition of Acyl-CoA: Cholesterol Acyltransferase (ACAT) in Hepatic Microsomes (In Vitro Assay)

The ability of the compounds to inhibit ACAT, the enzyme responsible for the intracellular synthesis of cholesteryl esters, was tested as follows. Male Sprague Dawley rats weighing 150–300 g, were fed rat chow ad libitum. The animals were fasted for twenty-four hours prior to being euthanized by $CO_2$. The livers were perfused in situ with 50 ml of cold 0.25 sucrose, excised, and homogenized in three volumes of 0.1M phosphate buffer, pH 7.4, that contained 0.5 mM EDTA (ethylenediamine-tetraacetic acid), 1.0 mM glutathione, 0.25M sucrose and 20 mM leupeptin. Microsomes were obtained by differential centrifugation; the supernatant from an initial spin at 15,000×g for 15 minutes was centrifuged at 105,000×g for 1 hour to pellet the microsomes. The microsomes were suspended in homogenization buffer, reisolated by centrifugation, and stored at –70° C. Microsomes were used within one month of preparation.

The control assay in a final volume of 200 μl consisted of 200 μg of microsomal protein, 75 μM $^{14}$C-oleoyl-CoA (10,000 dpm/nmol) in 0.1M phosphate, pH 7.4, that contained 1 mM glutathione. Compounds were added in 5 μl of DMSO (dimethyl sulfoxide) and additional controls were run with DMSO only. All components, except the oleoyl-CoA, were preincubated for 15 min. at 37° C. prior to the initiation of the reaction by the addition of oleoyl-CoA. The assay was terminated after 10 min by the addition of 4 ml of chloroform:methanol (2:1, v/v). 20,000 dpm of $^3$H-cholesteryl oleate and 10 μg of unlabeled cholesteryl oleate and oleic acid were added as an internal standard and carriers, respectively. After allowing 10 min. for lipid extraction, the samples were centrifuged at 1,000×g for 10 min to separate the solvent layers. The chloroform layer containing the neutral lipids was spotted onto a Baker SI250-Pa silica gel TLC plate and the plate developed using a hexane:diethyl ether:acetic acid (170:30:1) v/v/v) mobile phase. The lipids were visualized by their interaction with iodine vapor and the cholesteryl ester spot was scraped into a scintillation vial and counted. The specific activity of ACAT in the control incubation averaged 260 pmol/min/mg microsomal protein. The data obtained are expressed as the concentration at which ACAT activity is inhibited by 50% ($IC_{50}$).

B. Assay for the Systemic Availability of ACAT Inhibitors (Ex Vivo Assay)

The inhibition of ACAT activity in livers obtained from rats orally dosed with an inhibitor was used as a determination of the compound's systemic availability. The ability of ACAT inhibitors to affect cholesterol esterification in livers obtained from dosed animals was tested as follows. This assay is also referred to herein as the Ex Vivo Assay. Male (CD) Sprague Dawley rats weighing from 190–210 g were fed purina lab chow ad libitum. Rats, three per group, were orally gavaged with 10 mg/kg of active ACAT inhibitor. The compounds were dissolved in ethanol (10% of final volume); a PEG solution (80 propylene glycol:20 polyethylene glycol 400, w:w) was added and the compound was mixed completely prior to dosing. A control group received the dosing vehicle alone. The animals were dosed once on Day 1 (am), twice on Day 2 (am and pm) and once on the morning of Day 3. Three hours after the last dose animals were euthanized using $CO_2$. Livers were perfused with a 0.25M sucrose solution, excised, and frozen. Livers were thawed and resuspended in buffer (2 mL/g, 0.1M Phosphate, pH 7.4, 1.0 mM glutathione, 0.5 mM EDTA, 20 μM leupeptin, 60 μM benzamidine, and 0.25M sucrose). The samples were homogenized and post nuclear microsomes were obtained by centrifugation: 1.000×g for 5 min. and the resulting supernatant, 100,000×g for 1 hr. Microsomes were resuspended in phosphate buffer to approximately 25 mg/mL and frozen at −70° C. until assayed for ACAT activity.

ACAT assays contained in a final volume of 200 μl:100 ug microsomal protein, 75 μM $^{14}$C-oleoyl-CoA (10,000 dpm/nmol), 0.75 mg bovine serum albumin, 0.1M phosphate buffer, pH 7.4, and 1 mM glutathione. All components, except the oleoyl-CoA, were preincubated for 15 min at 37° C. prior to the initiation of the reaction by the addition of oleoyl-CoA. The assay was terminated after 10 min and ACAT activity determined as described in section A above. The average specific activity of ACAT in the vehicle control group was 661±64 pmol/min/mg (SEM). The data (% inhibition) are expressed as 100 minus the % ACAT activity in livers from dosed animals versus those from a vehicle control group.

Table A below sets forth the ACAT inhibitory activity of representative compounds of the present invention.

TABLE A

| Example Number | ACAT Inhibitory Activity (In Vitro) ($IC_{50}$) |
|---|---|
| 41 | +++ |
| 42 | +++ |
| 46 | +++ |
| 47 | +++ |
| 48 | +++ |
| 49 | +++ |
| 50 | +++ |
| 63 | +++ |
| 64 | ++ |
| 85 | +++ |
| 89 | +++ |
| 90 | +++ |
| 91 | +++ |
| 92 | +++ |
| 102 | +++ |
| 103 | +++ |
| 104 | +++ |
| 118 | +++ |
| 122 | +++ |
| 123 | +++ |
| 124 | +++ |
| 125 | +++ |
| 135 | +++ |
| 136 | +++ |
| 137 | +++ |
| 146 | ++ |
| 147 | ++ |
| 148 | +++ |
| 152 | +++ |
| 153 | +++ |
| 154 | +++ |
| 165 | +++ |
| 166 | +++ |
| 167 | +++ |
| 176 | +++ |
| 180 | +++ |
| 181 | +++ |
| 182 | +++ |
| 204 | +++ |
| 210 | +++ |
| 232 | +++ |
| 236 | +++ |
| 237 | +++ |
| 260 | +++ |
| 264 | +++ |
| 165 | +++ |
| 288 | +++ |
| 292 | +++ |
| 295 | +++ |
| 316 | +++ |
| 317 | +++ |
| 321 | +++ |
| 322 | +++ |
| 325 | +++ |
| 326 | +++ |
| 347 | |
| 375 | +++ |
| 379 | +++ |
| 380 | +++ |
| 381 | +++ |
| 393 | +++ |
| 394 | +++ |
| 403 | +++ |
| 407 | |
| 410 | +++ |
| 411 | +++ |
| 431 | +++ |
| 435 | +++ |
| 437 | +++ |
| 439 | +++ |
| 459 | |
| 463 | +++ |

TABLE A-continued

| Example Number | ACAT Inhibitory Activity (In Vitro) (IC$_{50}$) |
|---|---|
| 464 | +++ |
| 465 | +++ |
| 467 | +++ |
| 484 | +++ |
| 487 | +++ |
| 515 | +++ |
| 522 | |
| 543 | |
| 600 | |
| 607 | |
| 617 | |

In Table A, ACAT inhibition activity in the In Vitro Assay is represented as follows: +++=<1 µM; ++=1–10 µM; +=11–50 µM.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences*, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiatherosclerotic and antihypercholesteolemic agent.

The compounds of this invention can be administered by any means that produces contact of the active agent with the agent's site of action, ACAT, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonire, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | Wt. % |
|---|---|
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | Wt. % |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | Wt. % |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | Wt. % |
|---|---|
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | Wt. % |
|---|---|
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | Wt. % |
| --- | --- |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of atherosclerosis or hypercholesteolemia, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

The term "consisting essentially of" where used in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited references may provide further useful information, however, these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

The Tables below set forth representative compounds of the invention.

TABLE 1

$$R^1-NH-C(=O)-CR^5(H)-X-R^7$$

| Ex. No. | R¹* | X | R⁵ | R⁷ | m.p. |
|---|---|---|---|---|---|
| 1 | A | O | Ph | n-$C_6H_{13}$ | amorphous |
| 2 | A | O | Ph | n-$C_6H_{13}$ | 58–59.5 |
| 3 | A | O | Ph | n-$C_3H_7$ | |
| 4 | A | O | Ph | n-$C_4H_9$ | |
| 5 | A | O | Ph | n-$C_5H_{11}$ | |
| 6 | A | O | Ph | i-$C_5H_{11}$ | |
| 7 | A | O | Ph | i-$C_6H_{13}$ | |
| 8 | A | O | Ph | n-$C_7H_{15}$ | |
| 9 | A | O | Ph | i-$C_7H_{15}$ | |
| 10 | A | O | Ph | n-$C_8H_{17}$ | |
| 11 | A | O | Ph | i-$C_8H_{17}$ | |
| 12 | A | O | Ph | n-$C_{10}H_{21}$ | |
| 13 | A | O | Ph | i-$C_{10}H_{21}$ | |
| 14 | A | O | Ph | $CH_2$Ph | 125–126 |
| 15 | A | O | Ph | $CH_2$(4-Cl)Ph | |
| 16 | A | O | Ph | $CH_2$(4-F)Ph | |
| 17 | A | O | Ph | $CH_2$(4-$OCH_3$)Ph | |
| 18 | A | O | Ph | $CH_2$(4-$OC_4H_9$)Ph | |
| 19 | A | O | Ph | Ph | |
| 20 | A | O | Ph | (4-Cl)Ph | |
| 21 | A | O | Ph | (4-F)Ph | |
| 22 | A | O | Ph | (4-$OCH_3$)Ph | |
| 23 | A | O | Ph | (4-$OC_4H_9$)Ph | |
| 24 | A | O | Ph | (4-OPh)Ph | |
| 25 | A | O | Ph | (4-$C_4H_9$)Ph | |
| 26 | A | O | Ph | (4-Ph)Ph | |
| 27 | A | O | Ph | (3-Cl)Ph | |
| 28 | A | O | Ph | (3-$OC_4H_9$)Ph | |
| 29 | A | O | Ph | (3-OPh)Ph | |
| 30 | A | O | Ph | (2-Cl)Ph | |
| 31 | A | O | Ph | (2-$OC_4H_9$)Ph | |
| 32 | A | O | Ph | (2-OPh)Ph | |
| 33 | A | O | Ph | (2-pyridyl)$CH_2$ | |
| 34 | A | O | Ph | (3-pyridyl)$CH_2$ | |
| 35 | A | O | Ph | (4-pyridyl)$CH_2$ | |
| 36 | A | O | Ph | (2-furfuryl)$CH_2$ | |
| 37 | A | O | Ph | (3-furfuryl)$CH_2$ | |
| 38 | A | O | Ph | (2-thienyl)$CH_2$ | |
| 39 | A | O | Ph | (3-thienyl)$CH_2$ | |
| 40 | A | S | Ph | n-$C_6H_{13}$ | 132–133 |
| 41 | A | S | Ph | n-$C_6H_{13}$ | amorphous |
| 42 | B | S | Ph | n-$C_6H_{13}$ | 141–142 |
| 43 | A | S | Ph | n-$C_4H_9$ | |
| 44 | A | S | Ph | n-$C_8H_{17}$ | |
| 45 | A | S | Ph | n-$C_{10}H_{21}$ | |
| 46 | A | S | Ph | $CH_2$Ph | 156–158 |
| 47 | A | S | Ph | $CH_2$Ph | amorphous |
| 48 | B | S | Ph | $CH_2$Ph | 182.5–183.5 |
| 49 | A | S | Ph | $C_2H_5$ | 149–151 |
| 50 | A | S | Ph | $C_2H_5$ | 150–152 |
| 51 | A | S | Ph | $CH_2$(4-Cl)Ph | |
| 52 | A | S | Ph | $CH_2$(4-F)Ph | |
| 53 | A | S | Ph | $CH_2$(4-$OCH_3$)Ph | |

TABLE 1-continued $$R^1-NH-C(=O)-CR^5(H)-X-R^7$$

| Ex. No. | R¹* | X | R⁵ | R⁷ | m.p. |
|---|---|---|---|---|---|
| 54 | A | S | Ph | $CH_2$(4-$OC_4H_9$)Ph | |
| 55 | A | S | Ph | $CH_2$(3-Cl)Ph | |
| 56 | A | S | Ph | $CH_2$(3-F)Ph | |
| 57 | A | S | Ph | $CH_2$(3-$OCH_3$)Ph | |
| 58 | A | S | Ph | $CH_2$(3-$OC_4H_9$)Ph | |
| 59 | A | S | Ph | $CH_2$(2-Cl)Ph | |
| 60 | A | S | Ph | $CH_2$(2-F)Ph | |
| 61 | A | S | Ph | $CH_2$(2-$OCH_3$)Ph | |
| 62 | A | S | Ph | $CH_2$(2-$OC_4H_9$)Ph | |
| 63 | A | S | Ph | Ph | 156–158 |
| 64 | B | S | Ph | Ph | 199–200 |
| 65 | A | S | Ph | (4-Cl)Ph | |
| 66 | A | S | Ph | (4-F)Ph | |
| 67 | A | S | Ph | (4-$OCH_3$)Ph | |
| 68 | A | S | Ph | (4-$OC_4H_9$)Ph | |
| 69 | A | S | Ph | (4-OPh)Ph | |
| 70 | A | S | Ph | (4-$C_4H_9$)Ph | |
| 71 | A | S | Ph | (4-Ph)Ph | |
| 72 | A | S | Ph | (3-Cl)Ph | |
| 73 | A | S | Ph | (3-$OC_4H_9$)Ph | |
| 74 | A | S | Ph | (3-OPh)Ph | |
| 75 | A | S | Ph | (2-Cl)Ph | |
| 76 | A | S | Ph | (2-$OC_4H_9$)Ph | |
| 77 | A | S | Ph | (2-OPh)Ph | |
| 78 | A | S | Ph | (2-pyridyl)$CH_2$ | |
| 79 | A | S | Ph | (3-pyridyl)$CH_2$ | |
| 80 | A | S | Ph | (4-pyridyl)$CH_2$ | |
| 81 | A | S | Ph | (2-furfuryl)$CH_2$ | |
| 82 | A | S | Ph | (3-furfuryl)$CH_2$ | |
| 83 | A | S | Ph | (2-thienyl)$CH_2$ | |
| 84 | A | S | Ph | (3-thienyl)$CH_2$ | |
| 85 | A | S | (4-Cl)Ph | n-$C_6H_{13}$ | 164.5–165.5 |
| 86 | A | S | (4-Cl)Ph | n-$C_4H_9$ | |
| 87 | A | S | (4-Cl)Ph | n-$C_8H_{17}$ | |
| 88 | A | S | (4-Cl)Ph | n-$C_{10}H_{21}$ | |
| 89 | A | S | (4-Cl)Ph | $CH_2$Ph | 200.5–202.0 |
| 90 | A | S | (4-Cl)Ph | $CH_2$(4-$OCH_3$)Ph | 194.5 |
| 91 | A | S | (4-Cl)Ph | $CH_2$(4-F)Ph | 198.4 |
| 92 | A | S | (4-Cl)Ph | $CH_2$(4-Cl)Ph | 185–187 |
| 93 | A | S | (4-Cl)Ph | $CH_2$(4-$OC_4H_9$)Ph | |
| 94 | A | S | (4-Cl)Ph | $CH_2$(3-Cl)Ph | |
| 95 | A | S | (4-Cl)Ph | $CH_2$(3-F)Ph | |
| 96 | A | S | (4-Cl)Ph | $CH_2$(3-$OCH_3$)Ph | |
| 97 | A | S | (4-Cl)Ph | $CH_2$(3-$OC_4H_9$)Ph | |
| 98 | A | S | (4-Cl)Ph | $CH_2$(2-Cl)Ph | |
| 99 | A | S | (4-Cl)Ph | $CH_2$(2-F)Ph | |
| 100 | A | S | (4-Cl)Ph | $CH_2$(2-$OCH_3$)Ph | |
| 101 | A | S | (4-Cl)Ph | $CH_2$(2-$OC_4H_9$)Ph | |
| 102 | A | S | (4-Cl)Ph | Ph | 176–177 |
| 103 | A | S | (4-Cl)Ph | (4-$OCH_3$)Ph | 163–165 |
| 104 | A | S | (4-Cl)Ph | (4-F)Ph | 193.5–195 |
| 105 | A | S | (4-Cl)Ph | (4-$OC_4H_9$)Ph | |
| 106 | A | S | (4-Cl)Ph | (4-OPh)Ph | |
| 107 | A | S | (4-Cl)Ph | (4-$C_4H_9$)Ph | |
| 108 | A | S | (4-Cl)Ph | (4-Ph)Ph | |
| 109 | A | S | (4-Cl)Ph | (3-Cl)Ph | |
| 110 | A | S | (4-Cl)Ph | (3-$OC_4H_9$)Ph | |
| 111 | A | S | (4-Cl)Ph | (3-OPh)Ph | |
| 112 | A | S | (4-Cl)Ph | (2-Cl)Ph | |
| 113 | A | S | (4-Cl)Ph | (2-$OC_4H_9$)Ph | |
| 114 | A | S | (4-Cl)Ph | (2-OPh)Ph | |
| 115 | A | S | (4-Cl)Ph | (3-pyridyl)$CH_2$ | |
| 116 | A | S | (4-Cl)Ph | (2-furfuryl)$CH_2$ | |
| 117 | A | S | (4-Cl)Ph | (2-thienyl)$CH_2$ | |
| 118 | A | S | (4-$OCH_3$)Ph | n-$C_6H_{13}$ | 129.5–130.5 |

TABLE 1-continued $$\begin{array}{c} R^1 \diagdown_N \diagdown \diagup^O \diagdown R^5 \\ H \quad X \diagdown R^7 \end{array}$$

| Ex. No. | R¹ * | X | R⁵ | R⁷ | m.p. |
|---|---|---|---|---|---|
| 119 | A | S | (4-OCH₃)Ph | n-C₄H₉ | |
| 120 | A | S | (4-OCH₃)Ph | n-C₈H₁₇ | |
| 121 | A | S | (4-OCH₃)Ph | n-C₁₀H₂₁ | |
| 122 | A | S | (4-OCH₃)Ph | CH₂Ph | 173–175 |
| 123 | A | S | (4-OCH₃)Ph | CH₂(4-Cl)Ph | 178–180 |
| 124 | A | S | (4-OCH₃)Ph | CH₂(4-F)Ph | 176–177 |
| 125 | A | S | (4-OCH₃)Ph | CH₂(4-OCH₃)Ph | 168–169.5 |
| 126 | A | S | (4-OCH₃)Ph | CH₂(4-OC₄H₉)Ph | |
| 127 | A | S | (4-OCH₃)Ph | CH₂(3-Cl)Ph | |
| 128 | A | S | (4-OCH₃)Ph | CH₂(3-F)Ph | |
| 129 | A | S | (4-OCH₃)Ph | CH₂(3-OCH₃)Ph | |
| 130 | A | S | (4-OCH₃)Ph | CH₂(3-OC₄H₉)Ph | |
| 131 | A | S | (4-OCH₃)Ph | CH₂(2-Cl)Ph | |
| 132 | A | S | (4-OCH₃)Ph | CH₂(2-F)Ph | |
| 133 | A | S | (4-OCH₃)Ph | CH₂(2-OCH₃)Ph | |
| 134 | A | S | (4-OCH₃)Ph | CH₂(2-OC₄H₉)Ph | |
| 135 | A | S | (4-OCH₃)Ph | Ph | 165–166.5 |
| 136 | A | S | (4-OCH₃)Ph | (4-F)Ph | 182.3 |
| 137 | A | S | (4-OCH₃)Ph | (4-OCH₃)Ph | 154.4 |
| 138 | A | S | (4-OCH₃)Ph | (4-Cl)Ph | |
| 139 | A | S | (4-OCH₃)Ph | (4-OC₄H₉)Ph | |
| 140 | A | S | (4-OCH₃)Ph | (4-OPh)Ph | |
| 141 | A | S | (4-OCH₃)Ph | (4-C₄H₉)Ph | |
| 142 | A | S | (4-OCH₃)Ph | (4-Ph)Ph | |
| 143 | A | S | (4-OCH₃)Ph | (3-pyridyl)CH₂ | |
| 144 | A | S | (4-OCH₃)Ph | (2-furfuryl)CH₂ | |
| 145 | A | S | (4-OCH₃)Ph | (2-thienyl)CH₂ | |
| 146 | A | O | (4-OCH₃)Ph | CH₃ | 130–131 |
| 147 | B | O | (4-OCH₃)Ph | CH₃ | 165–165.5 |
| 148 | A | S | (4-F)Ph | n-C₆H₁₃ | 149–150 |
| 149 | A | S | (4-F)Ph | n-C₄H₉ | |
| 150 | A | S | (4-F)Ph | n-C₈H₁₇ | |
| 151 | A | S | (4-F)Ph | n-C₁₀H₂₁ | |
| 152 | A | S | (4-F)Ph | CH₂Ph | 188.5–190 |
| 153 | A | S | (4-F)Ph | CH₂(4-F)Ph | 186–188 |
| 154 | A | S | (4-F)Ph | CH₂(4-OCH₃)Ph | 182–183 |
| 155 | A | S | (4-F)Ph | CH₂(4-Cl)Ph | |
| 156 | A | S | (4-F)Ph | CH₂(4-OC₄H₉)Ph | |
| 157 | A | S | (4-F)Ph | CH₂(3-Cl)Ph | |
| 158 | A | S | (4-F)Ph | CH₂(3-F)Ph | |
| 159 | A | S | (4-F)Ph | CH₂(3-OCH₃)Ph | |
| 160 | A | S | (4-F)Ph | CH₂(3-OC₄H₉)Ph | |
| 161 | A | S | (4-F)Ph | CH₂(2-Cl)Ph | |
| 162 | A | S | (4-F)Ph | CH₂(2-F)Ph | |
| 163 | A | S | (4-F)Ph | CH₂(2-OCH₃)Ph | |
| 164 | A | S | (4-F)Ph | CH₂(2-OC₄H₉)Ph | |
| 165 | A | S | (4-F)Ph | Ph | 156–158 |
| 166 | A | S | (4-F)Ph | (4-F)Ph | 172.5–174 |
| 167 | A | S | (4-F)Ph | (4-OCH₃)Ph | 171.5–173 |
| 168 | A | S | (4-F)Ph | (4-Cl)Ph | |
| 169 | A | S | (4-F)Ph | (4-OC₄H₉)Ph | |
| 170 | A | S | (4-F)Ph | (4-OPh)Ph | |
| 171 | A | S | (4-F)Ph | (4-C₄H₉)Ph | |
| 172 | A | S | (4-F)Ph | (4-Ph)Ph | |
| 173 | A | S | (4-F)Ph | (3-pyridyl)CH₂ | |
| 174 | A | S | (4-F)Ph | (2-furfuryl)CH₂ | |
| 175 | A | S | (4-F)Ph | (2-thienyl)CH₂ | |
| 176 | A | S | (3,4-Cl₂)Ph | n-C₆H₁₃ | amorphous |
| 177 | A | S | (3,4-Cl₂)Ph | n-C₄H₉ | |
| 178 | A | S | (3,4-Cl₂)Ph | n-C₈H₁₇ | |
| 179 | A | S | (3,4-Cl₂)Ph | n-C₁₀H₂₁ | |
| 180 | A | S | (3,4-Cl₂)Ph | CH₂Ph | amorphous |
| 181 | A | S | (3,4-Cl₂)Ph | CH₂(4-F)Ph | amorphous |
| 182 | A | S | (3,4-Cl₂)Ph | CH₂(4-OCH₃)Ph | amorphous |
| 183 | A | S | (3,4-Cl₂)Ph | CH₂(4-Cl)Ph | |
| 184 | A | S | (3,4-Cl₂)Ph | CH₂(4-OC₄H₉)Ph | |
| 185 | A | S | (3,4-Cl₂)Ph | CH₂(3-Cl)Ph | |
| 186 | A | S | (3,4-Cl₂)Ph | CH₂(3-F)Ph | |
| 187 | A | S | (3,4-Cl₂)Ph | CH₂(3-OCH₃)Ph | |
| 188 | A | S | (3,4-Cl₂)Ph | CH₂(3-OC₄H₉)Ph | |
| 189 | A | S | (3,4-Cl₂)Ph | CH₂(2-Cl)Ph | |
| 190 | A | S | (3,4-Cl₂)Ph | CH₂(2-F)Ph | |
| 191 | A | S | (3,4-Cl₂)Ph | CH₂(2-OCH₃)Ph | |
| 192 | A | S | (3,4-Cl₂)Ph | CH₂(2-OC₄H₉)Ph | |
| 193 | A | S | (3,4-Cl₂)Ph | Ph | |
| 194 | A | S | (3,4-Cl₂)Ph | (4-F)Ph | |
| 195 | A | S | (3,4-Cl₂)Ph | (4-OCH₃)Ph | |
| 196 | A | S | (3,4-Cl₂)Ph | (4-Cl)Ph | |
| 197 | A | S | (3,4-Cl₂)Ph | (4-OC₄H₉)Ph | |
| 198 | A | S | (3,4-Cl₂)Ph | (4-OPh)Ph | |
| 199 | A | S | (3,4-Cl₂)Ph | (4-C₄H₉)Ph | |
| 200 | A | S | (3,4-Cl₂)Ph | (4-Ph)Ph | |
| 201 | A | S | (3,4-Cl₂)Ph | (3-pyridyl)CH₂ | |
| 202 | A | S | (3,4-Cl₂)Ph | (2-furfuryl)CH₂ | |
| 203 | A | S | (3,4-Cl₂)Ph | (2-thienyl)CH₂ | |
| 204 | A | S | (2,4-F₂)Ph | n-C₆H₁₃ | 138–139 |
| 205 | A | S | (2,4-F₂)Ph | n-C₄H₉ | |
| 206 | A | S | (2,4-F₂)Ph | n-C₈H₁₇ | |
| 207 | A | S | (2,4-F₂)Ph | n-C₁₀H₂₁ | |
| 208 | A | S | (2,4-F₂)Ph | CH₂Ph | |
| 209 | A | S | (2,4-F₂)Ph | CH₂(4-F)Ph | |
| 210 | A | S | (2,4-F₂)Ph | CH₂(4-OCH₃)Ph | 147.5–148 |
| 211 | A | S | (2,4-F₂)Ph | CH₂(4-Cl)Ph | |
| 212 | A | S | (2,4-F₂)Ph | CH₂(4-OC₄H₉)Ph | |
| 213 | A | S | (2,4-F₂)Ph | CH₂(3-Cl)Ph | |
| 214 | A | S | (2,4-F₂)Ph | CH₂(3-F)Ph | |
| 215 | A | S | (2,4-F₂)Ph | CH₂(3-OCH₃)Ph | |
| 216 | A | S | (2,4-F₂)Ph | CH₂(3-OC₄H₉)Ph | |
| 217 | A | S | (2,4-F₂)Ph | CH₂(2-Cl)Ph | |
| 218 | A | S | (2,4-F₂)Ph | CH₂(2-F)Ph | |
| 219 | A | S | (2,4-F₂)Ph | CH₂(2-OCH₃)Ph | |
| 220 | A | S | (2,4-F₂)Ph | CH₂(2-OC₄H₉)Ph | |
| 221 | A | S | (2,4-F₂)Ph | Ph | |
| 222 | A | S | (2,4-F₂)Ph | (4-F)Ph | |
| 223 | A | S | (2,4-F₂)Ph | (4-OCH₃)Ph | |
| 224 | A | S | (2,4-F₂)Ph | (4-Cl)Ph | |
| 225 | A | S | (2,4-F₂)Ph | (4-OC₄H₉)Ph | |
| 226 | A | S | (2,4-F₂)Ph | (4-OPh)Ph | |
| 227 | A | S | (2,4-F₂)Ph | (4-C₄H₉)Ph | |
| 228 | A | S | (2,4-F₂)Ph | (4-Ph)Ph | |
| 229 | A | S | (2,4-F₂)Ph | (3-pyridyl)CH₂ | |
| 230 | A | S | (2,4-F₂)Ph | (2-furfuryl)CH₂ | |
| 231 | A | S | (2,4-F₂)Ph | (2-thienyl)CH₂ | |
| 232 | A | S | [3,4-(OCH₃)₂]Ph | n-C₆H₁₃ | amorphous |
| 233 | A | S | [3,4-(OCH₃)₂]Ph | n-C₄H₉ | |
| 234 | A | S | [3,4-(OCH₃)₂]Ph | n-C₈H₁₇ | |
| 235 | A | S | [3,4-(OCH₃)₂]Ph | n-C₁₀H₂₁ | |
| 236 | A | S | [3,4-(OCH₃)₂]Ph | CH₂Ph | amorphous |
| 237 | A | S | [3,4-(OCH₃)₂]Ph | CH₂(4-F)Ph | amorphous |
| 238 | A | S | [3,4-(OCH₃)₂]Ph | CH₂(4-OCH₃)Ph | |
| 239 | A | S | [3,4-(OCH₃)₂]Ph | CH₂(4-Cl)Ph | |
| 240 | A | S | [3,4-(OCH₃)₂]Ph | CH₂(4-OC₄H₉)Ph | |
| 241 | A | S | [3,4-(OCH₃)₂]Ph | CH₂(3-Cl)Ph | |
| 242 | A | S | [3,4-(OCH₃)₂]Ph | CH₂(3-F)Ph | |
| 243 | A | S | [3,4-(OCH₃)₂]Ph | CH₂(3-OCH₃)Ph | |
| 244 | A | S | [3,4-(OCH₃)₂]Ph | CH₂(3-OC₄H₉)Ph | |
| 245 | A | S | [3,4-(OCH₃)₂]Ph | CH₂(2-Cl)Ph | |
| 246 | A | S | [3,4-(OCH₃)₂]Ph | CH₂(2-F)Ph | |
| 247 | A | S | [3,4-(OCH₃)₂]Ph | CH₂(2-OCH₃)Ph | |
| 248 | A | S | [3,4-(OCH₃)₂]Ph | CH₂(2-OC₄H₉)Ph | |
| 249 | A | S | [3,4-(OCH₃)₂]Ph | Ph | |

TABLE 1-continued $$\begin{array}{c} R^1 \\ | \\ H \end{array} \begin{array}{c} O \\ \| \\ N \end{array} \begin{array}{c} R^5 \\ | \\ X \\ | \\ R^7 \end{array}$$

| Ex. No. | R¹ * | X | R⁵ | R⁷ | m.p. |
|---|---|---|---|---|---|
| 250 | A | S | [3,4-(OCH₃)₂]Ph | (4-F)Ph | |
| 251 | A | S | [3,4-(OCH₃)₂]Ph | (4-OCH₃)Ph | |
| 252 | A | S | [3,4-(OCH₃)₂]Ph | (4-Cl)Ph | |
| 253 | A | S | [3,4-(OCH₃)₂]Ph | (4-OC₄H₉)Ph | |
| 254 | A | S | [3,4-(OCH₃)₂]Ph | (4-OPh)Ph | |
| 255 | A | S | [3,4-(OCH₃)₂]Ph | (4-C₄H₉)Ph | |
| 256 | A | S | [3,4-(OCH₃)₂]Ph | (4-Ph)Ph | |
| 257 | A | S | [3,4-(OCH₃)₂]Ph | (3-pyridyl)CH₂ | |
| 258 | A | S | [3,4-(OCH₃)₂]Ph | (2-furfuryl)CH₂ | |
| 259 | A | S | [3,4-(OCH₃)₂]Ph | (2-thienyl)CH₂ | |
| 260 | A | S | (4-OC₄H₉)Ph | n-C₆H₁₃ | 131.2 |
| 261 | A | S | (4-OC₄H₉)Ph | n-C₄H₉ | |
| 262 | A | S | (4-OC₄H₉)Ph | n-C₈H₁₇ | |
| 263 | A | S | (4-OC₄H₉)Ph | n-C₁₀H₂₁ | |
| 264 | A | S | (4-OC₄H₉)Ph | CH₂Ph | 154.2 |
| 265 | A | S | (4-OC₄H₉)Ph | CH₂(4-F)Ph | 161.6 |
| 266 | A | S | (4-OC₄H₉)Ph | CH₂(4-OCH₃)Ph | |
| 267 | A | S | (4-OC₄H₉)Ph | CH₂(4-Cl)Ph | |
| 268 | A | S | (4-OC₄H₉)Ph | CH₂(4-OC₄H₉)Ph | |
| 269 | A | S | (4-OC₄H₉)Ph | CH₂(3-Cl)Ph | |
| 270 | A | S | (4-OC₄H₉)Ph | CH₂(3-F)Ph | |
| 271 | A | S | (4-OC₄H₉)Ph | CH₂(3-OCH₃)Ph | |
| 272 | A | S | (4-OC₄H₉)Ph | CH₂(3-OC₄H₉)Ph | |
| 273 | A | S | (4-OC₄H₉)Ph | CH₂(2-Cl)Ph | |
| 274 | A | S | (4-OC₄H₉)Ph | CH₂(2-F)Ph | |
| 275 | A | S | (4-OC₄H₉)Ph | CH₂(2-OCH₃)Ph | |
| 276 | A | S | (4-OC₄H₉)Ph | CH₂(2-OC₄H₉)Ph | |
| 277 | A | S | (4-OC₄H₉)Ph | Ph | |
| 278 | A | S | (4-OC₄H₉)Ph | (4-F)Ph | |
| 279 | A | S | (4-OC₄H₉)Ph | (4-OCH₃)Ph | |
| 280 | A | S | (4-OC₄H₉)Ph | (4-Cl)Ph | |
| 281 | A | S | (4-OC₄H₉)Ph | (4-OC₄H₉)Ph | |
| 282 | A | S | (4-OC₄H₉)Ph | (4-OPh)Ph | |
| 283 | A | S | (4-OC₄H₉)Ph | (4-C₄H₉)Ph | |
| 284 | A | S | (4-OC₄H₉)Ph | (4-Ph)Ph | |
| 285 | A | S | (4-OC₄H₉)Ph | (3-pyridyl)CH₂ | |
| 286 | A | S | (4-OC₄H₉)Ph | (2-furfuryl)CH₂ | |
| 287 | A | S | (4-OC₄H₉)Ph | (2-thienyl)CH₂ | |
| 288 | A | S | (4-OPh)Ph | n-C₆H₁₃ | amorphous |
| 289 | A | S | (4-OPh)Ph | n-C₄H₉ | |
| 290 | A | S | (4-OPh)Ph | n-C₈H₁₇ | |
| 291 | A | S | (4-OPh)Ph | n-C₁₀H₂₁ | |
| 292 | A | S | (4-OPh)Ph | CH₂Ph | amorphous |
| 293 | A | S | (4-OPh)Ph | CH₂(4-F)Ph | |
| 294 | A | S | (4-OPh)Ph | CH₂(4-OCH₃)Ph | |
| 295 | A | S | (4-OPh)Ph | CH₂(4-Cl)Ph | amorphous |
| 296 | A | S | (4-OPh)Ph | CH₂(4-OC₄H₉)Ph | |
| 297 | A | S | (4-OPh)Ph | CH₂(3-Cl)Ph | |
| 298 | A | S | (4-OPh)Ph | CH₂(3-F)Ph | |
| 299 | A | S | (4-OPh)Ph | CH₂(3-OCH₃)Ph | |
| 300 | A | S | (4-OPh)Ph | CH₂(3-OC₄H₉)Ph | |
| 301 | A | S | (4-OPh)Ph | CH₂(2-Cl)Ph | |
| 302 | A | S | (4-OPh)Ph | CH₂(2-F)Ph | |
| 303 | A | S | (4-OPh)Ph | CH₂(2-OCH₃)Ph | |
| 304 | A | S | (4-OPh)Ph | CH₂(2-OC₄H₉)Ph | |
| 305 | A | S | (4-OPh)Ph | Ph | |
| 306 | A | S | (4-OPh)Ph | (4-F)Ph | |
| 307 | A | S | (4-OPh)Ph | (4-OCH₃)Ph | |
| 308 | A | S | (4-OPh)Ph | (4-Cl)Ph | |
| 309 | A | S | (4-OPh)Ph | (4-OC₄H₉)Ph | |
| 310 | A | S | (4-OPh)Ph | (4-OPh)Ph | |
| 311 | A | S | (4-OPh)Ph | (4-C₄H₉)Ph | |
| 312 | A | S | (4-OPh)Ph | (4-Ph)Ph | |
| 313 | A | S | (4-OPh)Ph | (3-pyridyl)CH₂ | |
| 314 | A | S | (4-OPh)Ph | (2-furfuryl)CH₂ | |
| 315 | A | S | (4-OPh)Ph | (2-thienyl)CH₂ | |
| 316 | A | S | (3-OPh)Ph | n-C₆H₁₃ | amorphous |
| 317 | A | S | [3-O(4-Br)Ph]Ph | n-C₆H₁₃ | amorphous |
| 318 | A | S | (3-OPh)Ph | n-C₄H₉ | |
| 319 | A | S | (3-OPh)Ph | n-C₈H₁₇ | |
| 320 | A | S | (3-OPh)Ph | n-C₁₀H₂₁ | |
| 321 | A | S | (3-OPh)Ph | CH₂Ph | amorphous |
| 322 | A | S | [3-O(4-Br)Ph]Ph | CH₂Ph | amorphous |
| 323 | A | S | (3-OPh)Ph | CH₂(4-F)Ph | |
| 324 | A | S | (3-OPh)Ph | CH₂(4-OCH₃)Ph | |
| 325 | A | S | (3-OPh)Ph | CH₂(4-Cl)Ph | amorphous |
| 326 | A | S | [3-O(4-Br)Ph]Ph | CH₂(4-Cl)Ph | amorphous |
| 327 | A | S | (3-OPh)Ph | CH₂(4-OC₄H₉)Ph | |
| 328 | A | S | (3-OPh)Ph | CH₂(3-Cl)Ph | |
| 329 | A | S | (3-OPh)Ph | CH₂(3-F)Ph | |
| 330 | A | S | (3-OPh)Ph | CH₂(3-OCH₃)Ph | |
| 331 | A | S | (3-OPh)Ph | CH₂(3-OC₄H₉)Ph | |
| 332 | A | S | (3-OPh)Ph | CH₂(2-Cl)Ph | |
| 333 | A | S | (3-OPh)Ph | CH₂(2-F)Ph | |
| 334 | A | S | (3-OPh)Ph | CH₂(2-OCH₃)Ph | |
| 335 | A | S | (3-OPh)Ph | CH₂(2-OC₄H₉)Ph | |
| 336 | A | S | (3-OPh)Ph | Ph | |
| 337 | A | S | (3-OPh)Ph | (4-F)Ph | |
| 338 | A | S | (3-OPh)Ph | (4-OCH₃)Ph | |
| 339 | A | S | (3-OPh)Ph | (4-Cl)Ph | |
| 340 | A | S | (3-OPh)Ph | (4-OC₄H₉)Ph | |
| 341 | A | S | (3-OPh)Ph | (4-OPh)Ph | |
| 342 | A | S | (3-OPh)Ph | (4-C₄H₉)Ph | |
| 343 | A | S | (3-OPh)Ph | (4-Ph)Ph | |
| 344 | A | S | (3-OPh)Ph | (3-pyridyl)CH₂ | |
| 345 | A | S | (3-OPh)Ph | (2-furfuryl)CH₂ | |
| 346 | A | S | (3-OPh)Ph | (2-thienyl)CH₂ | |
| 347 | A | S | (2-OPh)Ph | n-C₆H₁₃ | amorphous |
| 348 | A | S | (2-OPh)Ph | n-C₄H₉ | |
| 349 | A | S | (2-OPh)Ph | n-C₈H₁₇ | |
| 350 | A | S | (2-OPh)Ph | n-C₁₀H₂₁ | |
| 351 | A | S | (2-OPh)Ph | CH₂Ph | |
| 352 | A | S | (2-OPh)Ph | CH₂(4-F)Ph | |
| 353 | A | S | (2-OPh)Ph | CH₂(4-OCH₃)Ph | |
| 354 | A | S | (2-OPh)Ph | CH₂(4-Cl)Ph | |
| 355 | A | S | (2-OPh)Ph | CH₂(4-OC₄H₉)Ph | |
| 356 | A | S | (2-OPh)Ph | CH₂(3-Cl)Ph | |
| 357 | A | S | (2-OPh)Ph | CH₂(3-F)Ph | |
| 358 | A | S | (2-OPh)Ph | CH₂(3-OCH₃)Ph | |
| 359 | A | S | (2-OPh)Ph | CH₂(3-OC₄H₉)Ph | |
| 360 | A | S | (2-OPh)Ph | CH₂(2-Cl)Ph | |
| 361 | A | S | (2-OPh)Ph | CH₂(2-F)Ph | |
| 362 | A | S | (2-OPh)Ph | CH₂(2-OCH₃)Ph | |
| 363 | A | S | (2-OPh)Ph | CH₂(2-OC₄H₉)Ph | |
| 364 | A | S | (2-OPh)Ph | Ph | |
| 365 | A | S | (2-OPh)Ph | (4-F)Ph | |
| 366 | A | S | (2-OPh)Ph | (4-OCH₃)Ph | |
| 367 | A | S | (2-OPh)Ph | (4-Cl)Ph | |
| 368 | A | S | (2-OPh)Ph | (4-OC₄H₉)Ph | |
| 369 | A | S | (2-OPh)Ph | (4-OPh)Ph | |
| 370 | A | S | (2-OPh)Ph | (4-C₄H₉)Ph | |
| 371 | A | S | (2-OPh)Ph | (4-Ph)Ph | |
| 372 | A | S | (2-OPh)Ph | (3-pyridyl)CH₂ | |
| 373 | A | S | (2-OPh)Ph | (2-furfuryl)CH₂ | |
| 374 | A | S | (2-OPh)Ph | (2-thienyl)CH₂ | |
| 375 | A | S | (4-CF₃)Ph | n-C₆H₁₃ | 174–175 |
| 376 | A | S | (4-CF₃)Ph | n-C₄H₉ | |
| 377 | A | S | (4-CF₃)Ph | n-C₈H₁₇ | |
| 378 | A | S | (4-CF₃)Ph | n-C₁₀H₂₁ | |
| 379 | A | S | (4-CF₃)Ph | CH₂Ph | 203–203.5 |
| 380 | A | S | (4-CF₃)Ph | CH₂(4-F)Ph | 201.5–203 |
| 381 | A | S | (4-CF₃)Ph | CH₂(4-OCH₃)Ph | 190.5–192 |
| 382 | A | S | (4-CF₃)Ph | CH₂(4-Cl)Ph | |

TABLE 1-continued $$\underset{H}{\overset{R^1}{\phantom{x}}}\underset{\phantom{x}}{\overset{O}{\|}}\underset{X}{\overset{R^5}{\phantom{x}}}R^7$$

| Ex. No. | R¹ * | X | R⁵ | R⁷ | m.p. |
|---|---|---|---|---|---|
| 383 | A | S | (4-CF₃)Ph | CH₂(4-OC₄H₉)Ph | |
| 384 | A | S | (4-CF₃)Ph | CH₂(3-Cl)Ph | |
| 385 | A | S | (4-CF₃)Ph | CH₂(3-F)Ph | |
| 386 | A | S | (4-CF₃)Ph | CH₂(3-OCH₃)Ph | |
| 387 | A | S | (4-CF₃)Ph | CH₂(3-OC₄H₉)Ph | |
| 388 | A | S | (4-CF₃)Ph | CH₂(2-Cl)Ph | |
| 389 | A | S | (4-CF₃)Ph | CH₂(2-F)Ph | |
| 390 | A | S | (4-CF₃)Ph | CH₂(2-OCH₃)Ph | |
| 391 | A | S | (4-CF₃)Ph | CH₂(2-OC₄H₉)Ph | |
| 392 | A | S | (4-CF₃)Ph | Ph | |
| 393 | A | S | (4-CF₃)Ph | (4-F)Ph | 217.5–219 |
| 394 | A | S | (4-CF₃)Ph | (4-OCH₃)Ph | 187–189 |
| 395 | A | S | (4-CF₃)Ph | (4-Cl)Ph | |
| 396 | A | S | (4-CF₃)Ph | (4-OC₄H₉)Ph | |
| 397 | A | S | (4-CF₃)Ph | (4-OPh)Ph | |
| 398 | A | S | (4-CF₃)Ph | (4-C₄H₉)Ph | |
| 399 | A | S | (4-CF₃)Ph | (4-Ph)Ph | |
| 400 | A | S | (4-CF₃)Ph | (3-pyridyl)CH₂ | |
| 401 | A | S | (4-CF₃)Ph | (2-furfuryl)CH₂ | |
| 402 | A | S | (4-CF₃)Ph | (2-thienyl)CH₂ | |
| 403 | A | S | (4-iPr)Ph | n-C₆H₁₃ | 109–110 |
| 404 | A | S | (4-iPr)Ph | n-C₄H₉ | |
| 405 | A | S | (4-iPr)Ph | n-C₈H₁₇ | |
| 406 | A | S | (4-iPr)Ph | n-C₁₀H₂₁ | |
| 407 | A | S | (4-iPr)Ph | CH₂Ph | 184–185 |
| 408 | A | S | (4-iPr)Ph | CH₂(4-F)Ph | |
| 409 | A | S | (4-iPr)Ph | CH₂(4-OCH₃)Ph | |
| 410 | A | S | (4-iPr)Ph | CH₂(4-Cl)Ph | 189–190.5 |
| 411 | A | S | (4-iPr)Ph | CH₂(4-OC₄H₉)Ph | 159–161 |
| 412 | A | S | (4-iPr)Ph | CH₂(3-Cl)Ph | |
| 413 | A | S | (4-iPr)Ph | CH₂(3-F)Ph | |
| 414 | A | S | (4-iPr)Ph | CH₂(3-OCH₃)Ph | |
| 415 | A | S | (4-iPr)Ph | CH₂(3-OC₄H₉)Ph | |
| 416 | A | S | (4-iPr)Ph | CH₂(2-Cl)Ph | |
| 417 | A | S | (4-iPr)Ph | CH₂(2-F)Ph | |
| 418 | A | S | (4-iPr)Ph | CH₂(2-OCH₃)Ph | |
| 419 | A | S | (4-iPr)Ph | CH₂(2-OC₄H₉)Ph | |
| 420 | A | S | (4-iPr)Ph | Ph | |
| 421 | A | S | (4-iPr)Ph | (4-F)Ph | |
| 422 | A | S | (4-iPr)Ph | (4-OCH₃)Ph | |
| 423 | A | S | (4-iPr)Ph | (4-Cl)Ph | |
| 424 | A | S | (4-iPr)Ph | (4-OC₄H₉)Ph | |
| 425 | A | S | (4-iPr)Ph | (4-OPh)Ph | |
| 426 | A | S | (4-iPr)Ph | (4-C₄H₉)Ph | |
| 427 | A | S | (4-iPr)Ph | (4-Ph)Ph | |
| 428 | A | S | (4-iPr)Ph | (3-pyridyl)CH₂ | |
| 429 | A | S | (4-iPr)Ph | (2-furfuryl)CH₂ | |
| 430 | A | S | (4-iPr)Ph | (2-thienyl)CH₂ | |
| 431 | A | S | (4-tBu)Ph | n-C₆H₁₃ | 144.5 |
| 432 | A | S | (4-tBu)Ph | n-C₄H₉ | |
| 433 | A | S | (4-tBu)Ph | n-C₈H₁₇ | |
| 434 | A | S | (4-tBu)Ph | n-C₁₀H₂₁ | |
| 435 | A | S | (4-tBu)Ph | CH₂Ph | 197.1 |
| 436 | A | S | (4-tBu)Ph | CH₂(4-F)Ph | |
| 437 | A | S | (4-tBu)Ph | CH₂(4-Cl)Ph | 202.7 |
| 438 | A | S | (4-tBu)Ph | CH₂(4-OC₄H₉)Ph | |
| 439 | A | S | (4-tBu)Ph | CH₂(4-tBu)Ph | 197.1 |
| 440 | A | S | (4-tBu)Ph | CH₂(3-Cl)Ph | |
| 441 | A | S | (4-tBu)Ph | CH₂(3-F)Ph | |
| 442 | A | S | (4-tBu)Ph | CH₂(3-OCH₃)Ph | |
| 443 | A | S | (4-tBu)Ph | CH₂(3-OC₄H₉)Ph | |
| 444 | A | S | (4-tBu)Ph | CH₂(2-Cl)Ph | |
| 445 | A | S | (4-tBu)Ph | CH₂(2-F)Ph | |
| 446 | A | S | (4-tBu)Ph | CH₂(2-OCH₃)Ph | |
| 447 | A | S | (4-tBu)Ph | CH₂(2-OC₄H₉)Ph | |
| 448 | A | S | (4-tBu)Ph | Ph | |
| 449 | A | S | (4-tBu)Ph | (4-F)Ph | |
| 450 | A | S | (4-tBu)Ph | (4-OCH₃)Ph | |
| 451 | A | S | (4-tBu)Ph | (4-Cl)Ph | |
| 452 | A | S | (4-tBu)Ph | (4-OC₄H₉)Ph | |
| 453 | A | S | (4-tBu)Ph | (4-OPh)Ph | |
| 454 | A | S | (4-tBu)Ph | (4-C₄H₉)Ph | |
| 455 | A | S | (4-tBu)Ph | (4-Ph)Ph | |
| 456 | A | S | (4-tBu)Ph | (3-pyridyl)CH₂ | |
| 457 | A | S | (4-tBu)Ph | (2-furfuryl)CH₂ | |
| 458 | A | S | (4-tBu)Ph | (2-thienyl)CH₂ | |
| 459 | A | S | (4-Ph)Ph | n-C₆H₁₃ | amorphous |
| 460 | A | S | (4-Ph)Ph | n-C₄H₉ | |
| 461 | A | S | (4-Ph)Ph | n-C₈H₁₇ | |
| 462 | A | S | (4-Ph)Ph | n-C₁₀H₂₁ | |
| 463 | A | S | (4-Ph)Ph | CH₂Ph | amorphous |
| 464 | A | S | (4-Ph)Ph | CH₂(4-F)Ph | 209–211 |
| 465 | A | S | (4-Ph)Ph | CH₂(4-OCH₃)Ph | 194–196 |
| 466 | A | S | (4-Ph)Ph | CH₂(4-Cl)Ph | |
| 467 | A | S | (4-Ph)Ph | CH₂(4-OC₄H₉)Ph | 164.6 |
| 468 | A | S | (4-Ph)Ph | CH₂(3-Cl)Ph | |
| 469 | A | S | (4-Ph)Ph | CH₂(3-F)Ph | |
| 470 | A | S | (4-Ph)Ph | CH₂(3-OCH₃)Ph | |
| 471 | A | S | (4-Ph)Ph | CH₂(3-OC₄H₉)Ph | |
| 472 | A | S | (4-Ph)Ph | CH₂(2-Cl)Ph | |
| 473 | A | S | (4-Ph)Ph | CH₂(2-F)Ph | |
| 474 | A | S | (4-Ph)Ph | CH₂(2-OCH₃)Ph | |
| 475 | A | S | (4-Ph)Ph | CH₂(2-OC₄H₉)Ph | |
| 476 | A | S | (4-Ph)Ph | Ph | |
| 477 | A | S | (4-Ph)Ph | (4-F)Ph | |
| 478 | A | S | (4-Ph)Ph | (4-OCH₃)Ph | |
| 479 | A | S | (4-Ph)Ph | (4-Cl)Ph | |
| 480 | A | S | (4-Ph)Ph | (4-OC₄H₉)Ph | |
| 481 | A | S | (4-Ph)Ph | (4-OPh)Ph | |
| 482 | A | S | (4-Ph)Ph | (4-C₄H₉)Ph | |
| 483 | A | S | (4-Ph)Ph | (4-Ph)Ph | |
| 484 | A | S | (4-Ph)Ph | (3-pyridyl)CH₂ | 209–211 |
| 485 | A | S | (4-Ph)Ph | (2-furfuryl)CH₂ | |
| 486 | A | S | (4-Ph)Ph | (2-thienyl)CH₂ | |
| 487 | A | S | (4-NO₂)Ph | n-C₆H₁₃ | amorphous |
| 488 | A | S | (4-NO₂)Ph | n-C₄H₉ | |
| 489 | A | S | (4-NO₂)Ph | n-C₈H₁₇ | |
| 490 | A | S | (4-NO₂)Ph | n-C₁₀H₂₁ | |
| 491 | A | S | (4-NO₂)Ph | CH₂Ph | |
| 492 | A | S | (4-NO₂)Ph | CH₂(4-F)Ph | |
| 493 | A | S | (4-NO₂)Ph | CH₂(4-OCH₃)Ph | |
| 494 | A | S | (4-NO₂)Ph | CH₂(4-Cl)Ph | |
| 495 | A | S | (4-NO₂)Ph | CH₂(4-OC₄H₉)Ph | |
| 496 | A | S | (4-NO₂)Ph | CH₂(3-Cl)Ph | |
| 497 | A | S | (4-NO₂)Ph | CH₂(3-F)Ph | |
| 498 | A | S | (4-NO₂)Ph | CH₂(3-OCH₃)Ph | |
| 499 | A | S | (4-NO₂)Ph | CH₂(3-OC₄H₉)Ph | |
| 500 | A | S | (4-NO₂)Ph | CH₂(2-Cl)Ph | |
| 501 | A | S | (4-NO₂)Ph | CH₂(2-F)Ph | |
| 502 | A | S | (4-NO₂)Ph | CH₂(2-OCH₃)Ph | |
| 503 | A | S | (4-NO₂)Ph | CH₂(2-OC₄H₉)Ph | |
| 504 | A | S | (4-NO₂)Ph | Ph | |
| 505 | A | S | (4-NO₂)Ph | (4-F)Ph | |
| 506 | A | S | (4-NO₂)Ph | (4-OCH₃)Ph | |
| 507 | A | S | (4-NO₂)Ph | (4-Cl)Ph | |
| 508 | A | S | (4-NO₂)Ph | (4-OC₄H₉)Ph | |
| 509 | A | S | (4-NO₂)Ph | (4-OPh)Ph | |
| 510 | A | S | (4-NO₂)Ph | (4-C₄H₉)Ph | |
| 511 | A | S | (4-NO₂)Ph | (4-Ph)Ph | |
| 512 | A | S | (4-NO₂)Ph | (3-pyridyl)CH₂ | |
| 513 | A | S | (4-NO₂)Ph | (2-furfuryl)CH₂ | |
| 514 | A | S | (4-NO₂)Ph | (2-thienyl)CH₂ | |
| 515 | A | S | (3,4-OCH₂O)Ph | n-C₆H₁₃ | amorphous |

TABLE 1-continued

| Ex. No. | R¹ * | X | R⁵ | R⁷ | m.p. |
|---|---|---|---|---|---|
| 516 | A | S | (3,4-OCH₂O)Ph | n-C₄H₉ | |
| 517 | A | S | (3,4-OCH₂O)Ph | n-C₆H₁₇ | |
| 518 | A | S | (3,4-OCH₂O)Ph | n-C₁₀H₂₁ | |
| 519 | A | S | (3,4-OCH₂O)Ph | CH₂Ph | |
| 520 | A | S | (3,4-OCH₂O)Ph | CH₂(4-F)Ph | |
| 521 | A | S | (3,4-OCH₂O)Ph | CH₂(4-OCH₃)Ph | |
| 522 | A | S | (3,4-OCH₂O)Ph | CH₂(4-Cl)Ph | amorphous |
| 523 | A | S | (3,4-OCH₂O)Ph | CH₂(4-OC₄H₉)Ph | |
| 524 | A | S | (3,4-OCH₂O)Ph | CH₂(3-Cl)Ph | |
| 525 | A | S | (3,4-OCH₂O)Ph | CH₂(3-F)Ph | |
| 526 | A | S | (3,4-OCH₂O)Ph | CH₂(3-OCH₃)Ph | |
| 527 | A | S | (3,4-OCH₂O)Ph | CH₂(3-OC₄H₉)Ph | |
| 528 | A | S | (3,4-OCH₂O)Ph | CH₂(2-Cl)Ph | |
| 529 | A | S | (3,4-OCH₂O)Ph | CH₂(2-F)Ph | |
| 530 | A | S | (3,4-OCH₂O)Ph | CH₂(2-OCH₃)Ph | |
| 531 | A | S | (3,4-OCH₂O)Ph | CH₂(2-OC₄H₉)Ph | |
| 532 | A | S | (3,4-OCH₂O)Ph | Ph | |
| 533 | A | S | (3,4-OCH₂O)Ph | (4-F)Ph | |
| 534 | A | S | (3,4-OCH₂O)Ph | (4-OCH₃)Ph | |
| 535 | A | S | (3,4-OCH₂O)Ph | (4-Cl)Ph | |
| 536 | A | S | (3,4-OCH₂O)Ph | (4-OC₄H₉)Ph | |
| 537 | A | S | (3,4-OCH₂O)Ph | (4-OPh)Ph | |
| 538 | A | S | (3,4-OCH₂O)Ph | (4-C₄H₉)Ph | |
| 539 | A | S | (3,4-OCH₂O)Ph | (4-Ph)Ph | |
| 540 | A | S | (3,4-OCH₂O)Ph | (3-pyridyl)CH₂ | |
| 541 | A | S | (3,4-OCH₂O)Ph | (2-furfuryl)CH₂ | |
| 542 | A | S | (3,4-OCH₂O)Ph | (2-thienyl)CH₂ | |
| 543 | A | S | 2-thienyl | n-C₆H₁₃ | 122.5–123.5 |
| 544 | A | S | 2-thienyl | n-C₄H₉ | |
| 545 | A | S | 2-thienyl | n-C₈H₁₇ | |
| 546 | A | S | 2-thienyl | n-C₁₀H₂₁ | |
| 547 | A | S | 2-thienyl | CH₂Ph | |
| 548 | A | S | 2-thienyl | CH₂(4-F)Ph | |
| 549 | A | S | 2-thienyl | CH₂(4-OCH₃)Ph | |
| 550 | A | S | 2-thienyl | CH₂(4-Cl)Ph | |
| 551 | A | S | 2-thienyl | CH₂(4-OC₄H₉)Ph | |
| 552 | A | S | 2-thienyl | CH₂(3-Cl)Ph | |
| 553 | A | S | 2-thienyl | CH₂(3-F)Ph | |
| 554 | A | S | 2-thienyl | CH₂(3-OCH₃)Ph | |
| 555 | A | S | 2-thienyl | CH₂(3-OC₄H₉)Ph | |
| 556 | A | S | 2-thienyl | CH₂(2-Cl)Ph | |
| 557 | A | S | 2-thienyl | CH₂(2-F)Ph | |
| 558 | A | S | 2-thienyl | CH₂(2-OCH₃)Ph | |
| 559 | A | S | 2-thienyl | CH₂(2-OC₄H₉)Ph | |
| 560 | A | S | 2-thienyl | Ph | |
| 561 | A | S | 2-thienyl | (4-F)Ph | |
| 562 | A | S | 2-thienyl | (4-OCH₃)Ph | |
| 563 | A | S | 2-thienyl | (4-Cl)Ph | |
| 564 | A | S | 2-thienyl | (4-OC₄H₉)Ph | |
| 565 | A | S | 2-thienyl | (4-OPh)Ph | |
| 567 | A | S | 2-thienyl | (4-C₄H₉)Ph | |
| 568 | A | S | 2-thienyl | (4-Ph)Ph | |
| 569 | A | S | 2-thienyl | (3-pyridyl)CH₂ | |
| 570 | A | S | 2-thienyl | (2-furfuryl)CH₂ | |
| 571 | A | S | 2-thienyl | (2-thienyl)CH₂ | |
| 572 | A | S | 2-furfuryl | n-C₆H₁₃ | |
| 573 | A | S | 2-furfuryl | n-C₄H₉ | |
| 574 | A | S | 2-furfuryl | n-C₈H₁₇ | |
| 575 | A | S | 2-furfuryl | n-C₁₀H₂₁ | |
| 576 | A | S | 2-furfuryl | CH₂Ph | |
| 577 | A | S | 2-furfuryl | CH₂(4-F)Ph | |
| 578 | A | S | 2-furfuryl | CH₂(4-OCH₃)Ph | |
| 579 | A | S | 2-furfuryl | CH₂(4-Cl)Ph | |
| 580 | A | S | 2-furfuryl | CH₂(4-OC₄H₉)Ph | |
| 581 | A | S | 2-furfuryl | CH₂(3-Cl)Ph | |
| 582 | A | S | 2-furfuryl | CH₂(3-F)Ph | |
| 583 | A | S | 2-furfuryl | CH₂(3-OCH₃)Ph | |
| 584 | A | S | 2-furfuryl | CH₂(3-OC₄H₉)Ph | |
| 585 | A | S | 2-furfuryl | CH₂(2-Cl)Ph | |
| 586 | A | S | 2-furfuryl | CH₂(2-F)Ph | |
| 587 | A | S | 2-furfuryl | CH₂(2-OCH₃)Ph | |
| 588 | A | S | 2-furfuryl | CH₂(2-OC₄H₉)Ph | |
| 589 | A | S | 2-furfuryl | Ph | |
| 590 | A | S | 2-furfuryl | (4-F)Ph | |
| 591 | A | S | 2-furfuryl | (4-OCH₃)Ph | |
| 592 | A | S | 2-furfuryl | (4-Cl)Ph | |
| 593 | A | S | 2-furfuryl | (4-OC₄H₉)Ph | |
| 594 | A | S | 2-furfuryl | (4-OPh)Ph | |
| 595 | A | S | 2-furfuryl | (4-C₄H₉)Ph | |
| 596 | A | S | 2-furfuryl | (4-Ph)Ph | |
| 597 | A | S | 2-furfuryl | (3-pyridyl)CH₂ | |
| 598 | A | S | 2-furfuryl | (2-furfuryl)CH₂ | |
| 599 | A | S | 2-furfuryl | (2-thienyl)CH₂ | |
| 600 | A | S | (4-nBu)Ph | n-C₆H₁₃ | 99.5–100.5 |
| 601 | A | S | (4-nBu)Ph | n-C₄H₉ | |
| 602 | A | S | (4-nBu)Ph | n-C₈H₁₇ | |
| 603 | A | S | (4-nBu)Ph | n-C₁₀H₂₁ | |
| 604 | A | S | (4-nBu)Ph | CH₂Ph | |
| 605 | A | S | (4-nBu)Ph | CH₂(4-F)Ph | |
| 606 | A | S | (4-nBu)Ph | CH₂(4-OCH₃)Ph | |
| 607 | A | S | (4-nBu)Ph | CH₂(4-Cl)Ph | 138–140 |
| 608 | A | S | (4-nBu)Ph | CH₂(4-OC₄H₉)Ph | |
| 609 | A | S | (4-nBu)Ph | CH₂(3-Cl)Ph | |
| 610 | A | S | (4-nBu)Ph | CH₂(3-F)Ph | |
| 611 | A | S | (4-nBu)Ph | CH₂(3-OCH₃)Ph | |
| 612 | A | S | (4-nBu)Ph | CH₂(3-OC₄H₉)Ph | |
| 613 | A | S | (4-nBu)Ph | CH₂(2-Cl)Ph | |
| 614 | A | S | (4-nBu)Ph | CH₂(2-F)Ph | |
| 615 | A | S | (4-nBu)Ph | CH₂(2-OCH₃)Ph | |
| 616 | A | S | (4-nBu)Ph | CH₂(2-OC₄H₉)Ph | |
| 617 | A | S | (4-nBu)Ph | CH₂(4-C₄H₉)Ph | 135–137 |
| 618 | A | S | (4-nBu)Ph | Ph | |
| 619 | A | S | (4-nBu)Ph | (4-F)Ph | |
| 620 | A | S | (4-nBu)Ph | (4-OCH₃)Ph | |
| 621 | A | S | (4-nBu)Ph | (4-Cl)Ph | |
| 622 | A | S | (4-nBu)Ph | (4-OC₄H₉)Ph | |
| 623 | A | S | (4-nBu)Ph | (4-OPh)Ph | |
| 624 | A | S | (4-nBu)Ph | (4-C₄H₉)Ph | |
| 625 | A | S | (4-nBu)Ph | (4-Ph)Ph | |
| 626 | A | S | (4-nBu)Ph | (3-pyridyl)CH₂ | |
| 627 | A | S | (4-nBu)Ph | (2-furfuryl)CH₂ | |
| 628 | A | S | (4-nBu)Ph | (2-thienyl)CH₂ | |

*R¹

A = 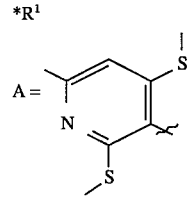

TABLE 1-continued

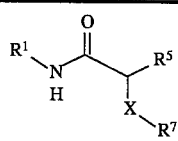

| Ex. No. | R¹ * | X | R⁵ | R⁷ | m.p. |
|---|---|---|---|---|---|

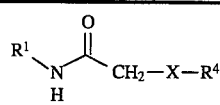

TABLE 2

$R^1\text{-NH-C(=O)-CH}_2\text{-X-R}^4$

| Ex. No. | R¹ (see footnote a for definitions) | R⁴ (see footnote b for definitions) | X | m.p., °C. |
|---|---|---|---|---|
| 1001 | I | A | S | — |
| 1002 | I | B | S | — |
| 1003 | I | C | S | 95–97 |
| 1004 | I | D | S | 108–110 |
| 1005 | I | E | S | 78–79 |
| 1006 | I | F | S | — |
| 1007 | I | G | S | — |
| 1008 | I | H | S | — |
| 1009 | I | J | S | 88–89 |
| 1010 | I | K | S | 86–88 |
| 1011 | I | L | S | — |
| 1012 | I | M | S | — |
| 1013 | I | N | S | — |
| 1014 | I | P | S | — |
| 1015 | I | Q | S | — |
| 1016 | I | R | S | — |
| 1017 | I | S | S | — |
| 1018 | I | T | S | — |
| 1019 | I | U | S | — |
| 1020 | I | V | S | 60–62 |
| 1021 | I | W | S | — |
| 1022 | I | X | S | 116–118 |
| 1023 | I | Y | S | — |
| 1024 | I | Z | S | — |
| 1025 | I | AA | S | — |
| 1026 | I | BB | S | — |
| 1027 | I | CC | S | — |
| 1028 | I | DD | S | 178–180 |
| 1029 | I | EE | S | 101–103 |
| 1030 | I | FF | S | — |
| 1031 | I | GG | S | 76–77 |
| 1032 | I | HH | S | 100–101 |
| 1033 | I | JJ | S | — |
| 1034 | I | KK | S | — |
| 1035 | I | LL | S | — |
| 1036 | I | MM | S | — |
| 1037 | I | NN | S | — |
| 1038 | I | PP | S | 66–68 |
| 1039 | I | QQ | S | 75–77 |
| 1040 | I | RR | S | — |
| 1041 | I | SS | S | — |
| 1042 | I | TT | S | — |

TABLE 2-continued

| Ex. No. | R¹ | R⁴ | X | m.p., °C. |
|---|---|---|---|---|
| 1043 | I | UU | S | 165–167 |
| 1044 | I | VV | S | — |
| 1045 | I | WW | S | — |
| 1046 | I | XX | S | 137–139 |
| 1047 | I | YY | S | 123–125 |
| 1048 | I | ZZ | S | 68–70 |
| 1049 | I | AAA | S | 155–157 |
| 1050 | II | A | S | — |
| 1051 | II | B | S | — |
| 1052 | II | C | S | — |
| 1053 | II | D | S | — |
| 1054 | II | E | S | — |
| 1055 | II | F | S | — |
| 1056 | II | G | S | — |
| 1057 | II | H | S | — |
| 1058 | II | J | S | — |
| 1059 | II | K | S | — |
| 1060 | II | L | S | — |
| 1061 | II | M | S | — |
| 1062 | II | N | S | — |
| 1063 | II | P | S | — |
| 1064 | II | Q | S | — |
| 1065 | II | R | S | — |
| 1066 | II | S | S | — |
| 1067 | II | T | S | — |
| 1068 | II | U | S | — |
| 1069 | II | V | S | — |
| 1070 | II | W | S | — |
| 1071 | II | X | S | — |
| 1072 | II | Y | S | — |
| 1073 | II | Z | S | — |
| 1074 | II | AA | S | — |
| 1075 | II | BB | S | — |
| 1076 | II | CC | S | — |
| 1077 | II | DD | S | — |
| 1078 | II | EE | S | — |
| 1079 | II | FF | S | — |
| 1080 | II | GG | S | — |
| 1081 | II | HH | S | — |
| 1082 | II | JJ | S | — |
| 1083 | II | KK | S | — |
| 1084 | II | LL | S | — |
| 1085 | II | MM | S | — |
| 1086 | II | NN | S | — |
| 1087 | II | PP | S | — |
| 1088 | II | QQ | S | — |
| 1089 | II | RR | S | — |
| 1090 | II | SS | S | — |
| 1091 | II | TT | S | — |
| 1092 | II | UU | S | — |
| 1093 | II | VV | S | — |
| 1094 | II | WW | S | — |
| 1095 | II | XX | S | — |
| 1096 | II | YY | S | — |
| 1097 | II | ZZ | S | — |
| 1098 | II | AAA | S | — |
| 1099 | III | A | S | — |
| 1100 | III | B | S | — |
| 1101 | III | C | S | — |
| 1102 | III | D | S | — |
| 1103 | III | E | S | — |
| 1104 | III | F | S | — |
| 1105 | III | G | S | — |
| 1106 | III | H | S | — |
| 1107 | III | J | S | — |
| 1108 | III | K | S | — |
| 1109 | III | L | S | — |
| 1110 | III | M | S | — |
| 1111 | III | N | S | — |
| 1112 | III | P | S | — |
| 1113 | III | Q | S | — |
| 1114 | III | R | S | — |
| 1115 | III | S | S | — |
| 1116 | III | T | S | — |
| 1117 | III | U | S | — |
| 1118 | III | V | S | — |
| 1119 | III | W | S | — |
| 1120 | III | X | S | — |
| 1121 | III | Y | S | — |

TABLE 2-continued

| | | | | |
|---|---|---|---|---|
| 1122 | III | Z | S | — |
| 1123 | III | AA | S | — |
| 1124 | III | BB | S | — |
| 1125 | III | CC | S | — |
| 1126 | III | DD | S | — |
| 1127 | III | EE | S | — |
| 1128 | III | FF | S | — |
| 1129 | III | GG | S | — |
| 1130 | III | HH | S | — |
| 1131 | III | JJ | S | — |
| 1132 | III | KK | S | — |
| 1133 | III | LL | S | — |
| 1134 | III | MM | S | — |
| 1135 | III | NN | S | — |
| 1136 | III | PP | S | — |
| 1137 | III | QQ | S | — |
| 1138 | III | RR | S | — |
| 1139 | III | SS | S | — |
| 1140 | III | TT | S | — |
| 1141 | III | UU | S | — |
| 1142 | III | VV | S | — |
| 1143 | III | WW | S | — |
| 1144 | III | XX | S | — |
| 1145 | III | YY | S | — |
| 1146 | III | ZZ | S | — |
| 1147 | III | AAA | S | — |
| 1148 | IV | A | S | — |
| 1149 | IV | B | S | — |
| 1150 | IV | C | S | — |
| 1151 | IV | D | S | — |
| 1152 | IV | E | S | — |
| 1153 | IV | F | S | — |
| 1154 | IV | G | S | — |
| 1155 | IV | H | S | — |
| 1156 | IV | J | S | — |
| 1157 | IV | K | S | — |
| 1158 | IV | L | S | — |
| 1159 | IV | M | S | — |
| 1160 | IV | N | S | — |
| 1161 | IV | P | S | — |
| 1162 | IV | Q | S | — |
| 1163 | IV | R | S | — |
| 1164 | IV | S | S | — |
| 1165 | IV | T | S | — |
| 1166 | IV | U | S | — |
| 1167 | IV | V | S | — |
| 1168 | IV | W | S | — |
| 1169 | IV | X | S | — |
| 1170 | IV | Y | S | — |
| 1171 | IV | Z | S | — |
| 1172 | IV | AA | S | — |
| 1173 | IV | BB | S | — |
| 1174 | IV | CC | S | — |
| 1175 | IV | DD | S | — |
| 1176 | IV | EE | S | — |
| 1177 | IV | FF | S | — |
| 1178 | IV | GG | S | — |
| 1179 | IV | HH | S | — |
| 1180 | IV | JJ | S | — |
| 1181 | IV | KK | S | — |
| 1182 | IV | LL | S | — |
| 1183 | IV | MM | S | — |
| 1184 | IV | NN | S | — |
| 1185 | IV | PP | S | — |
| 1186 | IV | QQ | S | — |
| 1187 | IV | RR | S | — |
| 1188 | IV | SS | S | — |
| 1189 | IV | TT | S | — |
| 1190 | IV | UU | S | — |
| 1191 | IV | VV | S | — |
| 1192 | IV | WW | S | — |
| 1193 | IV | XX | S | — |
| 1194 | IV | YY | S | — |
| 1195 | IV | ZZ | S | — |
| 1196 | IV | AAA | S | — |
| 1197 | V | A | S | — |
| 1198 | V | B | S | — |
| 1199 | V | C | S | — |
| 1200 | V | D | S | — |
| 1201 | V | E | S | — |
| 1202 | V | F | S | — |
| 1203 | V | G | S | — |
| 1204 | V | H | S | — |
| 1205 | V | J | S | — |
| 1206 | V | K | S | — |
| 1207 | V | L | S | — |
| 1208 | V | M | S | — |
| 1209 | V | N | S | — |
| 1210 | V | P | S | — |
| 1211 | V | Q | S | — |
| 1212 | V | R | S | — |
| 1213 | V | S | S | — |
| 1214 | V | T | S | — |
| 1215 | V | U | S | — |
| 1216 | V | V | S | — |
| 1217 | V | W | S | — |
| 1218 | V | X | S | — |
| 1219 | V | Y | S | — |
| 1220 | V | Z | S | — |
| 1221 | V | AA | S | — |
| 1222 | V | BB | S | — |
| 1223 | V | CC | S | — |
| 1224 | V | DD | S | — |
| 1225 | V | EE | S | — |
| 1226 | V | FF | S | — |
| 1227 | V | GG | S | — |
| 1228 | V | HH | S | — |
| 1229 | V | JJ | S | — |
| 1230 | V | KK | S | — |
| 1231 | V | LL | S | — |
| 1232 | V | MM | S | — |
| 1233 | V | NN | S | — |
| 1234 | V | PP | S | — |
| 1235 | V | QQ | S | — |
| 1236 | V | RR | S | — |
| 1237 | V | SS | S | — |
| 1238 | V | TT | S | — |
| 1239 | V | UU | S | — |
| 1240 | V | VV | S | — |
| 1241 | V | WW | S | — |
| 1242 | V | XX | S | — |
| 1243 | V | YY | S | — |
| 1244 | V | ZZ | S | — |
| 1245 | V | AAA | S | — |
| 1246 | VI | N | S | — |
| 1247 | VI | P | S | — |
| 1248 | VI | Q | S | — |
| 1249 | VI | T | S | — |
| 1250 | VI | U | S | — |
| 1251 | VI | V | S | — |
| 1252 | VI | EE | S | — |
| 1253 | VI | FF | S | — |
| 1254 | VI | GG | S | — |
| 1255 | VI | HH | S | — |
| 1256 | VI | JJ | S | — |
| 1257 | VI | KK | S | — |
| 1258 | VI | LL | S | — |
| 1259 | VI | MM | S | — |
| 1260 | VI | PP | S | — |
| 1261 | VI | QQ | S | — |
| 1262 | VI | RR | S | — |
| 1263 | VI | SS | S | — |
| 1264 | VI | TT | S | — |
| 1265 | VI | UU | S | — |
| 1266 | VI | VV | S | — |
| 1267 | VI | WW | S | — |
| 1268 | VI | XX | S | — |
| 1269 | VI | YY | S | — |
| 1270 | VI | ZZ | S | — |
| 1271 | VI | AAA | S | — |
| 1272 | VII | N | S | — |
| 1273 | VII | P | S | — |
| 1274 | VII | Q | S | — |
| 1275 | VII | T | S | — |
| 1276 | VII | U | S | — |
| 1277 | VII | V | S | — |
| 1278 | VII | EE | S | — |
| 1279 | VII | FF | S | — |

TABLE 2-continued

| | | | | |
|---|---|---|---|---|
| 1280 | VII | GG | S | — |
| 1281 | VII | HH | S | — |
| 1282 | VII | JJ | S | — |
| 1283 | VII | KK | S | — |
| 1284 | VII | LL | S | — |
| 1285 | VII | MM | S | — |
| 1286 | VII | PP | S | oil[c] |
| 1287 | VII | QQ | S | — |
| 1288 | VII | RR | S | — |
| 1289 | VII | SS | S | — |
| 1290 | VII | TT | S | — |
| 1291 | VII | UU | S | — |
| 1292 | VII | VV | S | — |
| 1293 | VII | WW | S | — |
| 1294 | VII | XX | S | — |
| 1295 | VII | YY | S | — |
| 1296 | VII | ZZ | S | — |
| 1297 | VII | AAA | S | — |
| 1298 | VIII | N | S | — |
| 1299 | VIII | P | S | — |
| 1300 | VIII | Q | S | — |
| 1301 | VIII | T | S | — |
| 1302 | VIII | U | S | — |
| 1303 | VIII | V | S | — |
| 1304 | VIII | EE | S | — |
| 1305 | VIII | FF | S | — |
| 1306 | VIII | GG | S | — |
| 1307 | VIII | HH | S | — |
| 1308 | VIII | JJ | S | — |
| 1309 | VIII | KK | S | — |
| 1310 | VIII | LL | S | — |
| 1311 | VIII | MM | S | — |
| 1312 | VIII | PP | S | 79–80 |
| 1313 | VIII | QQ | S | — |
| 1314 | VIII | RR | S | — |
| 1315 | VIII | SS | S | — |
| 1316 | VIII | TT | S | — |
| 1317 | VIII | UU | S | — |
| 1318 | VIII | VV | S | — |
| 1319 | VIII | WW | S | — |
| 1320 | VIII | XX | S | — |
| 1321 | VIII | YY | S | — |
| 1322 | VIII | ZZ | S | — |
| 1323 | VIII | AAA | S | — |
| 1324 | I | A | SO | — |
| 1325 | I | B | SO | — |
| 1326 | I | A | SO$_2$ | — |
| 1327 | I | B | SO$_2$ | — |
| 1328 | I | A | O | — |
| 1329 | I | B | O | — |
| 1330 | I | M | O | — |
| 1331 | I | N | O | — |
| 1332 | I | P | O | — |
| 1333 | I | Q | O | — |

Footnotes to Table 1 a $R^1$ Groups:

I = [CH$_3$-pyridine with SCH$_3$, NH, SCH$_3$ substituents]

II = [CH$_3$-pyrimidine with SCH$_3$, NH, SCH$_3$ substituents]

III = [1,3,5-trimethylpyrazole-4-NH]

IV = [1,3-dimethyl-5-SCH$_3$-pyrazole-4-NH]

V = [quinoline with 4-SCH$_3$, 3-NH, 2-SCH$_3$]

VI = [2,6-di(isopropyl)phenyl-NH]

VII = [2,6-dichlorophenyl-NH]

VIII = [2,6-dimethylphenyl-NH]

b $R^4$ Groups:

A = CH$_3$–CH(CH$_3$)–(CH$_2$)$_2$

B = CH$_3$–CH(CH$_3$)–(CH$_2$)$_3$

C = CH$_3$(CH$_2$)$_3$–CH(CH$_3$CH$_2$)–CH$_2$

D = CH$_3$(CH$_2$)$_3$–CH(CH$_3$(CH$_2$)$_3$)–CH$_2$

E = CH$_3$(CH$_2$)$_3$–CH(CH$_3$(CH$_2$)$_7$)–CH$_2$

F = CH$_3$(CH$_2$)$_4$–CH(CH$_3$(CH$_2$)$_4$)–CH$_2$

TABLE 2-continued

G = CH₃(CH₂)₂CH(CH₂CH₃)CH₂—

H = CH₃CH₂CH(CH₂CH₃)CH₂—

J = CH₃(CH₂)₇CH(CH₂CH₃)CH₂—

K = CH₃(CH₂)₇CH(CH₂(CH₂)₇CH₃)CH₂—

L = (CH₃)₂CH(CH₂)₂CH(CH(CH₂)₂(CH₃)₂)CH₂—

M = CH(OCH₂(CH₂)₃CH₃)(OCH₂(CH₂)₃CH₃)—

N = CH(OCH₂(CH₂)₇CH₃)(OCH₂(CH₂)₇CH₃)—

P = CH₃(CH₂)₃OCH₂CH(OCH₂(CH₂)₃CH₃)CH₂—

Q = CH₃(CH₂)₇OCH₂CH(OCH₂(CH₂)₇CH₃)CH₂—

R = C₆H₅CH(CH₃)CH₂—

S = C₆H₅CH(CH₃)(CH₂)₂—

T = C₆H₅CH₂CH(CH₂(CH₂)₃CH₃)CH₂—

U = 4-Cl-C₆H₄CH₂CH(CH₂(CH₂)₃CH₃)CH₂—

V = 3,4-(MeO)₂-C₆H₃CH₂CH(CH₂(CH₂)₃CH₃)CH₂—

W = C₆H₅CH(CH₂(CH₂)₃CH₃)CH₂—

X = C₆H₅CH(CH₂(CH₂)₄CH₃)CH₂—

Y = 4-Cl-C₆H₄CH(CH₂(CH₂)₄CH₃)CH₂—

Z = 4-MeO-C₆H₄CH(CH₂(CH₂)₄CH₃)CH₂—

AA = (C₆H₅)(C₆H₅)CHCH₂—

BB = (4-Cl-C₆H₄)(4-Cl-C₆H₄)CHCH₂—

TABLE 2-continued
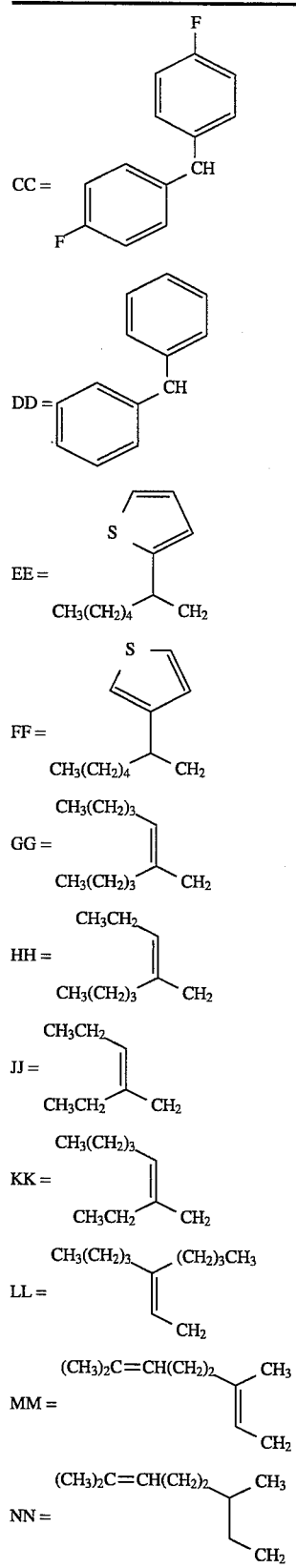
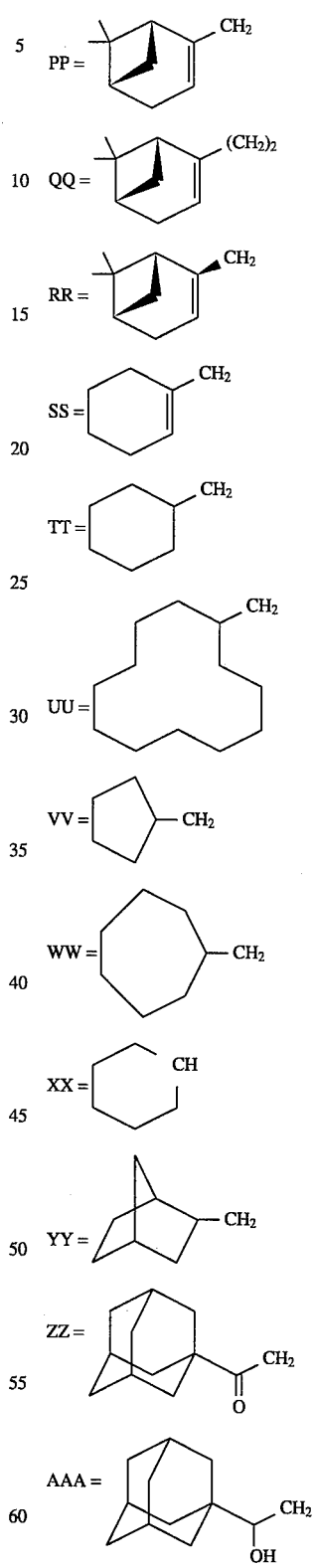

TABLE 3

[Structure: pyridine with SCH₃ at positions 2 and 4, CH₃ at position 6, and NH-C(=O)-R at position 3]

| Ex. No. | R | m.p. | M.S(M⁺ + H) |
|---|---|---|---|
| 2001 | 4-(CF₂-)-C₆H₄-CH₂-C(CH₃)₂- (neopentyl-type) | 134.9–135.4 | 411.0 |
| 2002 | -CF₂-CH(CH₃)-C₆H₅ (with H shown) | 104.8–106.8 | 397.0 |
| 2003 | 4-(CF₂-)-C₆H₄-CH₂-C(CF₃)₂F | 169.0–169.2 | 523.0 |
| 2004 | 4-(CF₂-)-C₆H₄-C(CH₃)₃ | 158.0–158.5 | 411.0 |
| 2005 | 4-(CF₂-)-cyclohexyl-CH₂-CH(CH₃)₂ | 173.3–173.3 | 417.2 |
| 2006 | 4-F-C₆H₄-CF₂- | 168.4–169.4 | 373.0 |
| 2007 | C₆H₅-CF₂- | 145.8–146.5 | 355.0 |
| 2008 | 4-OCH₃-C₆H₄-C(=O)- | 153.5–155.2 | 363.0 |
| 2009 | 3-NO₂-C₆H₄-CF₂- | 127.1–128.7 | 399.9 |
| 2010 | 3-(C₆H₅O)-C₆H₄-CF₂- | 147.1–148.0 | 447.1 |
| 2011 | 3-OCH₃-C₆H₄-CF₂- | 125.4–125.9 | 385.0 |
| 2012 | 3,4-diF-C₆H₃-CF₂- | 153.2–154.4 | 391.0 |

TABLE 3-continued

[Structure: pyridine with SCH3, NHC(=O)R, SCH3, and H3C-N substituents]

| Ex. No. | R | m.p. | M.S(M⁺ + H) |
|---|---|---|---|
| 2013 | 3,4-dimethoxy-CF$_2$-phenyl (OCH$_3$, OCH$_3$, CF$_2$) | 169.8–170.6 | 415.0 |
| 2014 | 2-(benzylthio)-CF$_2$-phenyl | 118.3–118.9 | 477.0 |
| 2015 | 3,4-dichlorobenzoyl | 225–226 | 373.0 |
| 2016 | 4-(benzyloxy)phenylglyoxyl | 144–145 | 439.0 |
| 2017 | 4-[(2-methoxy-4-nitrobenzyl)oxy]phenylglyoxyl | 197–198 | 514.0 |
| 2018 | CF$_2$-naphthyl | | |
| 2019 | 4-cyclohexyl-CF$_2$-phenyl | 166–167 | 437.0 |
| 2020 | 3-chloro-CF$_2$-phenyl | 167–168 | 389.0 |
| 2021 | long chain aldehyde | 63–64 | |
| 2022 | 2,6-diphenoxybenzoyl | | 517.0 |

TABLE 3-continued

[Structure: pyridine with SCH3 at position 4, SCH3 at position 2, H3C at position 6, and NH-C(=O)-R at position 3]

| Ex. No. | R | m.p. | M.S(M⁺ + H) |
|---|---|---|---|
| 2023 | [4-(2-chloro-4,5-methylenedioxybenzyloxy)benzoyl group] | 198–199 | 517.0 |
| 2024 | CF$_2$-(long alkyl chain) | | 475 |
| 2025 | [pyridine with SCH3, SCH3, H3C, N=C-C$_{16}$H$_{33}$] | | 635 |
| 2026 | C(CF$_3$)(OCH$_3$)-CH$_2$-phenyl | | 417 |
| 2027 | 4-chloro-2-(CF$_2$-)-1-nitrophenyl | 196–198 | 434.0 |
| 2028 | 3-iodo-(CF$_2$-)phenyl | 169–170 | 481.0 |
| 2029 | 4-chloro-(CF$_2$-)phenyl | 162–164 | 389.0 |
| 2030 | 2-fluoro-4-ethyl-5-fluoro-benzoyl | 153–155 | 397.0 |
| 2031 | 2-(propylthio)benzoyl | 153–154 | 407.0 |
| 2032 | 4'-(CF$_2$-)biphenyl | 173–174 | 431.0 |
| 2033 | 4-(CF$_3$)-(CF$_2$-)phenyl | 179–180.5 | 423.0 |
| 2034 | heptanoyl | 112.7–114.9 | 341.0 |

TABLE 3-continued
[Structure: pyridine with SCH3 at 4-position, SCH3 at 2-position, CH3 at 6-position, NH-C(=O)-R at 3-position]
| Ex. No. | R | m.p. | M.S(M+ + H) |
|---------|---|------|-------------|
| 2035 | 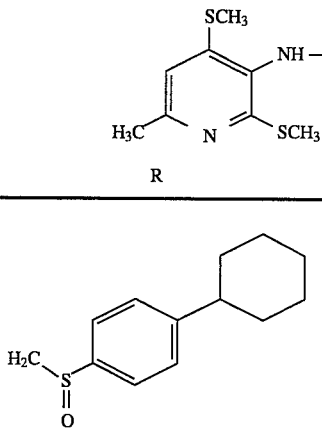 | 173–175 | 449.1 |
| 2036 | 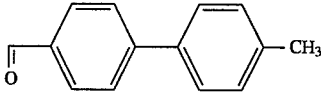 | | |
| 2037 | 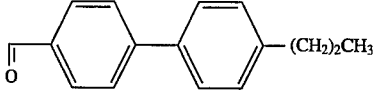 | | |
| 2038 | 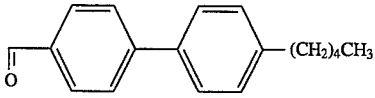 | | |
| 2039 | 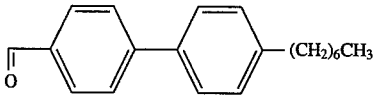 | | |
| 2040 | 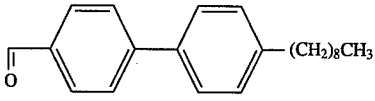 | | |
| 2041 | 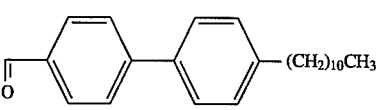 | | |
| 2042 | 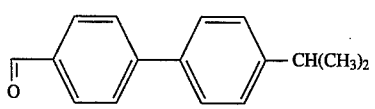 | | |
| 2043 | 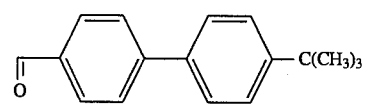 | | |
| 2044 | 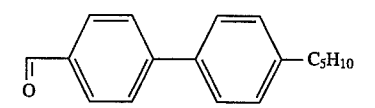 | | |
| 2045 | 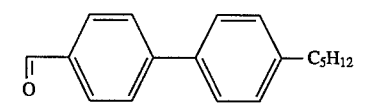 | | |
| 2046 | 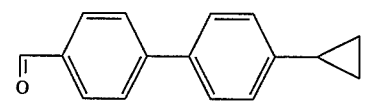 | | |

TABLE 3-continued

[Structure: pyridine with SCH3 groups at positions 2,4; NH-C(=O)-R at position 3; H3C at position 6]

| Ex. No. | R | m.p. | M.S.(M⁺ + H) |
|---------|---|------|--------------|
| 2047 | 4'-CH(CH₃)₂-3'-F-biphenyl-4-yl-C(=O)- | | |
| 2048 | 4'-CH(CH₃)₂-3'-Cl-biphenyl-4-yl-C(=O)- | | |
| 2049 | 4'-CH(CH₃)₂-3'-NO₂-biphenyl-4-yl-C(=O)- | | |
| 2050 | 4'-CH(CH₃)₂-3'-CN-biphenyl-4-yl-C(=O)- | | |
| 2051 | 4'-CH(CH₃)₂-3'-OCH₃-biphenyl-4-yl-C(=O)- | | |
| 2052 | 4'-CH(CH₃)₂-3'-O(CH₂)₃CH₃-biphenyl-4-yl-C(=O)- | | |
| 2053 | 4-phenoxyphenyl-C(=O)- | | 425.0 |
| 2054 | 4-(4-CH(CH₃)₂-phenoxy)phenyl-C(=O)- | | |
| 2055 | 4-(4-CH(CH₃)₂-3-F-phenoxy)phenyl-C(=O)- | | |
| 2056 | 4-(4-CH(CH₃)₂-3-CF₃-phenoxy)phenyl-C(=O)- | | |

TABLE 3-continued

Structure: pyridine with SCH3 (top), NH-C(=O)-R, SCH3, and H3C, with N in ring

| Ex. No. | R | m.p. | M.S(M⁺ + H) |
|---------|---|------|-------------|
| 2057 | 4-(phenylthio)benzoyl [C(=O)-C6H4-S-C6H5] | | |
| 2058 | 4-[(4-isopropylphenyl)thio]benzoyl [C(=O)-C6H4-S-C6H4-CH(CH3)2] | | |
| 2059 | 4-[(3-fluoro-4-isopropylphenyl)thio]benzoyl | | |
| 2060 | 4-[(3-trifluoromethyl-4-isopropylphenyl)thio]benzoyl | | |
| 2061 | 4-pentylbenzoyl [C(=O)-C6H4-(CH2)4-CH3] | | |
| 2062 | 4-heptylbenzoyl [C(=O)-C6H4-(CH2)6-CH3] | | |
| 2063 | 4-nonylbenzoyl [C(=O)-C6H4-(CH2)8-CH3] | | |
| 2064 | 3-heptyl-4-pentylbenzoyl | | |
| 2065 | 3,4-bis(heptyl)benzoyl | | |
| 2066 | 4-pentyloxybenzoyl [C(=O)-C6H4-O(CH2)4CH3] | | |
| 2067 | 4-heptyloxybenzoyl [C(=O)-C6H4-O(CH2)6CH3] | | |

TABLE 3-continued

[Structure: pyridine ring with SCH₃ at position 4, NH-C(=O)-R at position 3, SCH₃ at position 2, CH₃ at position 6]

| Ex. No. | R | m.p. | M.S(M⁺ + H) |
|---|---|---|---|
| 2068 | 4-O(CH₂)₄CH₃, 3-(CH₂)₆—CH₃ benzoyl | | |
| 2069 | 3,4-di-O(CH₂)₆CH₃ benzoyl | | |
| 2070 | 3,5-di-O(CH₂)₆CH₃, 4-O—CH₃ benzoyl | | |
| 2071 | 4-S(CH₂)₄CH₃ benzoyl | | |
| 2072 | 4-S(CH₂)₆CH₃ benzoyl | | |
| 2073 | 4-S(CH₂)₄CH₃, 3-(CH₂)₆—CH₃ benzoyl | | |
| 2074 | 3-O(CH₂)₆CH₃, 4-S(CH₂)₆CH₃ benzoyl | | |
| 2075 | 3,5-di-O(CH₂)₆CH₃, 4-S—CH₃ benzoyl | | |
| 2076 | 3,4-di-S(CH₂)₆CH₃ benzoyl | | |
| 2077 | —C(=O)—CH[(CH₂)₆—CH₃][(CH₂)₄—CH₃] | | |

TABLE 3-continued

[Structure: pyridine ring with SCH₃ at 4-position, NHC(O)R at 3-position, SCH₃ at 2-position, H₃C at 6-position, N at 1-position]

| Ex. No. | R | m.p. | M.S(M⁺ + H) |
|---------|---|------|-------------|
| 2078 | —C(O)—CH[(CH₂)₆—CH₃][(CH₂)₆—CH₃] | | |
| 2079 | —C(O)—CH[(CH₂)₈—CH₃][(CH₂)₅—CH₃] | | |
| 2080 | —C(O)—CH[(CH₂)₈—CH₃][(CH₂)₈—CH₃] | | |
| 2081 | —C(O)—cyclohexyl—O(CH₂)₄CH₃ | | |
| 2082 | —C(O)—cyclohexyl—(CH₂)₄—CH₃ | | |
| 2083 | —C(O)—cyclohexyl—(CH₂)₆—CH₃ | | |
| 2084 | —C(O)—cyclohexyl—(CH₂)₈—CH₃ | | |
| 2085 | —C(O)—cyclohexyl[(CH₂)₆—CH₃][(CH₂)₄—CH₃] | | |
| 2086 | —C(O)—cyclohexyl[(CH₂)₆—CH₃][(CH₂)₆—CH₃] | | |
| 2087 | CF₂—C₆H₄—C₆H₄—CH₃ | | |
| 2088 | CF₂—C₆H₄—C₆H₄—(CH₂)₂CH₃ | | |
| 2089 | CF₂—C₆H₄—C₆H₄—(CH₂)₄CH₃ | | |

TABLE 3-continued
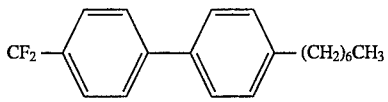
| Ex. No. | R | m.p. | M.S(M⁺ + H) |
|---|---|---|---|
| 2090 | 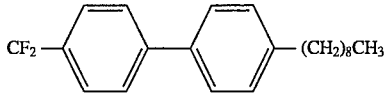 | | |
| 2091 | 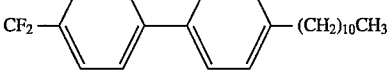 | | |
| 2092 | 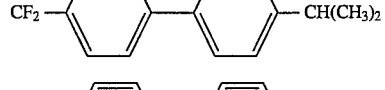 | | |
| 2093 | 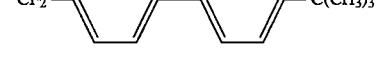 | | |
| 2094 | 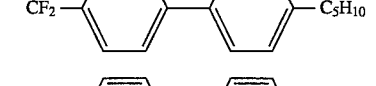 | | |
| 2095 | 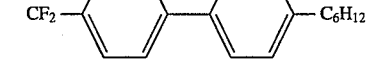 | | |
| 2096 | 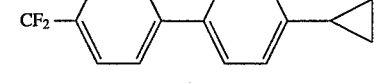 | | |
| 2097 | 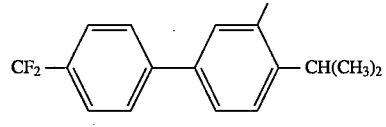 | | |
| 2098 | 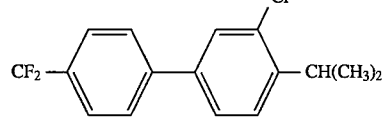 | | |
| 2099 | 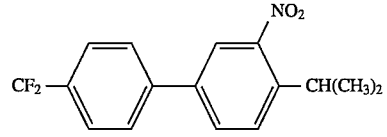 | | |
| 2100 | 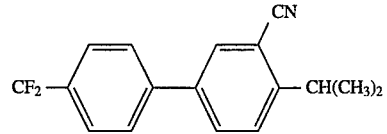 | | |
| 2101 |  | | |

TABLE 3-continued

Structure: pyridine with SCH₃ (4-position), NH-C(=O)-R (3-position), SCH₃ (2-position), H₃C (6-position), N (ring)

| Ex. No. | R | m.p. | M.S(M⁺ + H) |
|---|---|---|---|
| 2102 | 4-(4-methoxy-4-isopropylphenyl)-CF₂-phenyl (CF₂–C₆H₄–C₆H₃(OCH₃)(CH(CH₃)₂)) | | |
| 2103 | CF₂–C₆H₄–C₆H₃(O(CH₂)₃CH₃)(CH(CH₃)₂) | | |
| 2104 | CF₂–C₆H₄–O–C₆H₅ | 81–82 | 447.0 |
| 2105 | CF₂–C₆H₄–O–C₆H₄–CH(CH₃)₂ | | |
| 2106 | CF₂–C₆H₄–O–C₆H₃(F)(CH(CH₃)₂) | | |
| 2107 | CF₂–C₆H₄–O–C₆H₃(CF₃)(CH(CH₃)₂) | | |
| 2108 | CF₂–C₆H₄–S–C₆H₅ | | |
| 2109 | CF₂–C₆H₄–S–C₆H₄–CH(CH₃)₂ | | |
| 2110 | CF₂–C₆H₄–S–C₆H₃(F)(CH(CH₃)₂) | | |
| 2111 | CF₂–C₆H₄–S–C₆H₃(CF₃)(CH(CH₃)₂) | | |
| 2112 | CF₂–C₆H₄–(CH₂)₄–CH₃ | | |

TABLE 3-continued
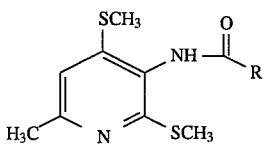
| Ex. No. | R | m.p. | M.S(M⁺ + H) |
|---|---|---|---|
| 2113 | 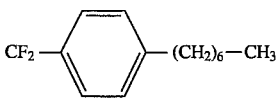 | | |
| 2114 | 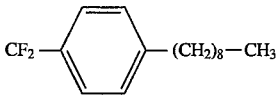 | | |
| 2115 | 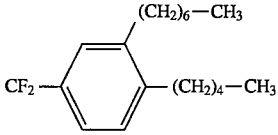 | | |
| 2116 | 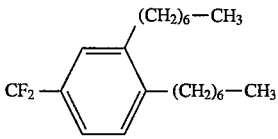 | | |
| 2117 | 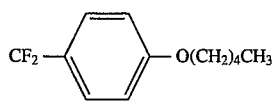 | | |
| 2118 | 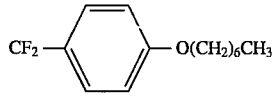 | | |
| 2119 | 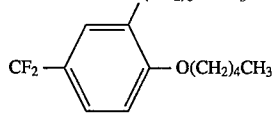 | | |
| 2120 | 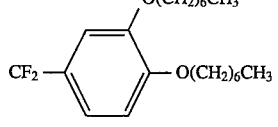 | | |
| 2121 | 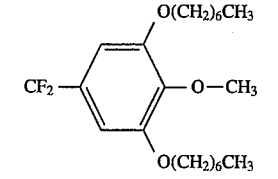 | | |
| 2122 | 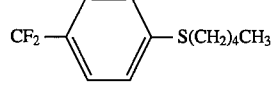 | | |
| 2123 | 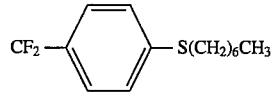 | | |

TABLE 3-continued

Structure: pyridine with SCH₃ at 4-position, NHC(=O)R at 3-position, SCH₃ at 2-position, H₃C at 6-position, N in ring.

| Ex. No. | R | m.p. | M.S(M⁺ + H) |
|---|---|---|---|
| 2124 | 4-CF₂, 1-S(CH₂)₄CH₃, 2-(CH₂)₆—CH₃ phenyl | | |
| 2125 | 4-CF₂, 1-S(CH₂)₆CH₃, 2-O(CH₂)₆CH₃ phenyl | | |
| 2126 | 4-CF₂, 1-S—CH₃, 2,6-di-O(CH₂)₆CH₃ phenyl | | |
| 2127 | 4-CF₂, 1-S(CH₂)₆CH₃, 2-S(CH₂)₆CH₃ phenyl | | |
| 2128 | CF₂—CH[(CH₂)₆—CH₃][(CH₂)₄—CH₃] | | |
| 2129 | CF₂—CH[(CH₂)₆—CH₃][(CH₂)₆—CH₃] | | |
| 2130 | CF₂—CH[(CH₂)₈—CH₃][(CH₂)₅—CH₃] | | |
| 2131 | CF₂—CH[(CH₂)₈—CH₃][(CH₂)₈—CH₃] | | |
| 2132 | CF₂-cyclohexyl-O(CH₂)₄CH₃ | | |
| 2133 | CF₂-cyclohexyl-(CH₂)₄—CH₃ | | |
| 2134 | CF₂-cyclohexyl-(CH₂)₆—CH₃ | | |

TABLE 3-continued

[Structure: pyridine with SCH3 at two positions, CH3, and NH-C(=O)-R substituent]

| Ex. No. | R | m.p. | M.S(M⁺ + H) |
|---|---|---|---|
| 2135 | CF₂-cyclohexyl-(CH₂)₈-CH₃ | | |
| 2136 | CF₂-cyclohexyl with (CH₂)₆-CH₃ and (CH₂)₄-CH₃ | | |
| 2137 | CF₂-cyclohexyl with (CH₂)₆-CH₃ and (CH₂)₆-CH₃ | | |
| 2138 | C(=O)-biphenyl | 219–221 | 409.0 |
| 2139 | C(=O)-phenyl | 229–231 | 411.0 |

What is claimed is:

1. A compound of Formula I:

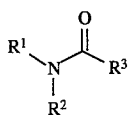

(I)

or stereoisomer or pharmaceutically acceptable salt thereof, wherein:

$R^1$ is selected from the following heterocyclic groups:

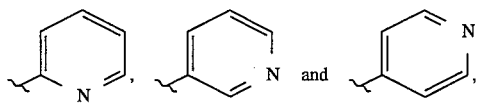

each such heterocyclic group may optionally be fused to a benzene ring, and each such heterocyclic group and fused benzene ring is substituted with 1–3 $R^{30}$ or phenyl, said phenyl being substituted with 0–3 $R^{30}$;

$R^{30}$ is selected independently from: $C_1$-$C_4$ straight chain alkyl, $C_3$-$C_6$ branched alkyl, $C_3$-$C_8$ cycloalkyl, $C_4$-$C_9$ cycloalkylalkyl, $C_1$-$C_4$ alkoxy, $C_1$-$C_4$ alkylthio, $C_2$-$C_8$ dialkylamino, halogen, and nitro;

$R^2$ is H;

$R^3$ is independently selected from the following groups:
—CH₂—X—$R^4$ and —C($R^5$)($R^6$)—X—$R^7$;

$R^4$ is selected from:
$C_{4-20}$ alkyl substituted with 0–6 $R^{12}$,
$C_{5-20}$ alkenyl substituted with 0–6 $R^{12}$,
$C_{5-20}$ alkynyl substituted with 0–6 $R^{12}$,
$C_{4-12}$ cycloalkyl substituted with 0–6 $R^{12}$,
$C_{5-16}$ cycloalkylalkyl substituted with 0–6 $R^{12}$,
$C_{4-12}$ cycloalkenyl substituted with 0–6 $R^{12}$,
$C_{6-16}$ cycloalkenylalkyl substituted with 0–6 $R^{12}$,
$C_{6-16}$ bicycloalkylalkyl substituted with 0–6 $R^{12}$,
$C_{8-16}$ bicycloalkenylalkyl substituted with 0–6 $R^{12}$, and adamantyl substituted with 0–3 $R^{12}$;

$R^5$ is selected from:
aryl substituted with 0–5 $R^{13}$ and
$R^{17}$ substituted with 0–5 $R^{13}$;

$R^6$ is H;

$R^7$ is selected from:
$C_{1-20}$ alkyl substituted with 0–6 $R^{12}$,
$C_{2-20}$ alkenyl substituted with 0–6 $R^{12}$,
$C_{2-20}$ alkynyl substituted with 0–6 $R^{12}$,
$C_{3-12}$ cycloalkyl substituted with 0–6 $R^{12}$,
$C_{5-16}$ cycloalkylalkyl substituted with 0–6 $R^{12}$,
$C_{3-12}$ cycloalkenyl substituted with 0–6 $R^{12}$,
$C_{5-16}$ cycloalkenylalkyl substituted with 0–6 $R^{12}$,
$C_{6-16}$ bicycloalkyl substituted with 0–6 $R^{12}$,
$C_{6-16}$ bicycloalkenyl substituted with 0–6 $R^{12}$,
$C_{6-16}$ bicycloalkylalkyl substituted with 0–6 $R^{12}$,
$C_{8-16}$ bicycloalkenylalkyl substituted with 0–6 $R^{12}$,
aryl substituted with 0–5 $R^{13}$, and
$R^{17}$ substituted with 0–5 $R^{13}$;

$R^{12}$ is selected from:
$R^{17}$, $OR^{17}$, $SR^{17}$, $NHR^{17}$, $R^{18}$, $OR^{18}$, $SR^{18}$, $NHR^{18}$, F, Cl, Br, I, $OR^{14}$, $OC(=O)R^{14}$, $OCO_2R^{14}$, $OC(=O)N(R^{14})R^{15}$, $NO_2$, $N(R^{14})R^{15}$, $S(O)_nR^{14}$, $C(=O)R^{14}$, $CO_2R^{14}$, $CON(R^{14})R^{15}$, CN, and tetrazole;

$R^{13}$ is selected from:

$R^{18}$, $OR^{18}$, $SR^{18}$, $NHR^{18}$,
$C_{1-8}$ alkyl substituted with 0–6 $R^{12}$,
$C_{2-8}$ alkenyl substituted with 0–6 $R^{12}$,
$C_{2-8}$ alkynyl substituted with 0–6 $R^{12}$,
F, Cl, I, $CF_3$, $OR^{14}$, $OCOR^{14}$, $OCO_2R^{14}$, $OCONR^{14}R^{15}$, $NO_2$,
$NR^{14}R^{15}$, $NR^{14}SO_2R^{15}$, $NR^{14}SO_2CF_3$, $SR^{14}$, $S(=O)R^{14}$, $S(=O)_2R^{14}$,
$C(=O)R^{14}$, $CO_2R^{14}$, $CONR^{14}R^{15}$, CN, and tetrazole;

$R^{14}$ is selected from H, $C_{1-6}$ alkyl, $C_{2-6}$ alkenyl, $C_{2-6}$ alkylnyl, and $R^{18}$;

$R^{15}$ is selected from H, $C_{1-6}$ alkyl, $C_{2-6}$ alkenyl, $C_{2-6}$ alkynyl, and $R^{18}$;

$R^{14a}$ is selected from H, $C_{1-6}$ alkyl, $C_{2-6}$ alkenyl, $C_{2-6}$ alkynyl, and aryl, said aryl being substituted with 0–3 groups selected independently from halogen, $C_1$–$C_4$ alkyl, $C_1$–$C_3$ haloalkyl, CN, $C_1$–$C_4$ alkoxy, and $NO_2$;

$R^{15a}$ is selected from H, $C_{1-6}$ alkyl, $C_{2-6}$ alkenyl, $C_{2-6}$ alkynyl, and aryl, said aryl being substituted with 0–3 groups selected independently from halogen, $C_1$–$C_4$ alkyl, $C_1$–$C_3$ haloalkyl, CN, $C_1$–$C_4$ alkoxy, and $NO_2$;

$R^{17}$ is selected from: pyridyl, pyrimidyl, pyrazinyl, furyl, thienyl, pyrrolyl, indolyl, quinolyl, isoquinolyl, benzothiophenyl, imidazolyl, oxazolyl, isoxazolyl, thiazolyl, isothiazolyl, and pyrazolyl;

$R^{18}$ is aryl substituted with 0–5 $R^{19}$;

$R^{19}$ is selected from $C_{1-6}$ alkyl, $C_{2-5}$ alkenyl, $C_{2-5}$ alkynyl, F, Cl, Br, I, $CF_3$, $OR^{14a}$, $NO_2$, $NR^{14a}R^{15a}$, $S(O)_nR^{14a}$, $C(=O)R^{14a}$, $CO_2R^{14a}$, $C(=O)NR^{14a}R^{15a}$, $C_1$–$C_3$ haloalkyl, and CN;

X is O or $S(O)_n$; and n is 0, 1 or 2;

with the following proviso:
(1) when $R^3$ is —$CH_2XR^4$, then $R^4$ cannot be straight chain alkyl.

2. A compound according to claim 1, or stereoisomer or pharmaceutically acceptable salt form thereof, wherein:
X is $S(O)_n$.

3. A compound according to claim 1, or stereoisomer or pharmaceutically acceptable salt form thereof, wherein:
$R^4$ is selected from:
$C_{4-20}$ alkyl substituted with 0–6 $R^{12}$,
$C_{5-20}$ alkenyl substituted with 0–6 $R^{12}$,
$C_{5-20}$ alkynyl substituted with 0–6 $R^{12}$,
$C_{4-12}$ cycloalkyl substituted with 0–6 $R^{12}$,
$C_{5-16}$ cycloalkylalkyl substituted with 0–6 $R^{12}$,
$C_{4-12}$ cycloalkenyl substituted with 0–6 $R^{12}$, and
$C_{6-16}$ cycloalkenylalkyl substituted with 0–6 $R^{12}$; and $R^7$ is selected from:
$C_{1-10}$ alkyl substituted with 0–6 $R^{12}$,
$C_{2-20}$ alkenyl substituted with 0–6 $R^{12}$,
$C_{2-20}$ alkynyl substituted with 0–6 $R^{12}$,
$C_{5-12}$ cycloalkylalkyl substituted with 0–6 $R^{12}$,
$C_{5-12}$ cycloalkenylalkyl substituted with 0–6 $R^{12}$,
aryl substituted with 0–5 $R^{13}$, and
$R^{17}$ substituted with 0–5 $R^{13}$.

4. A compound according to claim 1, or stereoisomer or pharmaceutically acceptable salt form thereof, wherein:

$R^1$ is selected from the following heterocyclic groups:

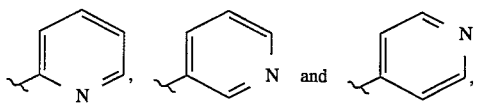

each such heterocyclic group and each such heterocyclic group fused to a benzene ring is substituted with 1–2 $R^{30}$ or phenyl, said phenyl being substituted with 0–2 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, and nitro;

$R^4$ is selected from:
$C_{4-20}$ alkyl substituted with 0–4 $R^{12}$, and
$C_{5-20}$ alkenyl substituted with 0–4 $R^{12}$;

$R^7$ is selected from:
$C_{1-10}$ alkyl substituted with 0–4 $R^{12}$,
$C_{2-20}$ alkenyl substituted with 0–4 $R^{12}$,
$C_{5-12}$ cycloalkylalkyl substituted with 0–4 $R^{12}$,
aryl substituted with 0–3 $R^{13}$, and
$R^{17}$ substituted with 0–3 $R^{13}$;

$R^{13}$ is selected from:
$R^{18}$, $OR^{18}$, $SR^{18}$, $NHR^{18}$, $C_{1-8}$ alkyl substituted with 0–4 $R^{12}$, F, Cl, Br, I, $CF_3$, $OR^{14}$, $OC(=O)R^{14}$, $NO_2$, $NR^{14}R^{15}$,
$NR^{14}SO_2R^{15}$, $NR^{14}SO_2CF_3$, $SR^{14}$, $S(=O)R^{14}$, $S(=O)_2R^{14}$,
$C(=O)R^{14}$, $CO_2R^{14}$, $C(=O)NR^{14}R^{15}$, CN, and tetrazole;

$R^{14}$ is selected from H, $C_{1-6}$ alkyl, and $R^{18}$;

$R^{15}$ is selected from H, $C_{1-6}$ alkyl, $C_{2-6}$ alkenyl, and $R^{18}$; and $R^{16}$ is selected from:
$C_{1-6}$ alkyl substituted with 0–4 $R^{12}$,
$C_{2-6}$ alkenyl substituted with 0–4 $R^{12}$, and
aryl substituted with 0–3 $R^{19}$.

5. A compound according to claim 1, or stereoisomer or pharmaceutically acceptable salt thereof, wherein:
$R^3$ is —$CH_2$—X—$R^4$.

6. A compound according to claim 1, or stereoisomer or pharmaceutically acceptable salt thereof, wherein:
$R^3$ is —$CH_2$—X—$R^4$; and
$R^4$ is selected from:
$C_{4-20}$ alkyl substituted with 0–6 $R^{12}$,
$C_{5-20}$ alkenyl substituted with 0–6 $R^{12}$,
$C_{5-20}$ alkynyl substituted with 0–6 $R^{12}$,
$C_{4-12}$ cycloalkyl substituted with 0–6 $R^{12}$,
$C_{5-16}$ cycloalkylalkyl substituted with 0–6 $R^{12}$,
$C_{4-12}$ cycloalkenyl substituted with 0–6 $R^{12}$, and
$C_{6-16}$ cycloalkenylalkyl substituted with 0–6 $R^{12}$.

7. A compound according to claim 1, or stereoisomer or pharmaceutically acceptable salt thereof, wherein:
$R^1$ is selected from the following heterocyclic groups:

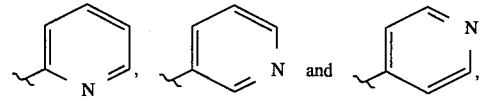

each such heterocyclic group may optionally be fused to a benzene ring, and each such heterocyclic group and each such heterocyclic group fused to a benzene ring is substituted with 1–2 $R^{30}$ or phenyl, said phenyl being substituted with 0–2 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, or nitro;

$R^3$ is —$CH_2$—X—$R^4$;

$R^4$ is selected from:
$C_{4-20}$ alkyl substituted with 0–4 $R^{12}$, and
$C_{5-20}$ alkenyl substituted with 0–4 $R^{12}$;

$R^{13}$ is selected from:
$R^{18}$, $OR^{18}$, $SR^{18}$, $NHR^{18}$, $C_{1-8}$ alkyl substituted with 0–4
$R^{12}$, F, Cl, Br, I, $CF_3$, $OR^{14}$, $OC(=O)R^{14}$, $NO_2$, $NR^{14}R^{15}$,
$NR^{14}SO_2R^{15}$, $NR^{14}SO_2CF_3$, $SR^{14}$, $S(=O)R^{14}$, $S(=O)_2R^{14}$,
$C(=O)R^{14}$, $CO_2R^{14}$, $C(=O)NR^{14}R^{15}$, CN, and tetrazole;

$R^{14}$ is selected from H, $C_{1-6}$ alkyl, and $R^{18}$; and
$R^{15}$ is selected from H, $C_{1-6}$ alkyl, $C_{2-6}$ alkenyl, and $R^{18}$.

8. A compound according to claim 1, or stereoisomer or pharmaceutically acceptable salt thereof, wherein:
$R^3$ is —$C(R^5)(R^6)$—X—$R^7$.

9. A compound according to claim 1, or stereoisomer or pharmaceutically acceptable salt thereof, wherein:
$R^3$ is —$C(R^5)(R^6)$—X—$R^7$; and
$R^7$ is selected from:
$C_{1-10}$ alkyl substituted with 0–6 $R^{12}$,
C2-20 alkenyl substituted with 0–6 $R^{12}$,
C2-20 alkynyl substituted with 0–6 $R^{12}$,
$C_{5-12}$ cycloalkylalkyl substituted with 0–6 $R^{12}$,
$C_{5-12}$ cycloalkenylalkyl substituted with 0–6 $R^{12}$,
aryl substituted with 0–5 $R^{13}$, and
$R^{17}$ substituted with 0–5 $R^{13}$.

10. A compound according to claim 1, or stereoisomer or pharmaceutically acceptable salt thereof, wherein:
$R^1$ is selected from the following heterocyclic groups:

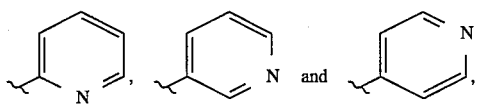

each such heterocyclic group may optionally be fused to a benzene ring, and each such heterocyclic group and each such heterocyclic group fused to a benzene ring is substituted with 1–2 $R^{30}$ or phenyl, said phenyl being substituted with 0–2 $R^{30}$;

$R^{30}$ is selected independently from: $C_1$–$C_4$ straight chain alkyl, $C_3$–$C_6$ branched alkyl, $C_1$–$C_4$ alkoxy, $C_1$–$C_4$ alkylthio, $C_2$–$C_8$ dialkylamino, halogen, or nitro;

$R^3$ —$C(R^5)(R^6)$—X—$R^7$;
$R^7$ is selected from:
$C_{1-10}$ alkyl substituted with 0–4 $R^{12}$,
$C_{2-20}$ alkenyl substituted with 0–4 $R^{12}$,
$C_{5-12}$ cycloalkylalkyl substituted with 0–4 $R^{12}$,
aryl substituted with 0–3 $R^{13}$, and
$R^{17}$ substituted with 0–3 $R^{13}$;

$R^{13}$ is selected from:
$R^{18}$, $OR^{18}$, $SR^{18}$, $NHR^{18}$, $C_{1-8}$ alkyl substituted with 0–4
$R^{12}$, F, Cl, Br, I, $CF_3$, $OR^{14}$, $OC(=O)R^{14}$, $NO_2$, $NR^{14}R^{15}$,
$NR^{14}SO_2R^{15}$, $NR^{14}SO_2CF_3$, $SR^{14}$, $S(=O)R^{14}$, $S(=O)_2R^{14}$,
$C(=O)R^{14}$, $CO_2R^{14}$, $C(=O)NR^{14}R^{15}$, CN, and tetrazole;

$R^{14}$ is selected from H, $C_{1-6}$ alkyl, or $R^{18}$; and
$R^{15}$ is selected from H, $C_{1-6}$ alkyl, $C_{2-6}$ alkenyl, and $R^{18}$.

11. A compound or stereoisomer or pharmaceutically acceptable salt thereof, selected from:

N-[2,4-bis(methylthio)-6-methyl-3-pyridyl]-D-(−)-α-O-hexyl-mandeloamide;
N-[2,4-bis(methylthio)-6-methyl-3-pyridyl]-L-(+)-α-O-hexyl-mandeloamide;
N-[2,4-bis(methylthio)-6-methyl-3-pyridyl]-L-(+)-α-O-benzyl-mandeloamide;
N-[2,4-bis(methylthio)-6-methyl-3-pyridyl]-D-(−)-α-hexylthio-phenylacetamide;
N-[2,4-bis(methylthio)-6-methyl-3-pyridyl]-L-(+)-α-hexylthio-phenylacetamide;
N-[2,4-bis(methylthio)-6-methyl-3-pyridyl]-D-(−)-α-benzylthio-phenylacetamide;
N-[2,4-bis(methylthio)-6-methyl-3-pyridyl]-L-(+)-α-benzylthio-phenylacetamide;
N-[2,4-bis(methylthio)-6-methyl-3-pyridyl]-D-(−)-α-ethylthio-phenylacetamide;
N-[2,4-bis(methylthio)-6-methyl-3-pyridyl]-L-(+)-α-ethylthio-phenylacetamide;
N-[2,4-bis(methylthio)-6-methyl-3-pyridyl]-L-(+)-α-phenylthio-phenylacetamide;
N-[2,4-bis(methylthio)-6-methyl-3-pyridyl]-α-hexylthio-4-chloro-phenylacetamide;
N-[2,4-bis(methylthio)-6-methyl-3-pyridyl]-α-benzylthio-4-chloro-phenylacetamide;
N-[2,4-bis(methylthio)-6-methyl-3-pyridyl]-α-(4-methoxybenzylthio)-4-chloro-phenylacetamide;
N-[2,4-bis(methylthio)-6-methyl-3-pyridyl]-α-(4-fluorobenzylthio)-4-chloro-phenylacetamide;
N-[2,4-bis(methylthio)-6-methyl-3-pyridyl]-α-(4-chlorobenzylthio)-4-chloro-phenylacetamide;
N-[2,4-bis(methylthio)-6-methyl-3-pyridyl]-α-phenylthio-4-chloro-phenylacetamide;
N-[2,4-bis(methylthio)-6-methyl-3-pyridyl]-α-(4-methoxyphenylthio)-4-chloro-phenylacetamide;
N-[2,4-bis(methylthio)-6-methyl-3-pyridyl]-α-(4-fluorophenylthio)-4-chloro-phenylacetamide;
N-[2,4-bis(methylthio)-6-methyl-3-pyridyl]-α-hexylthio-4-methoxy-phenylacetamide;
N-[2,4-bis(methylthio)-6-methyl-3-pyridyl]-α-benzylthio-4-methoxy-phenylacetamide;
N-[2,4-bis(methylthio)-6-methyl-3-pyridyl]-α-(4-chlorobenzylthio)-4-methoxy-phenylacetamide;
N-[2,4-bis(methylthio)-6-methyl-3-pyridyl]-α-(4-fluorobenzylthio)-4-methoxy-phenylacetamide;
N-[2,4-bis(methylthio)-6-methyl-3-pyridyl]-α-(4-methoxybenzylthio)-4-methoxy-phenylacetamide;
N-[2,4-bis(methylthio)-6-methyl-3-pyridyl]-α-phenylthio-4-methoxy-phenylacetamide;
N-[2,4-bis(methylthio)-6-methyl-3-pyridyl]-α-(4-fluorophenylthio)-4-methoxy-phenylacetamide;
N-[2,4-bis(methylthio)-6-methyl-3-pyridyl]-α-(4-methoxyphenylthio)-4-methoxy-phenylacetamide;
N-[2,4-bis(methylthio)-6-methyl-3-pyridyl]-α-O-methyl-4-methoxymandeloamide;
N-[2,4-bis(methylthio)-6-methyl-3-pyridyl]-α-hexylthio-4-fluoro-phenylacetamide;
N-[2,4-bis(methylthio)-6-methyl-3-pyridyl]-α-benzylthio-4-fluoro-phenylacetamide;
N-[2,4-bis(methylthio)-6-methyl-3-pyridyl]-α-(4-fluorobenzylthio)-4-fluoro-phenylacetamide;
N-[2,4-bis(methylthio)-6-methyl-3-pyridyl]-α-(4-methoxybenzylthio)-4-fluoro-phenylacetamide, N-[2,4-bis(methylthio)-6-methyl-3-pyridyl]-α-phenylthio-4-fluoro-phenylacetamide;
N-[2,4-bis(methylthio)-6-methyl-3-pyridyl]-α-(4-fluorophenylthio)-4-fluoro-phenylacetamide;
N-[2,4-bis(methylthio)-6-methyl-3-pyridyl]-α-(4-methoxyphenylthio)-4-fluoro-phenylacetamide;
N-[2,4-bis(methylthio)-6-methyl-3-pyridyl]-α-hexylthio-3,4-dichloro-phenylacetamide;
N-[2,4-bis(methylthio)-6-methyl-3-pyridyl]-α-benzylthio-3,4-dichloro-phenylacetamide;
N-[2,4-bis(methylthio)-6-methyl-3-pyridyl]-α-(4-fluorobenzylthio)-3,4-dichloro-phenylacetamide;
N-[2,4-bis(methylthio)-6-methyl-3-pyridyl]-α-(4-methoxybenzylthio)-3,4-dichloro-phenylacetamide;
N-[2,4-bis(methylthio)-6-methyl-3-pyridyl]-α-hexylthio-2,4-difluoro-phenylacetamide;
N-[2,4-bis(methylthio)-6-methyl-3-pyridyl]-α-(4-methoxybenzylthio)-2,4-difluoro-phenylacetamide;
N-[2,4-bis(methylthio)-6-methyl-3-pyridyl]-α-hexylthio-3,4-dimethoxy-phenylacetamide;
N-[2,4-bis(methylthio)-6-methyl-3-pyridyl]-α-benzylthio-3,4-dimethoxy-phenylacetamide;
N-[2,4-bis(methylthio)-6-methyl-3-pyridyl]-α-(4-fluorobenzylthio)-3,4-dimethoxy-phenylacetamide;
N-[2,4-bis(methylthio)-6-methyl-3-pyridyl]-α-hexylthio-4-butoxy-phenylacetamide;
N-[2,4-bis(methylthio)-6-methyl-3-pyridyl]-α-benzylthio-4-butoxy-phenylacetamide;
N-[2,4-bis(methylthio)-6-methyl-3-pyridyl]-α-benzylthio-4-butoxy-phenylacetamide;
N-[2,4-bis(methylthio)-6-methyl-3-pyridyl]-α-hexylthio-4-phenoxy-phenylacetamide;
N-[2,4-bis(methylthio)-6-methyl-3-pyridyl]-α-benzylthio-4-phenoxy-phenylacetamide;
N-[2,4-bis(methylthio)-6-methyl-3-pyridyl]-α-(4-chlorobenzylthio)-4-phenoxy-phenylacetamide;
N-[2,4-bis(methylthio)-6-methyl-3-pyridyl]-α-hexylthio-3-phenoxy-phenylacetamide;
N-[2,4-bis(methylthio)-6-methyl-3-pyridyl]-α-hexylthio-3-(4'-bromophenoxy)-phenylacetamide;
N-[2,4-bis(methylthio)-6-methyl-3-pyridyl]-α-benzylthio-3-phenoxy-phenylacetamide;
N-[2,4-bis(methylthio)-6-methyl-3-pyridyl]-α-benzylthio-3-(4'-bromophenoxy)-phenylacetamide;
N-[2,4-bis(methylthio)-6-methyl-3-pyridyl]-α-(4-chlorobenzylthio)-3-phenoxy-phenylacetamide;
N-[2,4-bis(methylthio)-6-methyl-3-pyridyl]-α-(4-chlorobenzylthio)-3-(4'-bromophenoxy)-phenylacetamide;
N-[2,4-bis(methylthio)-6-methyl-3-pyridyl]-α-hexylthio-2-phenoxy-phenylacetamide;
N-[2,4-bis(methylthio)-6-methyl-3-pyridyl]-α-hexylthio-4-trifluoromethyl-phenylacetamide;
N-[2,4-bis(methylthio)-6-methyl-3-pyridyl]-α-benzylthio-4-trifluoromethyl-phenylacetamide;
N-[2,4-bis(methylthio)-6-methyl-3-pyridyl]-α-(4-fluorobenzylthio)-4-trifluoromethyl-phenylacetamide;
N-[2,4-bis(methylthio)-6-methyl-3-pyridyl]-α-(4-methoxybenzylthio)-4-trifluoromethyl-phenylacetamide;
N-[2,4-bis(methylthio)-6-methyl-3-pyridyl]-α-(4-fluorophenylthio)-4-trifluoromethyl-phenylacetamide;
N-[2,4-bis(methylthio)-6-methyl-3-pyridyl]-α-(4-methoxyphenylthio)-4-trifluoromethyl-phenylacetamide;
N-[2,4-bis(methylthio)-6-methyl-3-pyridyl]-α-hexylthio-4-isopropylphenylacetamide;
N-[2,4-bis(methylthio)-6-methyl-3-pyridyl]-α-benzylthio-4-isopropylphenylacetamide;
N-[2,4-bis(methylthio)-6-methyl-3-pyridyl]-α-(4-chlorobenzylthio)-4-isopropylphenylacetamide;
N-[2,4-bis(methylthio)-6-methyl-3-pyridyl]-α-(4-butoxybenzylthio)-4-isopropylphenylacetamide;
N-[2,4-bis(methylthio)-6-methyl-3-pyridyl]-α-hexylthio-4-tert-butylphenylacetamide;
N-[2,4-bis(methylthio)-6-methyl-3-pyridyl]-α-benzylthio-4-tert-butylphenylacetamide;
N-[2,4-bis(methylthio)-6-methyl-3-pyridyl]-α-(4-chlorobenzylthio)-4-tert-butylphenylacetamide;
N-[2,4-bis(methylthio)-6-methyl-3-pyridyl]-α-(4-tert-butylbenzylthio)-4-tert-butylphenylacetamide;
N-[2,4-bis(methylthio)-6-methyl-3-pyridyl]-α-hexylthio-4-biphenylacetamide;
N-[2,4-bis(methylthio)-6-methyl-3-pyridyl]-α-benzylthio-4-biphenylacetamide;
N-[2,4-bis(methylthio)-6-methyl-3-pyridyl]-α-(4-fluorobenzylthio)-4-biphenylacetamide;
N-[2,4-bis(methylthio)-6-methyl-3-pyridyl]-α-(4-methoxybenzylthio)-4-biphenylacetamide;
N-[2,4-bis(methylthio)-6-methyl-3-pyridyl]-α-(4-butoxybenzylthio)-4-biphenylacetamide;
N-[2,4-bis(methylthio)-6-methyl-3-pyridyl]-α-(3-pyridylmethylthio)-4-biphenylacetamide;
N-[2,4-bis(methylthio)-6-methyl-3-pyridyl]-α-hexylthio-4-nitro-phenylacetamide;
N-[2,4-bis(methylthio)-6-methyl-3-pyridyl]-α-hexylthio-3,4-methylenedioxyphenylacetamide;
N-[2,4-bis(methylthio)-6-methyl-3-pyridyl]-α-(4-chlorobenzylthio)-3,4-methylenedioxyphenylacetamide;
N-[2,4-bis(methylthio)-6-methyl-3-pyridyl]-α-hexylthio-2-thienylacetamide;
N-[2,4-bis(methylthio)-6-methyl-3-pyridyl]-α-hexylthio-4-butyl-phenylacetamide;
N-[2,4-bis(methylthio)-6-methyl-3-pyridyl]-α-(4-chlorobenzylthio)-4-butyl-phenylacetamide;
N-[2,4-bis(methylthio)-6-methyl-3-pyridyl]-α-(4-butylbenzylthio)-4-butyl-phenylacetamide;
N-[2,4-bis(methylthio)-6-methylpyridin-3-yl]-2-(2-butyldecylthio)-acetamide;
N-[2,4-bis(methylthio)-6-methylpyridin-3-yl]-1-(2-phenylheptylthio)acetamide;
N-[2,4-bis(methylthio)-6-methylpyridin-3-yl]-2-[(6,6-dimethylbicyclo[3.1.1]hepten-2-yl)methyl]thioacetamide;
N-[2,4-bis(methylthio)-6-methylpyridin-3-yl]-2-(E- and Z-2-pentyloct-2-enyl)thioacetamide;
N-[2,4-bis(methylthio)-6-methyl-3-pyridyl]-α-oxobenzeneacetamide;
N-[6-methyl-2,4-bis(methylthio)-3-pyridinyl]-2-oxodecanamide;
N-[6-methyl-2,4-bis(methylthio)-3-pyridinyl]-2-oxoundecanamide;
N-[6-methyl-2,4-bis(methylthio)-3-pyridinyl]-2-oxododecanamide;
N-[6-methyl-2,4-bis(methylthio)-3-pyridinyl]-2-oxotridecanamide;
N-[6-methyl-2,4-bis(methylthio)-3-pyridinyl]-2-oxotetradecanamide;
N-[6-methyl-2,4-bis(methylthio)-3-pyridinyl]-2-oxocyclohexaneacetamide;
4-methyl-N-[6-methyl-2,4-bis(methylthio)-3-pyridinyl]-alpha-oxocyclohexane-acetamide;
4-ethyl-N-[6-methyl-2,4-bis(methylthio)-3-pyridinyl]-alpha-oxocyclohexane-acetamide;
4-n-propyl-N-[6-methyl-2,4-bis(methylthio)-3-pyridinyl]-alpha-oxocyclohexane-acetamide;
4-n-butyl-N-[6-methyl-2,4-bis(methylthio)-3-pyridinyl]-alpha-oxocyclohexane-acetamide;
4-chloro-N-[6-methyl-2,4-bis(methylthio)-3-pyridinyl]-alpha-oxobenzene-acetamide;

4-fluoro-N-[6-methyl-2,4-bis(methylthio)-3-pyridinyl]-alpha-oxobenzene-acetamide;
4-bromo-N-[6-methyl-2,4-bis(methylthio)-3-pyridinyl]-alpha-oxobenzene-acetamide;
4-nitro-N-[6-methyl-2,4-bis(methylthio)-3-pyridinyl]-alpha-oxobenzene-acetamide;
4-methoxy-N-[6-methyl-2,4-bis(methylthio)-3-pyridinyl]-alpha-oxobenzene-acetamide;
4-phenoxy-N-[6-methyl-2,4-bis(methylthio)-3-pyridinyl]-alpha-oxobenzene-acetamide;
4-trifluoromethyl-N-[6-methyl-2,4-bis(methylthio)-3-pyridinyl]-alpha-oxobenzene-acetamide; and
N-[6-methyl-2,4-bis(methylthio)-3-pyridinyl]-alpha-oxo[1,1'-biphenyl]-4-acetamide.

12. A pharmaceutical composition comprising a compound of claim 1 and a pharmaceutically acceptable carrier.

13. A pharmaceutical composition comprising a compound of claim 2 and a pharmaceutically acceptable carrier.

14. A pharmaceutical composition comprising a compound of claim 3 and a pharmaceutically acceptable carrier.

15. A pharmaceutical composition comprising a compound of claim 4 and a pharmaceutically acceptable carrier.

16. A pharmaceutical composition comprising a compound of claim 5 and a pharmaceutically acceptable carrier.

17. A pharmaceutical composition comprising a compound of claim 6 and a pharmaceutically acceptable carrier.

18. A pharmaceutical composition comprising a compound of claim 7 and a pharmaceutically acceptable carrier.

19. A pharmaceutical composition comprising a compound of claim 8 and a pharmaceutically acceptable carrier.

20. A pharmaceutical composition comprising a compound of claim 9 and a pharmaceutically acceptable carrier.

21. A pharmaceutical composition comprising a compound of claim 10 and a pharmaceutically acceptable carrier.

22. A pharmaceutical composition comprising a compound of claim 11 and a pharmaceutically acceptable carrier.

23. A method of treating hypercholesterolemia or atherosclerosis in a mammal comprising administering to the mammal a therapeutically effective amount of a compound of claim 1.

24. A method of treating hypercholesterolemia or atherosclerosis in a mammal comprising administering to the mammal a therapeutically effective amount of a compound of claim 2.

25. A method of treating hypercholesterolemia or atherosclerosis in a mammal comprising administering to the mammal a therapeutically effective amount of a compound of claim 3.

26. A method of treating hypercholesterolemia or atherosclerosis in a mammal comprising administering to the mammal a therapeutically effective amount of a compound of claim 4.

27. A method of treating hypercholesterolemia or atherosclerosis in a mammal comprising administering to the mammal a therapeutically effective amount of a compound of claim 5.

28. A method of treating hypercholesterolemia or atherosclerosis in a mammal comprising administering to the mammal a therapeutically effective amount of a compound of claim 6.

29. A method of treating hypercholesterolemia or atherosclerosis in a mammal comprising administering to the mammal a therapeutically effective amount of a compound of claim 7.

30. A method of treating hypercholesterolemia or atherosclerosis in a mammal comprising administering to the mammal a therapeutically effective amount of a compound of claim 8.

31. A method of treating hypercholesterolemia or atherosclerosis in a mammal comprising administering to the mammal a therapeutically effective amount of a compound of claim 9.

32. A method of treating hypercholesterolemia or atherosclerosis in a mammal comprising administering to the mammal a therapeutically effective amount of a compound of claim 10.

33. A method of treating hypercholesterolemia or atherosclerosis in a mammal comprising administering to the mammal a therapeutically effective amount of a compound of claim 11.

* * * * *